US012702635B2

(12) United States Patent
Portal et al.

(10) Patent No.: US 12,702,635 B2
(45) **Date of Patent: *Aug. 11, 2026**

(54) COSMETIC COMPOSITION COMPRISING A POLYHYDROXYALKANOATE COPOLYMER BEARING A(N) (UN)SATURATED HYDROCARBON-BASED CHAIN AND A SURFACTANT

(71) Applicant: L'OREAL, Paris (FR)

(72) Inventors: Julien Portal, Aulnay-sous-Bois (FR); Romain Garcon, Aulnay-sous-Bois (FR)

(73) Assignee: L'OREAL, Paris (FR)

(*) Notice: Subject to any disclaimer, the term of this patent is extended or adjusted under 35 U.S.C. 154(b) by 445 days.

This patent is subject to a terminal disclaimer.

(21) Appl. No.: 17/794,753

(22) PCT Filed: Jun. 23, 2021

(86) PCT No.: PCT/EP2021/067263

§ 371 (c)(1),
(2) Date: Jul. 22, 2022

(87) PCT Pub. No.: WO2021/260078

PCT Pub. Date: Dec. 30, 2021

(65) Prior Publication Data

US 2023/0120675 A1 Apr. 20, 2023

(30) Foreign Application Priority Data

Jun. 24, 2020 (FR) ...................................... 2006624

(51) Int. Cl.
*A61K 8/85* (2006.01)
*A61K 8/39* (2006.01)
*A61K 8/894* (2006.01)
*A61Q 19/00* (2006.01)

(52) U.S. Cl.
CPC .................. *A61K 8/85* (2013.01); *A61K 8/39* (2013.01); *A61K 8/894* (2013.01); *A61Q 19/00* (2013.01)

(58) Field of Classification Search
CPC . A61K 8/85; A61K 8/39; A61K 8/894; A61K 8/416; A61K 8/4973; A61K 8/4993; A61Q 19/00; A61Q 1/00
See application file for complete search history.

(56) References Cited

U.S. PATENT DOCUMENTS

| | | | | |
|---|---|---|---|---|
| 5,958,480 | A | 9/1999 | Eggink et al. | |
| 2018/0265663 | A1 * | 9/2018 | Kuwagaki | C08J 3/14 |
| 2019/0159997 | A1 * | 5/2019 | Roveri | A61P 17/00 |

FOREIGN PATENT DOCUMENTS

| | | | | |
|---|---|---|---|---|
| EP | 2616038 | B1 | 10/2015 | |
| FR | 2 964 663 | A1 | 3/2012 | |
| FR | 3121353 | A1 | 10/2022 | |
| WO | WO 2011/069244 | A1 | 6/2011 | |
| WO | 2017195108 | A1 | 11/2017 | |
| WO | WO-2018178899 | A1 * | 10/2018 | A61K 8/025 |
| WO | WO 2020/128050 | A1 | 6/2020 | |
| WO | WO 2021/086927 | A1 | 5/2021 | |

OTHER PUBLICATIONS

Vippagunta et. al. "Crystalline solids" Advanced Drug Delivery Reviews 48 (2001) 3-26 (Year: 2001).*
Jacquel "Solubility of Polyhydroxyalkanoates by Experiment and Thermodynamic Correlations" 2007. (Year: 2007).*
Sudesh. "Synthesis of polyhydroxyalkanoate from palm oil and some new applications" Appl Microbiol Biotechnol (2011) 89:1373-1386 (Year: 2011).*
Li. "Water Soluble Polyhydroxyalkanoates: Future Materials for Therapeutic Applications" Chem. Soc. Rev., 2015, 44, 2865 (Year: 2015).*
Terada "Determination of solubility parameters for poly(3-hydroxyalkanoates)" International Journal of Biological Macromolecules 25 (1999) 207-215 (Year: 1999).*
Jérôme Lecomte: "Plant waxes: sources and applications", OCL, vol. 16, No. 4, Jul.-Dec. 2009, pp. 262-266.
"Categorizing Surface Energies | The Science of Adhesion | 3M in France"; 2025, pp. 1-7.
"Dyne per centimeter to Millinewton per meter"—https://www.unitsconverters.com/fr/Dyn/Cm-To-Mn/M/Utu-4431-4426, Date of Reference: 2025.
K. A. Ishak et al.: "Phase inversion of medium-chain-length poly-3-hydroxyalkanoates (mcl-PHA)-incorporated nanoemulsion: effects of mcl-PHA molecular weight and amount on its mechanism", Colloid. Polym. Sci, No. 294, 2016, pp. 1970-1981.
Zibiao Li et al.: "Polyhydroxyalkanoates: opening doors for a sustainable future," NPG Asia Materials (2016) 8, e265; doi:10.1038/am.2016.48.

* cited by examiner

*Primary Examiner* — Sean M Basquill
*Assistant Examiner* — Rajan Pragani
(74) *Attorney, Agent, or Firm* — POLSINELLI PC

(57) ABSTRACT

The present invention relates to a cosmetic composition comprising a) one or more polyhydroxyalkanoate (PHA) copolymers which contain, and preferably consist of, at least two different repeating polymer units chosen from the units (A) and (B) below, and also the optical or geometrical isomers thereof, the organic or mineral acid or base salts thereof, and the solvates thereof such as hydrates: -[-0-CH($R^1$)—$CH_2$—C(0)-]- unit (A) -[-0-CH($R^2$)—$CH_2$—C(0)-]- unit (B) in which polymer units (A) and (B): —$R^1$ represents a hydrocarbon-based chain chosen from i) linear or branched ($C_5$-$C_{28}$)alkyl, ii) linear or branched ($C_6$-$C_{28}$)alkenyl, iii) linear or branched ($C_6$-$C_{28}$)alkynyl; preferably, the hydrocarbon-based group is linear; said hydrocarbon-based chain being optionally substituted and/or interrupted with atoms or groups as described in the description; —$R^2$ represents a cyclic or non-cyclic, linear or branched, saturated or unsaturated hydrocarbon-based group, comprising from 3 to 30 carbon atoms; and b) one or more surfactants; it being understood that (A) is different from (B).

22 Claims, 2 Drawing Sheets

[Fig. 1] :
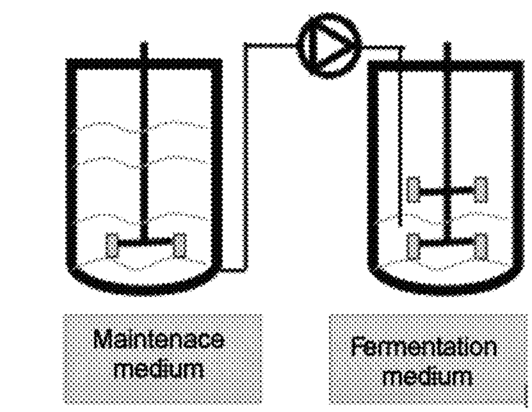
[Fig. 2] :
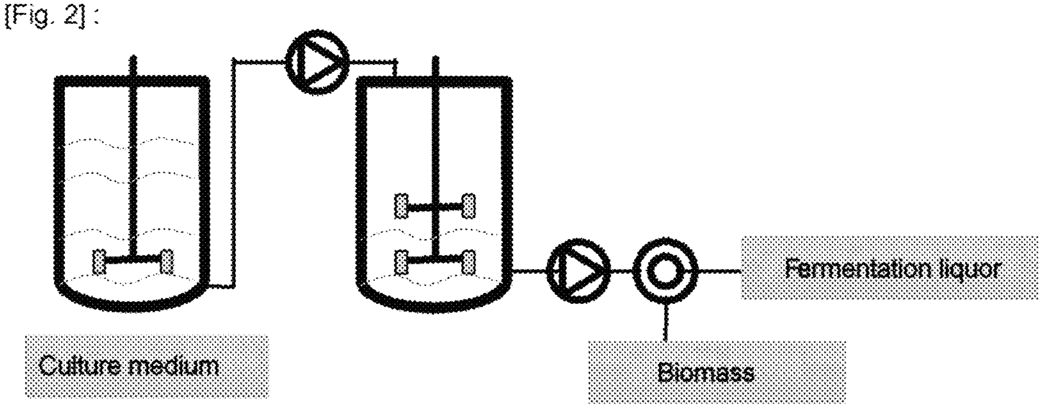

[Fig. 3]
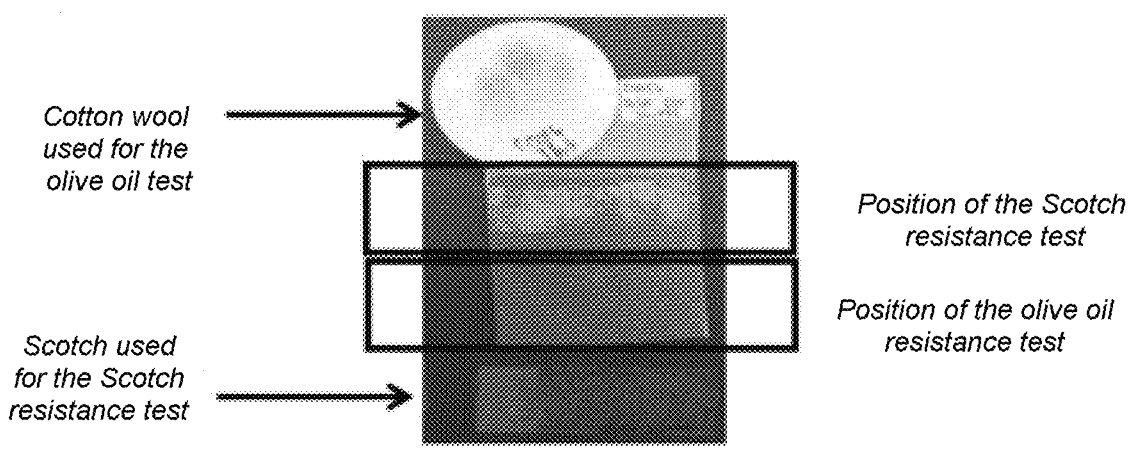
As for the olive oil and Scotch resistance tests, films are applied to a sample of BioSkin. After drying for one day, the BioSkin plate is pulled ten times by hand force. The results may then be observed on the film of formation (fragmentation or not).
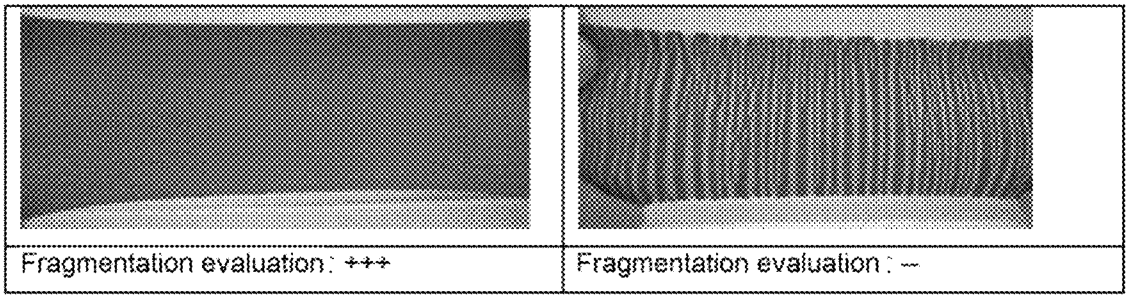

COSMETIC COMPOSITION COMPRISING A POLYHYDROXYALKANOATE COPOLYMER BEARING A(N) (UN)SATURATED HYDROCARBON-BASED CHAIN AND A SURFACTANT

The present invention relates to a cosmetic composition comprising a) at least one polyhydroxyalkanoate copolymer bearing (un)saturated hydrocarbon-based groups, b) at least one surfactant, and c) at least one fatty substance, and also to a process for treating keratin materials using such a composition.

It is known practice to use, in cosmetics, film-forming polymers which can be conveyed in organic media, such as hydrocarbon-based oils. Polymers are notably used as film-forming agents in makeup products such as mascaras, eyeliners, eyeshadows or lipsticks.

FR-A-2964663 describes a cosmetic composition comprising pigments coated with a $C_3$-$C_{21}$ polyhydroxyalkanoate, such as poly(hydroxybutyrate-co-hydroxyvalerate).

WO 2011/154508 describes a cosmetic composition comprising a 4-carboxy-2-pyrrolidinone ester derivative and a film-forming polymer which may be a polyhydroxyalkanoate, such as polyhydroxybutyrate, polyhydroxyvalerate and polyhydroxybutyrate-co-polyhydroxyvalerate.

US-A-2015/274972 describes a cosmetic composition comprising a thermoplastic resin, such as a polyhydroxyalkanoate, in aqueous dispersion and a silicone elastomer. On the other hand, WO 2018/178899 describes a cosmetic composition comprising at least one polyhydroxyalkanoate (PHA) in the form of particles with an average diameter (d50) from 0.1 μm to 100 μm, in an amount of from 0.1% by weight to 30%. by weight, with respect to the total weight of the composition. In order to absorb oily substances, such as sebum. However most PHAs are not solubilized satisfactorily in fatty substances such as volatile oil as isododecane.

The majority of the polyhydroxyalkanoate copolymers are polymers derived from the polycondensation of polymeric repeating units that are for the most part identical and derived from the same carbon source or substrate. These documents do not describe the cosmetic use of copolymers derived from polycondensation using an aliphatic substrate or first carbon source, and at least one second substrate different from the first, comprising one or more (un)saturated hydrocarbon-based groups with surfactants. There is thus a need for a composition comprising polyhydroxyalkanoate copolymers which are lipophilic or soluble in a fatty phase. Furthermore, there is a need for a composition comprising PHAs with varied functionalization or which are functionalizable with lipophilic or non-lipophilic active agents, which could make them active and soluble in a fatty phase. This makes it possible to obtain a film on keratin materials which has good cosmetic properties, notably good resistance to oils and to sebum, and also to be able to modify the gloss or the mattness.

The Applicant has discovered that polyhydroxyalkanoate copolymers bearing particular grafted or functionalized hydrocarbon-based groups, as defined below, may be readily used in fatty media, thus making it possible to obtain homogeneous compositions. Moreover, the PHA according to the invention are film forming polymers. The composition shows good stability, notably after storage for one month at room temperature (25° C.). The composition, notably after its application to keratin materials, makes it possible to obtain a film having good cosmetic properties, in particular good resistance to oils and to sebum, and also a matt or glossy appearance.

Thus, the main subject of the present invention is a composition comprising:

a) one or more polyhydroxyalkanoate (PHA) copolymers which contain, and preferably consist of, at least two different repeating polymer units chosen from the units (A) and (B) below, and also the optical or geometrical isomers thereof, the organic or mineral acid or base salts thereof, and the solvates thereof such as hydrates:

unit (A)

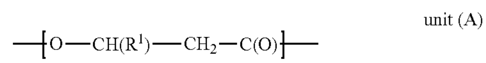

unit (B)

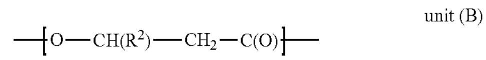

in which polymer units (A) and (B):

$R^1$ represents a hydrocarbon-based chain chosen from i) linear or branched ($C_5$-$C_{28}$)alkyl, ii) linear or branched ($C_5$-$C_{28}$)alkenyl, iii) linear or branched ($C_5$-$C_{28}$)alkynyl; preferably, the hydrocarbon-based group is linear;

said hydrocarbon-based chain being:

optionally substituted with one or more atoms or groups chosen from: a) halogen such as chlorine or bromine, b) hydroxyl, c) thiol, d) (di)($C_1$-$C_4$)(alkyl)amino, e) (thio)carboxy, f) (thio)carboxamide —C(O)—N($R_a$)$_2$ or C(S)—N($R_a$)$_2$, g) cyano, h) iso(thio)cyanate, i) (hetero)aryl such as phenyl or furyl, and j) (hetero)cycloalkyl such as anhydride, or epoxide, k) cosmetic active agent; l) R—X with R representing a group chosen from α) cycloalkyl such as cyclohexyl, β) heterocycloalkyl such as sugar, preferably monosaccharide such as glucose, γ) (hetero)aryl such as phenyl, δ) cosmetic active agent as defined previously and X representing a') O, S, N($R_a$) or Si($R_b$)($R_c$), b') S(O)$_r$, or (thio)carbonyl, c') or combinations of a') with b') such as (thio)ester, (thio)amide, (thio)urea or sulfonamide; $R_a$ representing a hydrogen atom, or a ($C_1$-$C_4$)alkyl group or an aryl($C_1$-$C_4$)alkyl group such as benzyl, preferably $R_a$ represents a hydrogen atom; $R_b$ and $R_c$, which may be identical or different, represent a ($C_1$-$C_4$)alkyl or ($C_1$-$C_4$) alkoxy group, particularly only one substituent-; preferably chosen from b) halogen, and j) such as epoxide; and/or optionally interrupted with one or more heteroatoms a') such as O, S, N($R_a$) and Si($R_b$)($R_c$), b') S(O)$_r$, (thio)carbonyl, c') or combinations of a') with b') such as (thio)ester, (thio)amide, (thio)urea, sulfonamide with r being equal to 1 or 2, $R_a$ being as defined previously, preferably $R_a$ represents a hydrogen atom, $R_b$ and $R_c$ being as defined previously;

$R^2$ represents a cyclic or non-cyclic, linear or branched, saturated or unsaturated hydrocarbon-based group comprising from 3 to 30 carbon atoms; in particular chosen from linear or branched ($C_3$-$C_{28}$)alkyl and linear or branched ($C_3$-$C_{28}$)alkenyl, in particular a linear hydrocarbon-based group, more particularly ($C_4$-$C_{20}$)alkyl or ($C_4$-$C_{20}$)alkenyl; preferably, the hydrocarbon-based group has a carbon number corresponding to the number of carbon atoms of the radical $R^1$ from which at least one carbon atom is subtracted, preferably corresponding to the number of carbon atoms of the radical $R^1$ from which two carbon atoms are subtracted; and b) one or more surfactant(s); and c) optionally one or more fatty substances, which are preferably liquid at 25° C. and at atmospheric pressure;

it being understood that (A) is different from (B).

Another subject of the invention is the use in cosmetics of a) one or more PHA copolymers as defined previously, b) one or more surfactants as defined previously, and optionally c) one or more fatty substances as defined previously.

Another subject of the invention is a process for treating keratin materials, preferably α) keratin fibres, notably human keratin fibres such as the hair, or β) human skin, in particular the lips, using a) one or more PHA copolymers as defined previously and optionally b) one or more fatty substances as defined previously.

More particularly, a subject of the invention is a non-therapeutic cosmetic process for treating keratin materials, comprising the application to the keratin materials of a composition as defined previously. The treatment process is in particular a process for caring for or making up keratin materials.

For the purposes of the present invention and unless otherwise indicated:

- the term "cosmetic active agent" means the radical of an organic or organosilicon compound which can be integrated into a cosmetic composition to give an effect on keratin materials, whether this effect is immediate or provided by repeated applications. As examples of cosmetic active agents, mention may be made of coloured or uncoloured, fluorescent or non-fluorescent chromophores such as those derived from optical brighteners, or chromophores derived from UVA and/or UVB screening agents, anti-ageing active agents or active agents intended for providing a benefit to the skin such as active agents having action on the barrier function, deodorant active agents other than mineral particles, antiperspirant active agents other than mineral particles, desquamating active agents, antioxidant active agents, moisturizing active agents, sebum-regulating active agents, active agents intended for limiting the sheen of the skin, active agents intended for combating the effects of pollution, antimicrobial or bactericidal active agents, antidandruff active agents, and fragrances.
- the term "(hetero)aryl" means aryl or heteroaryl groups;
- the term "(hetero)cycloalkyl" means cycloalkyl or heterocycloalkyl groups;
- the "aryl" or "heteroaryl" radicals or the aryl or heteroaryl part of a radical may be substituted with at least one substituent borne by a carbon atom, chosen from:
  - a $C_1$-$C_6$ and preferably $C_1$-$C_4$ alkyl radical;
  - a halogen atom such as chlorine, fluorine or bromine;
  - a hydroxyl group;
  - a $C_1$-$C_2$ alkoxy radical; a $C_2$-$C_4$ (poly)hydroxyalkoxy radical;
  - an amino radical;
  - an amino radical substituted with one or two identical or different $C_1$-$C_6$, $C_1$-$C_6$ and preferably $C_1$-$C_4$ alkyl radicals;
  - an acylamino radical (—NR—COR') in which the radical R is a hydrogen atom;
  - a $C_1$-$C_4$ alkyl radical and the radical R' is a $C_1$-$C_4$ alkyl radical; a carbamoyl radical ($(R)_2N$—CO—) in which the radicals R, which may be identical or different, represent a hydrogen atom or a $C_1$-$C_4$ alkyl radical;
  - an alkylsulfonylamino radical ($R'SO_2$—NR—) in which the radical R represents a hydrogen atom or a $C_1$-$C_4$ alkyl radical and the radical R' represents a $C_1$-$C_4$ alkyl radical, or a phenyl radical;
  - an aminosulfonyl radical ($(R)_2N$—$S(O)_2$—) in which the radicals R, which may be identical or different, represent a hydrogen atom or a $C_1$-$C_4$ alkyl radical;
  - a carboxyl radical in the acid or salified form (preferably salified with an alkali metal or a substituted or unsubstituted ammonium);
  - a cyano group (CN);
  - a polyhalo($C_1$-$C_4$)alkyl group, preferentially trifluoromethyl ($CF_3$);
- the cyclic or heterocyclic part of a non-aromatic radical may be substituted with at least one substituent borne by a carbon atom, chosen from the groups:
  - hydroxyl,
  - $C_1$-$C_4$ alkoxy, $C_2$-$C_4$ (poly)hydroxyalkoxy,
  - alkylcarbonylamino (RCO—NR'—), in which the radical R' is a hydrogen atom or a $C_1$-$C_4$ alkyl radical and the radical R is a $C_1$-$C_2$ alkyl radical or an amino radical substituted with one or two identical or different $C_1$-$C_4$ alkyl groups;
  - alkylcarbonyloxy (RCO—O—), in which the radical R is a $C_1$-$C_4$ alkyl radical or an amino radical substituted with one or two identical or different $C_1$-$C_4$ alkyl groups;
  - alkoxycarbonyl ((RO—CO—) in which the radical R is a $C_1$-$C_4$ alkyl radical or an amino radical substituted with one or two identical or different $C_1$-$C_4$ alkyl groups;
- a cyclic or heterocyclic radical, or a non-aromatic part of an aryl or heteroaryl radical, may also be substituted with one or more oxo groups;
- a hydrocarbon-based chain is unsaturated when it includes one or more double bonds and/or one or more triple bonds;
- an "aryl" radical represents a monocyclic or fused or non-fused polycyclic hydrocarbon-based group comprising from 6 to 22 carbon atoms, and in which at least one ring is aromatic; preferentially, the aryl radical is a phenyl, biphenyl, naphthyl, indenyl, anthracenyl or tetrahydronaphthyl;
- a "heteroaryl" radical represents a monocyclic or fused or non-fused polycyclic, 5- to 22-membered group, comprising from 1 to 6 heteroatoms chosen from nitrogen, oxygen, sulfur and selenium atoms, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl and xanthylyl;
- a "cyclic" or "cycloalkyl" radical is a monocyclic or fused or non-fused polycyclic, non-aromatic cyclic hydrocarbon-based radical containing from 5 to 22 carbon atoms, which may include one or more unsaturations; the cycloalkyl is preferably a cyclohexyl group;
- a "heterocyclic" or "heterocycloalkyl" radical is a monocyclic or fused or non-fused polycyclic 3- to 9-membered non-aromatic cyclic radical, including from 1 to 4 heteroatoms chosen from nitrogen, oxygen, sulfur and selenium atoms; preferably, the heterocycloalkyl is chosen from epoxide, piperazinyl, piperidyl and morpholinyl;

- an "alkyl" radical is a linear or branched, in particular $C_1$-$C_6$ and preferably $C_1$-$C_4$ saturated hydrocarbon-based radical;
- an "alkenyl" radical is a linear or branched unsaturated hydrocarbon-based radical comprising one or more conjugated or non-conjugated double bonds;
- an "alkynyl" radical is a linear or branched unsaturated hydrocarbon-based radical comprising one or more conjugated or non-conjugated triple bonds;
- an "alkoxy radical" is an alkyl-oxy radical for which the alkyl radical is a linear or branched $C_1$-$C_6$ and preferentially $C_1$-$C_4$ hydrocarbon-based radical;
- a "sugar" radical is a monosaccharide or polysaccharide radical, and the O-protected sugar derivatives thereof such as sugar esters of $(C_1$-$C_6)$alkylcarboxylic acids such as sugar esters of acetic acid, sugars containing amine group(s) and $(C_1$-$C_4)$alkyl derivatives, such as methyl derivatives, for instance methylglucose. Sugar radicals that may be mentioned include: sucrose, glucose, galactose, ribose, fucose, maltose, fructose, mannose, arabinose, xylose, lactose;
- the term "monosaccharide" refers to a monosaccharide sugar comprising at least 5 carbon atoms of formula $C_x(H_2O)_x$ with x an integer greater than or equal to 5, preferably x is greater than or equal to 6, in particular x is between 5 and 7 inclusive, preferably x=6, they may be of D or L configuration, and of alpha or beta anomer, and also the salts thereof and the solvates thereof such as hydrates;
- the term "polysaccharide" refers to a polysaccharide sugar which is a polymer constituted of several saccharides bonded together via O-oside bonds, said polymers being constituted of monosaccharide units as defined previously, said monosaccharide units comprising at least 5 carbon atoms, preferably 6; in particular, the monosaccharide units are linked together via a 1,4 or 1,6 bond as α (alpha) or β (beta) anomer, it being possible for each oside unit to be of L or D configuration, and also the salts thereof and the solvates thereof such as the hydrates of said monosaccharides; more particularly, they are polymers formed from a certain number of saccharides (or monosaccharides) having the general formula: $—[C_x(H_2O)_y)]_w—$ where x is an integer greater than or equal to 5, preferably x is greater than or equal to 6, in particular x is between 5 and 7 inclusive and preferably x=6, and y is an integer which represents x−1, and w is an integer greater than or equal to 2, particularly of between 3 and 3000 inclusive, more particularly between 5 and 2500 and preferentially between 10 and 2300;
- the term "sugar bearing amine group(s)" means that the sugar radical is substituted with one or more amino groups $NR_1R_2$ i.e. at least one of the hydroxyl groups of at least one saccharide unit of the sugar radical is replaced with a group $NR_1R_2$ with $R_1$ and $R_2$, which may be identical or different, representing i) a hydrogen atom, ii) a $(C_1$-$C_6)$alkyl group, iii) an aryl group such as phenyl, iv) an aryl$(C_1$-$C_4)$alkyl group such as benzyl, vii) $—C(Y)—(Y')_f—R'_1$, with Y and Y', which may be identical or different, representing an oxygen atom, a sulfur atom or $N(R'_2)$, preferably oxygen, f=0 or 1, preferably 0; and $R'_1$, and $R'_2$ representing i) to vi) of $R_1$ and $R_2$ defined previously, and in particular $R'_1$, denoting a $(C_1$-$C_6)$alkyl group such as methyl. Preferably, $R_1$ and $R_2$ represent a hydrogen atom or a $(C_1$-$C_4)$alkylcarbonyl group such as acetyl;
- the term "organic or mineral acid salt" more particularly means organic or mineral acid salts in particular chosen from a salt derived from i) hydrochloric acid HCl, ii) hydrobromic acid HBr, iii) sulfuric acid $H_2SO_4$, iv) alkylsulfonic acids: Alk-$S(O)_2OH$ such as methylsulfonic acid and ethylsulfonic acid; v) arylsulfonic acids: Ar—$S(O)_2OH$ such as benzenesulfonic acid and toluenesulfonic acid; vi) alkoxysulfinic acids: Alk-O—S(O)OH such as methoxysulfinic acid and ethoxysulfinic acid; vii) aryloxysulfinic acids such as tolueneoxysulfinic acid and phenoxysulfinic acid; viii) phosphoric acid $H_3PO_4$; ix) triflic acid $CF_3SO_3H$ and x) tetrafluoroboric acid $HBF_4$; xi) organic carboxylic acids R°—C(O)—OH (I'z), in which formula (I'z) R° represents a (hetero)aryl group such as phenyl, (hetero)aryl$(C_1$-$C_4)$alkyl group such as benzyl, or $(C_1$-$C_{10})$alkyl, said alkyl group being optionally substituted preferably with one or more hydroxyl groups or amino or carboxyl radicals, R° preferably denoting a $(C_1$-$C_6)$alkyl group optionally substituted with 1, 2 or 3 hydroxyl or carboxyl groups; more preferentially, the monocarboxylic acids of formula (I'z) are chosen from acetic acid, glycolic acid, lactic acid, and mixtures thereof, and more particularly from acetic acid and lactic acid; and the polycarboxylic acids are chosen from tartaric acid, succinic acid, fumaric acid, citric acid and mixtures thereof; and xii) amino acids including more carboxylic acid radicals than amino groups, such as γ-carboxyglutamic acid, aspartic acid or glutamic acid, in particular γ-carboxyglutamic acid;
- an "anionic counterion" is an anion or an anionic group associated with the cationic charge; more particularly, the anionic counterion is chosen from: i) halides such as chloride or bromide; ii) nitrates; iii) sulfonates, including $C_1$-$C_6$ alkylsulfonates: Alk-$S(O)_2O$— such as methanesulfonate or mesylate and ethanesulfonate; iv) arylsulfonates: Ar—$S(O)_2O$— such as benzenesulfonate and toluenesulfonate or tosylate; v) citrate; vi) succinate; vii) tartrate; viii) lactate; ix) alkyl sulfates: Alk-O—S(O)O— such as methyl sulfate and ethyl sulfate; x) aryl sulfates: Ar—O—S(O)O— such as benzene sulfate and toluene sulfate; xi) alkoxy sulfates: Alk-O—$S(O)_2O$— such as methoxy sulfate and ethoxy sulfate; xii) aryloxy sulfates: Ar—O—S$(O)_2$ O—; xiii) phosphate; xiv) acetate; xv) triflate; and xvi) borates such as tetrafluoroborate.
- the "solvates" represent hydrates and also the combination with linear or branched $C_1$-$C_4$ alcohols such as ethanol, isopropanol or n-propanol.
- the term "chromophore" means a radical derived from a colourless or coloured compound that is capable of absorbing in the UV and/or visible radiation range at a wavelength $\lambda_{abs}$ of between 250 and 800 nm. Preferably, the chromophore is coloured, i.e. it absorbs wavelengths in the visible range, i.e. preferably between 400 and 800 nm. Preferably, the chromophores appear coloured to the eye, particularly between 400 and 700 nm (*Ullmann's Encyclopedia,* 2005, Wiley-VcH, Verlag "Dyes, General Survey", § 2.1 Basic Principle of Color);
- the term "fluorescent chromophore" means a chromophore which is also capable of re-emitting in the visible range at an emission wavelength $\lambda_{em}$ of between 400 and 800 nm, and higher than the absorption wavelength, preferably with a Stoke's shift, i.e. the difference between the maximum absorption wavelength and the emission wavelength is at least 10 nm. Preferably, fluorescent chromophores are derived from fluorescent dyes that are capable of absorbing in the visible range $\lambda_{abs}$, i.e. at a wavelength of between 400 and 800 nm, and of re-emitting in the visible range $\lambda_{em}$ between 400 and 800 nm. More preferentially, fluorescent chromophores are capable of absorbing at a $\lambda_{abs}$ of between 420 and 550 nm and of re-emitting in the visible range $\lambda_{em}$ between 470 and 600 nm;
- the term "optical brightening chromophore" means a chromophore derived from an optical brightening compound or "optical brighteners, optical brightening agents (OBAs)" or "fluorescent brightening agents (FBAs)" or "fluorescent whitening agents (FWAs)", i.e. agents which absorb UV radiation, i.e. at a wavelength $\lambda_{abs}$ of between 250 and 350 nm, and of subsequently re-emitting this energy by fluorescence in the visible range at an emission wavelength $\lambda_{em}$ of between 400 and 600 nm, i.e. wavelengths between blue-violet and blue-green with a maximum in the blue range. Optical brightening chromophores are thus colourless to the eye;

the term "UV-A screening agent" means a chromophore derived from a compound which screens out (or absorbs) UV-A ultraviolet rays at a wavelength of between 320 and 400 nm. A distinction may be made between short UV-A screening agents (which absorb rays at a wavelength of between 320 and 340 nm) and long UV-A screening agents (which absorb rays at a wavelength of between 340 and 400 nm);

the term "UV-B screening agent" means a chromophore derived from a compound which screens out (or absorbs) UV-B ultraviolet rays at a wavelength of between 280 and 320 nm.

Furthermore, unless otherwise indicated, the limits delimiting the extent of a range of values are included in that range of values.

a) The PHA Copolymer(s)

The composition of the invention comprises as first ingredient a) one or more PHA copolymers which contain, or preferably consist of, at least two different repeating polymer units chosen from the units (A) and (B) as defined previously.

The term "copolymer" means that said polymer is derived from the polycondensation of repeating polymer units that are different from each other, i.e. said polymer is derived from the polycondensation of repeating polymer units (A) with (B), it being understood that the polymer units (A) are different from the polymer units (B), and derived from polycondensation starting with an aliphatic substrate or first carbon source, and with at least one second substrate different from the first, comprising one or more (un)saturated hydrocarbon-based groups.

According to a particular embodiment of the invention, the PHA copolymer(s) consist of two different repeating polymer units chosen from the units (A) and (B) as defined previously.

More particularly, the PHA copolymer(s) according to the invention comprise the repeating unit of formula (I), and also the optical or geometrical isomers thereof, the organic or mineral acid or base salts thereof, and the solvates thereof such as hydrates:

[Chem. 1]

(I)

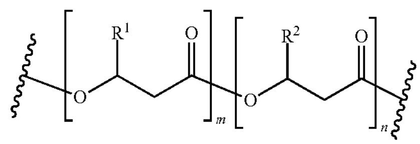

in which formula (I):

$R^1$ and $R^2$ are as defined previously, m and n are integers greater than or equal to 1; preferably, the sum n+m is inclusively between 450 and 1400;

preferably, m>n when $R^1$ and $R^2$ represent an unsubstituted and uninterrupted alkyl group—more preferentially, when $R^1$ and $R^2$ are linear alkyl, then $R^1$ is a $C_5$-$C_{13}$ alkyl group; and $R^2$ represents a linear alkyl group with a carbon number corresponding to the carbon number of $R^1$ from which two carbon atoms are subtracted such as a $C_3$-$C_{11}$ alkyl group; and preferably, m<n when $R^1$ represents a substituted and/or interrupted alkyl group, an optionally substituted and/or interrupted alkenyl group or an optionally substituted and/or interrupted alkynyl group, and $R^2$ represents an alkyl group.

According to a particular embodiment, the PHA copolymer(s) of composition a) contain three different repeating polymer units (A), (B) and (C), and preferably consist of three different polymer units (A), (B) and (C) below, and also the optical or geometrical isomers thereof and the solvates thereof such as hydrates:

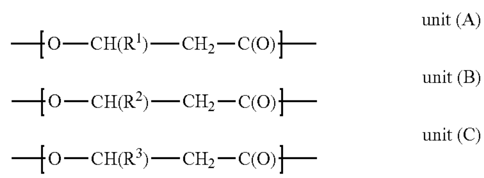

in which polymer units (A), (B) and (C):

$R^1$ and $R^2$ are as defined previously;

$R^3$ represents a cyclic or non-cyclic, linear or branched, saturated or unsaturated hydrocarbon-based group comprising from 1 to 30 carbon atoms, and in particular represents a hydrocarbon-based group chosen from linear or branched ($C_1$-$C_{28}$)alkyl and linear or branched ($C_2$-$C_{28}$)alkenyl, in particular a linear hydrocarbon-based group, more particularly ($C_4$-$C_{20}$)alkenyl; preferably, the hydrocarbon-based group has a carbon number corresponding to the number of carbon atoms of the radical $R^1$, or else corresponding to the number of carbon atoms of the radical $R^1$ from which at least three carbon atoms are subtracted, preferably corresponding to the number of carbon atoms of the radical $R^1$ from which four carbon atoms are subtracted; and it being understood that:

(A) is different from (B) and (C), (B) is different from (A) and (C), and (C) is different from (A) and (B); and preferably, when $R^1$, $R^2$ and $R^3$ represent an unsubstituted and uninterrupted alkyl group, the molar percentage of units (A) is greater than the molar percentage of units (B), and greater than the molar percentage of units (C)—more preferentially, when $R^1$, $R^2$ and $R^3$ are linear alkyl, then $R^1$ is a $C_5$-$C_{13}$ alkyl group; and $R^2$ represents a linear alkyl group with a carbon number corresponding to the carbon number of $R^1$ from which two carbon atoms are subtracted, and $R^3$ represents a linear alkyl group with a carbon number corresponding to the carbon number of $R^1$ from which four carbon atoms are subtracted; and preferably, when $R^1$ represents a substituted and/or interrupted alkyl, optionally substituted and/or optionally interrupted alkenyl or optionally substituted and/or optionally interrupted alkynyl group, then the molar percentage of units (A) is less than the molar percentage of units (B) and less than the molar percentage of units (C) notably if $R^2$ represents an alkyl group and/or $R^3$ represents an alkyl group.

According to a particular embodiment of the invention, the PHA copolymer(s) comprise the repeating unit of formula (II), and also the optical or geometrical isomers thereof, the organic or mineral acid or base salts thereof, and the solvates thereof such as hydrates:

[Chem. 2]

(II)

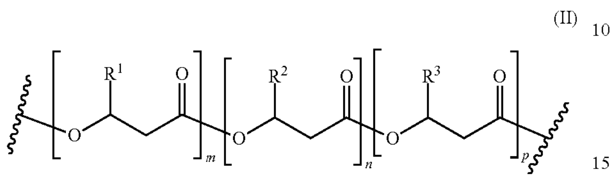

in which formula (II):

$R^1$, $R^2$ and $R^3$ are as defined previously;

m, n and p are integers greater than or equal to 1; preferably, the sum n+m+p is inclusively between 450 and 1400; and preferably, m>n+p when $R^1$, $R^2$ and $R^3$ represent an unsubstituted and uninterrupted alkyl group—more preferentially, when $R^1$, $R^2$ and $R^3$ are linear alkyl, then $R^1$ is a $C_5$-$C_{13}$ alkyl group; and $R^2$ represents a linear alkyl group with a carbon number corresponding to the carbon number of $R^1$ from which two carbon atoms are subtracted such as a $C_3$-$C_{11}$ alkyl group, and $R^3$ represents a linear alkyl group with a carbon number corresponding to the carbon number of $R^1$ from which four carbon atoms are subtracted such as a $C_1$-$C_9$ alkyl group; and preferably, m<n+p when $R^1$ represents a substituted and/or interrupted alkyl group, an optionally substituted and/or optionally interrupted alkenyl group or an optionally substituted and/or optionally interrupted alkynyl group, and $R^2$ and $R^3$ represent an alkyl group.

According to a particular embodiment, the PHA copolymer(s) of composition a) contain four different repeating polymer units (A), (B), (C) and (D), and preferably consist of four different polymer units (A), (B), (C) and (D), below, and also the optical or geometrical isomers thereof, the organic or mineral acid or base salts thereof, and the solvates thereof such as hydrates:

unit (A)

unit (B)

unit (C)

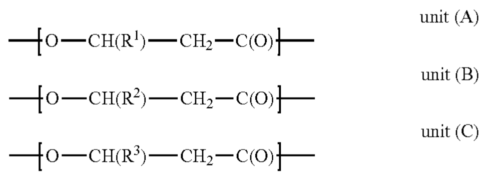

-continued unit (D)

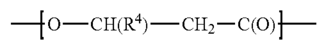

in which polymer units (A), (B), (C) and (D):

$R^1$, $R^2$ and $R^3$ are as defined previously;

$R^4$ represents a cyclic or non-cyclic, linear or branched, saturated hydrocarbon-based group comprising from 3 to 30 carbon atoms optionally substituted with one or more atoms or groups a) to l) and/or optionally interrupted with one or more heteroatoms or groups a') to c') as defined for $R^1$; it in particular represents a hydrocarbon-based group chosen from linear or branched ($C_4$-$C_{28}$)alkyl optionally substituted with one or more atoms or groups a) to l) and/or interrupted with one or more heteroatoms or groups a') to c') as defined for $R^1$; and it being understood that:

(A) is different from (B), (C) and (D), (B) is different from (A), (C) and (D), (C) is different from (A), (B) and (D), and (D) is different from (A), (B) and (C); and preferably, when $R^1$, $R^2$, $R^3$ and $R^4$ represent an unsubstituted and uninterrupted alkyl group, the molar percentage of units (A) is greater than the molar percentage of units (B), greater than the molar percentage of units (C), and greater than the molar percentage of units (D)—more preferentially, when $R^1$, $R^2$, $R^3$ and $R^4$ are linear alkyl, then $R^1$ is a $C_5$-$C_{13}$ alkyl group; and $R^2$ represents a linear alkyl group with a carbon number corresponding to the carbon number of $R^1$ from which two carbon atoms are subtracted such as a $C_3$-$C_{11}$ alkyl group, $R^3$ represents a linear alkyl group with a carbon number corresponding to the carbon number of $R^1$ from which four carbon atoms are subtracted such as a $C_1$-$C_9$ alkyl group, and $R^4$ represents a linear alkyl group with a carbon number corresponding to the carbon number of $R^1$ from which six carbon atoms are subtracted; and preferably, when $R^1$ represents a substituted and/or interrupted alkyl, optionally substituted and/or optionally interrupted alkenyl or optionally substituted and/or optionally interrupted alkynyl group, then the molar percentage of units (A) is less than the molar percentage of units (B) and less than the molar percentage of units (C), notably if $R^2$ represents an alkyl group and/or $R^3$ represents an alkyl group; and $R^4$ represents an optionally substituted and/or optionally interrupted alkyl, optionally substituted and/or optionally interrupted alkenyl or optionally substituted and/or optionally interrupted alkynyl group.

According to a particular embodiment of the invention, the PHA copolymer(s) comprise the repeating unit of formula (III), and also the optical or geometrical isomers thereof, the organic or mineral acid or base salts thereof, and the solvates thereof such as hydrates:

[Chem 3]

(III)

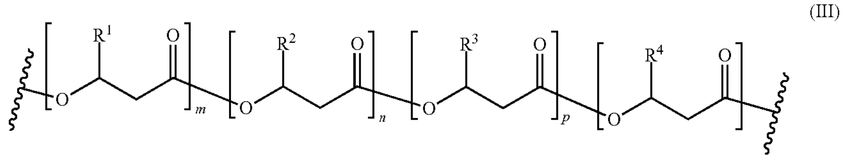

in which formula (III):

$R^1$, $R^2$, $R^3$ and $R^4$ are as defined previously;

m, n, p and v are integers greater than or equal to 1;

preferably, the sum n+m+p+v is inclusively between 450 and 1400; and preferably, when $R^1$, $R^2$, $R^3$ and $R^4$ represent an unsubstituted and uninterrupted alkyl group, then m>n+p+q—more preferentially, when $R^1$, $R^2$, $R^3$ and $R^4$ are linear alkyl, then $R^1$ is a $C_5$-$C_{13}$ alkyl group; and $R^2$ represents a linear alkyl group with a carbon number corresponding to the carbon number of $R^1$ from which two carbon atoms are subtracted, $R^3$ represents a linear alkyl group with a carbon number corresponding to the carbon number of $R^1$ from which four carbon atoms are subtracted, and $R^4$ represents a linear alkyl group with a carbon number corresponding to the carbon number of $R^1$ from which six carbon atoms are subtracted; and preferably, when $R^1$ represents a substituted and/or interrupted alkyl, optionally substituted and/or optionally interrupted alkenyl or optionally substituted and/or optionally interrupted alkynyl group, and $R^2$ and $R^3$ represent an alkyl group, and $R^4$ represents a substituted and/or interrupted alkyl, optionally substituted and/or optionally interrupted alkenyl or optionally substituted and/or optionally interrupted alkynyl group, then n>m+v; more preferentially n+p>m+v.

According to a more particular embodiment, the PHA copolymer(s) of composition a) contain five different repeating polymer units (A), (B), (C), (D) and (E), and preferably consist of five different polymer units (A), (B), (C), (D) and (E), below, and also the optical or geometrical isomers thereof, the organic or mineral acid or base salts thereof, and also the solvates thereof such as hydrates:

unit (A)

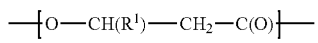

unit (B)

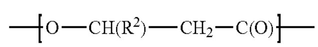

unit (C)

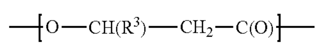

unit (D)

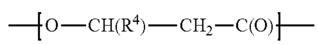

unit (E)

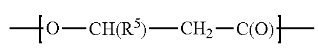

in which polymer units (A), (B), (C), (D) and (E):

$R^1$, $R^2$, $R^3$ and $R^4$ are as defined previously; and $R^5$ represents a cyclic or non-cyclic, linear or branched, saturated hydrocarbon-based group comprising from 3 to 30 carbon atoms optionally substituted with one or more atoms or groups a) to l) and/or optionally interrupted with one or more heteroatoms or groups a') to c') as defined for $R^1$; it in particular represents a hydrocarbon-based group chosen from linear or branched ($C_4$-$C_{28}$)alkyl optionally substituted with one or more atoms or groups a) to l) and/or interrupted with one or more heteroatoms or groups a') to c') as defined for $R^1$; preferably, the hydrocarbon-based group has a carbon number corresponding to the number of carbon atoms of the radical $R^4$ from which at least one carbon atom is subtracted, preferably corresponding to the number of carbon atoms of the radical $R^4$ from which at least two carbon atoms are subtracted, preferably from which two carbon atoms are subtracted;

it being understood that:

(A) is different from (B), (C), (D) and (E); (B) is different from (A), (C), (D) and (E); (C) is different from (A), (B), (D) and (E); (D) is different from (A), (B), (C) and (E); and (E) is different from (A), (B), (C) and (D); and preferably, when $R^1$, $R^2$, $R^3$, $R^4$ and $R^5$ represent an unsubstituted and uninterrupted alkyl group, the molar percentage of units (A) is greater than the molar percentage of units (B), greater than the molar percentage of units (C), greater than the molar percentage of units (D) and greater than the molar percentage of units (E)—more preferentially, when $R^1$, $R^2$, $R^3$, $R^4$ and $R^5$ are linear alkyl, then $R^1$ is a $C_5$-$C_{13}$ alkyl group; and $R^2$ represents a linear alkyl group with a carbon number corresponding to the carbon number of $R^1$ from which two carbon atoms are subtracted, $R^3$ represents a linear alkyl group with a carbon number corresponding to the carbon number of $R^1$ from which four carbon atoms are subtracted, $R^4$ represents a linear alkyl group with a carbon number corresponding to the carbon number of $R^1$ from which six carbon atoms are subtracted, and $R^5$ represents a linear alkyl group with a carbon number corresponding to the carbon number of $R^1$ from which eight carbon atoms are subtracted; and preferably, when $R^1$ represents a substituted and/or interrupted alkyl, optionally substituted and/or optionally interrupted alkenyl or optionally substituted and/or optionally interrupted alkynyl group, then the molar percentage of units (A) is less than the molar percentage of units (B) and less than the molar percentage of units (C) notably if $R^2$ represents an alkyl group and/or $R^3$ represents an alkyl group, and $R^4$ and $R^5$ represent a substituted and/or interrupted alkyl, optionally substituted and/or optionally interrupted alkenyl or optionally substituted and/or optionally interrupted alkynyl group.

According to a particular embodiment of the invention, the PHA copolymer(s) comprise the repeating unit of formula (IV), and also the optical or geometrical isomers thereof, the organic or mineral acid or base salts thereof, and the solvates thereof such as hydrates:

[Chem. 4]

(IV)

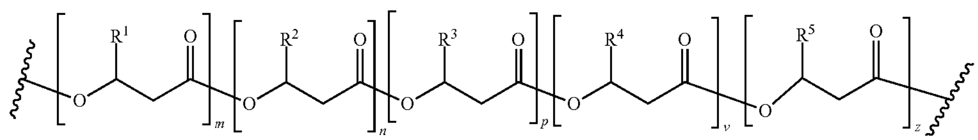

in which formula (IV):

$R^1$, $R^2$, $R^3$, $R^4$ and $R^5$ are as defined previously;

m, n, p, v and z are integers greater than or equal to 1; preferably, the sum n+m+p+v+z is inclusively between 450 and 1400; and preferably, when $R^1$, $R^2$, $R^3$, $R^4$ and $R^5$ represent an unsubstituted and uninterrupted alkyl group, then m>n+p+v+z;

preferably, when $R^1$ represents a substituted and/or interrupted alkyl, optionally substituted and/or optionally interrupted alkenyl or optionally substituted and/or optionally interrupted alkynyl group, $R^2$ and $R^3$ represent an alkyl group, and the groups $R^4$ and $R^5$ represent a substituted and/or interrupted alkyl, optionally substituted and/or optionally interrupted alkenyl or optionally substituted and/or optionally interrupted alkynyl group, then n>m+v+z; more preferentially n+p>m+v+z.

Preferably, $R^1$ represents a linear or branched, preferably linear, ($C_5$-$C_{28}$)alkyl hydrocarbon-based chain. According to one embodiment of the composition according to the invention, the PHA copolymer(s) are such that the radical $R^1$ is an alkyl group comprising 5 to 14 and preferably between 6 and 12 carbon atoms, more preferentially between 7 and 10 carbon atoms such as n-pentyl, n-hexyl, n-octyl or n-nonyl.

According to a particular embodiment of the invention, the hydrocarbon-based chain $R^1$ is unsubstituted. According to a particular embodiment of the invention, the hydrocarbon-based chain $R^1$ is uninterrupted.

According to another embodiment, the hydrocarbon-based chain of the radical R' of the invention is 1) either substituted, 2) or interrupted, 3) or substituted and interrupted.

According to a particular embodiment of the invention, the PHA copolymer(s) are such that $R^1$ represents a hydrocarbon-based chain, notably an alkyl group as defined previously, which is interrupted with one or more (preferably one) atoms or groups chosen from O, S, N($R_a$) and carbonyl, or combinations thereof such as ester, amide or urea, with $R_a$ being as defined previously, preferably $R_a$ represents a hydrogen atom; preferably, $R^1$ represents an alkyl group which is interrupted with one or more atoms chosen from O and S, more preferentially with an O or S, notably S, atom. In particular, when it represents an interrupted hydrocarbon-based chain, notably alkyl, $R^1$ is $C_7$-$C_{20}$, more particularly $C_8$-$C_{18}$ and even more particularly $C_9$-$C_{16}$. Preferably, said interrupted hydrocarbon-based chain, notably alkyl, is linear.

According to another embodiment of the invention, the PHA copolymer(s) are such that $R^1$ represents a hydrocarbon-based chain, notably an alkyl group as defined previously, substituted with one or more (preferably one) atoms or groups chosen from: a) to k) as defined previously. Preferably, said hydrocarbon-based chain is substituted with only one atom or group chosen from: a) to k) as defined previously.

According to a particular embodiment of the invention, the PHA copolymer(s) are such that $R^1$ represents a hydrocarbon-based chain, notably an alkyl group as defined previously, which is substituted with one or more (preferably one) groups chosen from b) hydroxyl, c) thiol, d) (di)($C_1$-$C_4$)(alkyl)amino and preferably amino, e) carboxyl, i) (hetero)cycloalkyl such as anhydride, or epoxide, j) a cosmetic active agent chosen from coloured or uncoloured, fluorescent or non-fluorescent chromophores such as optical brighteners, UV-screening agents, h) (hetero)aryl such as phenyl or furyl, k) R—X with R representing a group chosen from α) cycloalkyl such as cyclohexyl, β) heterocycloalkyl such as a sugar radical, preferably a monosaccharide such as glucosyl, γ) (hetero)aryl such as phenyl, δ) a cosmetic active agent as defined previously and X representing a') O, S, N($R_a$), b') carbonyl, c') or combinations thereof of a') with b') such as ester, amide or urea; $R_a$ represents a hydrogen atom or a ($C_1$-$C_4$)alkyl or aryl($C_1$-$C_4$)alkyl group such as benzyl, preferably $R_a$ represents a hydrogen atom.

Even more preferentially, the PHA copolymer(s) are such that $R^1$ represents a hydrocarbon-based chain, notably an alkyl group as defined previously, which is substituted with one or more (preferably one) groups chosen from b) hydroxyl, d) (di)($C_1$-$C_4$)(alkyl)amino, preferably amino, e) carboxyl, i) (hetero)cycloalkyl such as epoxide, h) (hetero)aryl such as phenyl or furyl, k) R—X with R representing a group chosen from α) cycloalkyl such as cyclohexyl, β) heterocycloalkyl such as a sugar radical, preferably a monosaccharide such as glucosyl, γ) (hetero)aryl such as phenyl, and X representing a') O, S or N($R_a$), preferably S; $R_a$ representing a hydrogen atom or a ($C_1$-$C_4$)alkyl group, preferably $R_a$ represents a hydrogen atom.

Preferably, said substituted hydrocarbon-based chain, notably alkyl, is linear.

According to another particular embodiment of the invention, the hydrocarbon-based chain of the radical R1 of the invention is substituted and interrupted.

According to a particular embodiment of the invention, the hydrocarbon-based chain (notably an alkyl group as defined previously) of the radical $R^1$ of the invention is:

substituted with one or more (preferably one) groups chosen from b) hydroxyl, c) thiol, d) (di)($C_1$-$C_4$)(alkyl)amino and preferably amino, e) carboxyl, i) (hetero)cycloalkyl such as anhydride, or epoxide, j) a cosmetic active agent chosen from coloured or uncoloured, fluorescent or non-fluorescent chromophores such as optical brighteners, UV-screening agents, h) (hetero)aryl such as phenyl or furyl, k) R—X with R representing a group chosen from α) cycloalkyl such as cyclohexyl, β) heterocycloalkyl such as a sugar, preferably a monosaccharide such as glucose, γ) (hetero)aryl such as phenyl, δ) a cosmetic active agent as defined previously and X representing a') O, S, N($R_a$), b') carbonyl, c') or combinations thereof of a') with b') such as ester, amide or urea; $R_a$ representing a hydrogen atom or a ($C_1$-$C_4$)alkyl or aryl($C_1$-$C_4$)alkyl group such as benzyl, preferably $R_a$ represents a hydrogen atom; and interrupted with one or more (preferably one) atoms or groups chosen from O, S, N($R_a$) and carbonyl, or combinations thereof such as ester, amide or urea, with $R_a$ being as defined previously, preferably $R_a$ represents a hydrogen atom; preferably an alkyl group which is interrupted with one or more atoms chosen from O and S, more preferentially with an O or S, notably S, atom. In particular, when it represents an interrupted hydrocarbon-based chain, notably alkyl, $R^1$ is $C_7$-$C_{20}$, more particularly $C_8$-$C_{18}$ and even more particularly $C_9$-$C_{16}$.

According to a preferred embodiment of the invention, the hydrocarbon-based chain (notably an alkyl group as defined previously) of the radical $R^1$ of the invention is:

substituted with one or more (preferably one) groups chosen from b) hydroxyl, d) (di)($C_1$-$C_4$)(alkyl)amino, preferably amino, e) carboxyl, i) (hetero)cycloalkyl such as epoxide, h) (hetero)aryl such as phenyl or furyl, k) R—X with R representing a group chosen from α) cycloalkyl such as cyclohexyl, β) heterocycloalkyl such as a sugar, preferably a monosaccharide such as glucose, γ) (hetero)aryl such as phenyl, and X representing a') O, S or $N(R_a)$, preferably S; $R_a$ representing a hydrogen atom or a $(C_1-C_4)$alkyl group, preferably $R_a$ represents a hydrogen atom; and interrupted with one or more (preferably one) atoms or groups chosen from O, S, $N(R_a)$ and carbonyl, or combinations thereof such as ester, amide or urea, with $R_a$ being as defined previously, preferably $R_a$ represents a hydrogen atom; preferably an alkyl group which is interrupted with one or more atoms chosen from O and S, more preferentially with an O or S, notably S, atom. In particular, when it represents an interrupted hydrocarbon-based chain, notably alkyl, $R^1$ is $C_7$-$C_{20}$, more particularly $C_8$-$C_{18}$ and even more particularly $C_9$-$C_{16}$.

Preferably, said substituted and interrupted hydrocarbon-based chain is notably alkyl, and is preferably linear.

More preferentially, when said hydrocarbon-based chain $R^1$ is substituted, it is substituted at the end of the chain on the opposite side from the carbon atom which bears said radical $R^1$.

According to one embodiment of the invention, said hydrocarbon-based chain $R^1$ has the following formula $-(CH_2)_r X-(ALK)_u-G$ with X being as defined previously, in particular representing O, S or $N(R_a)$, preferably S, ALK represents a linear or branched, preferably linear, $(C_1-C_{10})$ alkylene and more particularly $(C_1-C_3)$alkylene chain, r represents an integer inclusively between 6 and 11, preferably between 7 and 10 such as 8; u is equal to 0 or 1; and G represents a hydrogen atom or a group chosen from hydroxyl, carboxyl, (di)$(C_1-C_4)$(alkyl)amino, (hetero)aryl in particular aryl such as phenyl, cycloalkyl such as cyclohexyl, or a sugar, in particular a monosaccharide optionally protected with one or more groups such as acyl, preferably Sug

[Chem. 4]

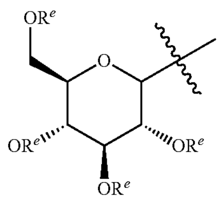

with $R^e$ representing a group $R^f$-c(O)-, with $R^f$ representing a $(C_1-C_4)$ alkyl group such as methyl. Preferably, when u is equal to 0, G represents a cycloalkyl such as cyclohexyl or a sugar as defined previously. According to another advantageous variant, when u is equal to 1, G represent a hydrogen atom or a group chosen from hydroxyl, carboxyl, (di)$(C_1-C_4)$(alkyl)amino or (hetero)aryl, in particular aryl such as phenyl.

According to another particular embodiment of the invention, the PHA copolymer(s) are such that $R^1$ represents $(C_3-C_{30})$alkyl substituted with one or more halogen atoms such as fluorine, chlorine or bromine, more particularly linear $(C_4-C_{20})$alkyl, even more particularly $(C_5-C_{13})$alkyl, substituted with a halogen atom such as bromine. Preferably, the halogen atom is substituted at the end of said alkyl group. More preferentially, $R^1$ represents 1-halo-5-yl such as 1-bromo-5-yl.

According to another particular embodiment of the invention, the PHA copolymer(s) are such that $R^1$ represents a $(C_3-C_{30})$alkyl group substituted with one or more groups chosen from a) cyano, and more particularly represents a $(C_3-C_{13})$alkyl group, which is preferably linear, substituted with a cyano group, such as 1-cyano-3-propyl.

According to another particular embodiment of the invention, the PHA copolymer(s) are such that $R^1$ represents vii) a (hetero)aryl$(C_1-C_2)$alkyl and more particularly aryl$(C_1-C_2)$alkyl group, preferably phenylethyl.

According to another particular embodiment of the invention, the PHA copolymer(s) are such that $R^1$ represents a $(C_5-C_{28})$alkyl group substituted with one or more groups chosen from c) (hetero)cycloalkyl. More particularly, $R^1$ represents a $(C_5-C_{13})$alkyl group, which is preferably linear, substituted with a heterocycloalkyl group such as epoxide.

In particular, the PHA copolymer(s) are such that $R^2$ is chosen from linear or branched $(C_1-C_{28})$alkyl, and linear or branched $(C_2-C_{28})$alkenyl, in particular a linear hydrocarbon-based group, particularly $(C_3-C_{20})$alkyl or $(C_3-C_{20})$ alkenyl; preferably, the hydrocarbon-based group has a carbon number corresponding to the number of carbon atoms of the radical $R^1$ from which at least one carbon atom is subtracted, preferably corresponding to the number of carbon atoms of the radical $R^1$ from which two carbon atoms are subtracted.

According to one embodiment of the invention, the PHA copolymer(s) are such that the radical $R^2$ is a linear or branched, preferably linear, $(C_3-C_8)$alkyl, in particular $(C_3-C_6)$alkyl, preferably $(C_4-C_6)$alkyl group such as n-pentyl or n-hexyl.

According to another embodiment of the composition according to the invention, the PHA copolymer(s) comprise a branched $(C_3-C_8)$alkyl, particularly $(C_4-C_6)$alkyl radical $R^2$, preferably a branched $(C_4-C_6)$alkyl radical such as isobutyl.

According to another embodiment of the composition according to the invention, the PHA copolymer(s) of the invention comprise the units (A) bearing an alkyl radical $R^1$ as defined previously, the units (B) as defined previously and the units (C) bearing a linear or branched $(C_6-C_{20})$alkenyl, particularly $(C_7-C_{14})$alkenyl and more particularly $(C_8-C_{10})$ alkenyl radical, which is preferably linear and comprising only one unsaturation at the chain end, in particular, $-[CR^4(R^5)]_q-C(R^6)=C(R^7)-R^8$ with $R^4$, $R^5$, $R^6$, $R^7$ and $R^8$, which may be identical or different, representing a hydrogen atom or a $(C_1-C_4)$alkyl group such as methyl, preferably a hydrogen atom, and q represents an integer inclusively between 2 and 20, preferably between 3 and 10, more preferentially between 4 and 8 such as 6, such as $-[CH_2]_q-CH=CH_2$ and q represents an integer inclusively between 3 and 8, preferably between 4 and 6, such as 5.

According to one embodiment of the composition according to the invention, the PHA copolymer(s) comprise units (A) bearing an alkyl radical $R^1$ comprising between 8 and 16 carbon atoms substituted with one or more (preferably one) groups chosen from hydroxyl, (di)$(C_1-C_4)$(alkyl)amino, carboxyl, and R—X— as defined previously, preferably R—S— with R representing a cycloalkyl group such as cyclohexyl, heterocycloalkyl such as a sugar, more preferentially a monosaccharide such as glucose, optionally substituted aryl$(C_1-C_4)$alkyl such as $(C_1-C_4)$(alkyl)benzyl or phenylethyl, or heteroaryl$(C_1-C_4)$alkyl such as furylmethyl.

According to one embodiment of the composition according to the invention, the copolymer(s) comprise units B bearing a linear or branched, preferably linear, $(C_1-C_3)$alkyl, particularly $(C_2-C_6)$alkyl, preferably $(C_4-C_6)$alkyl radical $R^2$ such as pentyl.

According to another embodiment of the composition according to the invention, the PHA copolymer(s) comprise units (A) containing an alkyl radical $R^1$ as defined previously, units (B) as defined previously and units (C) containing a linear or branched $(C_6\text{-}C_{20})$alkenyl, particularly $(C_7\text{-}C_{14})$alkenyl radical and more particularly $(C_3\text{-}C_{10})$alkenyl radical, which is preferably linear, and comprising only one unsaturation at the chain end such as $—[CH_2]_q—CH═CH_2$ and p represents an integer inclusively between 3 and 8, preferably between 4 and 6, such as 5.

According to a particular embodiment of the invention, in the PHA copolymer(s), the units (A) comprises a hydrocarbon-based chain as defined previously, in particular iii), said unit (A) preferably being present in a molar percentage ranging from 0.1% to 99%, more preferentially a molar percentage ranging from 0.5% to 50%, even more preferentially a molar percentage ranging from 1% to 40%, better still a molar percentage ranging from 2% to 30%, or a molar percentage ranging from 5% to 20%.

According to a more particular embodiment of the invention in the PHA copolymer(s), the unit (A) is preferably present in a molar percentage ranging from 0.5% to 99%, more preferentially a molar percentage ranging from 1% to 50%, even more preferentially a molar percentage ranging from 5% to 40%, better still a molar percentage ranging from 10% to 30%; the unit (B) is present in a molar percentage ranging from 2% to 40%; and the unit (C) is present in a molar percentage ranging from 0.5% to 20% relative to the sum of the units (A), (B) and (C). Advantageously, the PHA copolymer(s) of the invention comprise from 2 mol % to 10 mol % of units (B), and from 0.5 mol % to 7 mol % of units (C); more advantageously, the copolymer comprises from 5 mol % to 35 mol % of units (B), and from 0.5 mol % to 7 mol % of units (C).

According to a more particular embodiment of the invention, the PHA copolymer(s) are such that, in the PHA copolymer(s) a):

- the unit (A) comprises a hydrocarbon-based chain as defined previously, said unit (A) being present in a molar percentage ranging from 0.1% to 99%, preferably a molar percentage ranging from 0.5% to 50%, more preferentially a molar percentage ranging from 1% to 40%, even more preferentially a molar percentage ranging from 2% to 30%, better still a molar percentage ranging from 5% to 20%, even better still a molar percentage ranging from 10% to 30% of units (A); and
- the unit (B) is present in a molar percentage ranging from 1% to 40%, preferentially a molar percentage from 2% to 10%, more preferentially a molar percentage from 5% to 35% of units (B); and/or
- the unit (C) is present in a molar percentage ranging from 0.5 to 20%, preferentially a molar percentage from 1% to 7%, more preferentially from 0.5% to 7% of units (C).

Preferably, when $R^1$ of the unit (A) is a saturated hydrocarbon-based chain, said unit (A) is present in a molar percentage of greater than 30%, more particularly greater than 50%, more preferentially greater than 60%, preferably between 60% and 90%.

The values of the molar percentages of the units (A), (B) and (C) of the PHA copolymer(s) are calculated relative to the total number of moles of (A)+(B) if the copolymer(s) do not comprise any additional units (C); otherwise, if the copolymer(s) of the invention contain three different units (A), (B) and (C), then the molar percentage is calculated relative to the total number of moles (A)+(B)+(C); otherwise, if the copolymer(s) of the invention contain four different units (A), (B), (C) and (D), then the molar percentage is calculated relative to the total number of moles (A)+(B)+(C)+(D); otherwise, if the copolymer(s) of the invention contain five different units (A), (B), (C), (D) and (E), then the molar percentage is calculated relative to the total number of moles (A)+(B)+(C)+(D)+(E).

Preferentially, the PHA copolymer(s) of the invention comprise the following repeating units, and also the optical or geometrical isomers thereof, the organic or mineral acid or base salts thereof, and the solvates thereof such as hydrates:

[Chem. 5] :

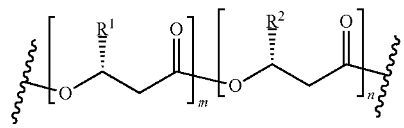

| Compounds | $R^1$ | $R^2$ |
|---|---|---|
| (1) | $—(CH_2)_8—S—CH(CH_3)—C(O)—OH$ | $—(CH_2)_4—CH_3$ |
| (2) | $—(CH_2)_8—S—(CH_2)_7—CH_3$ | $—(CH_2)_4—CH_3$ |
| (3) | $—(CH_2)_8—S—(CH_2)_8—OH$ | $—(CH_2)_4—CH_3$ |
| (4) | $—(CH_2)_8—S—(CH_2)2—NH_2$ | $—(CH_2)_4—CH_3$ |
| (5) | $—(CH_2)_8—S—$Cycl | $—(CH_2)_4—CH_3$ |
| (6) | $—(CH_2)_8—S—CH_2—$Fur | $—(CH_2)_4—CH_3$ |
| (7) | $—(CH_2)_8—S—$Suc | $—(CH_2)_4—CH_3$ |
| (8) | $—(CH_2)_8—S—(CH_2)2—$Ar | $—(CH_2)_4—CH_3$ |
| (9) | $—(CH_2)_8—S—CH_2—$Ar' | $—(CH_2)_4—CH_3$ |
| (10) | $—(CH_2)_8—S—CH(CH_3)—C(O)—OH$ | $—(CH_2)_5—CH_3$ |
| (11) | $—(CH_2)_5—$Hal | $—(CH_2)_5—CH_3$ |
| (12) | $—(CH_2)_3—CN$ | $—(CH_2)_5—CH_3$ |
| (13) | 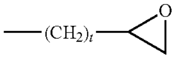 | $—(CH_2)_5—CH_3$ |
| (14) | $—(CH_2)2—$Ar | $—(CH_2)_5—CH_3$ |
| (15) | $—(CH_2)_4—CH_3$ | $—(CH_2)2—CH_3$ |
| (16) | $—(CH_2)_5—CH_3$ | $—(CH_2)_3—CH_3$ |
| (17) | $—(CH_2)6—CH_3$ | $—(CH_2)_4—CH_3$ |
| (18) | $—(CH_2)_8—CH_3$ | $—(CH_2)6—CH_3$ |

-continued

[Chem. 5] :

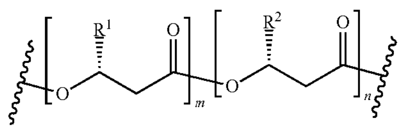

| Compounds | $R^1$ | $R^2$ |
|---|---|---|
| (19) | $-(CH_2)_3-CH(CH_3)CH_3$ | $-CH_2-CH(CH_3)CH_3$ |
| (20) | $-(CH_2)6-CH{=}CH_2$ | $-(CH_2)_5-CH_3$ |
| (21) | $-(CH_2)2-CH{=}C(CH_3)CH_3$ | $-CH_2-CH(CH_3)CH_3$ |

m and n are as defined previously, Hal represents a halogen atom such as bromine and t represents an integer between 1 and 10, preferably between 3 and 8 such as 6.

Ar: represents a (hetero)aryl group such as phenyl;

Ar': represents a $(C_1\text{-}C_4)$alkyl(hetero)aryl group such as t-butylphenyl, preferably 4-t-butylphenyl;

Cycl: represents a cyclohexyl group;

Fur: represents.a furyl group, preferably 2-furyl;

Sug: represents a sugar group, in particular a monosaccharide optionally protected with one or more groups such as acyl; preferably, Sug represents:

[Chem. 6] :

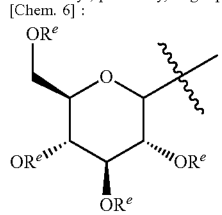

with Re, representing a group R-C(O)-, with $R^f$ representing a $(C_1\text{-}C_4)$alkyl group such as methyl.

In particular, the stereochemistry of the carbon atoms bearing the radicals $R^1$ and $R^2$ is of the same (R) or (S) configuration, preferably of (R) configuration.

More particularly, the stereochemistry of the carbon atoms bearing the radicals $R^1$, $R^2$ and $R^3$ is of the same (R) or (S) configuration, preferably of (R) configuration. More particularly, the stereochemistry of the carbon atoms bearing the radicals $R^1$, $R^2$, $R^3$ and $R^4$ is of the same (R) or (S) configuration, preferably of (R) configuration.

More particularly, the stereochemistry of the carbon atoms bearing the radicals $R^1$, $R^2$, $R^3$, $R^4$ and $R^5$ is of the same (R) or (S) configuration, preferably of (R) configuration.

More preferentially, the PHA copolymer(s) have the following formula, and also the optical isomers thereof, the organic or mineral acid or base salts thereof, and the solvates thereof such as hydrates:

[Chem. 7]:

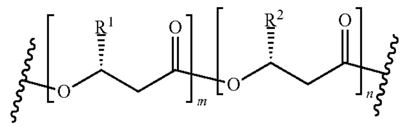

| Compounds | $R^1$ | $R^2$ |
|---|---|---|
| (1') | $-(CH_2)_8-S-CH(CH_3)-C(O)-OH$ | $-(CH_2)_4-CH_3$ |
| (2') | $-(CH_2)_8-S-(CH_2)7-CH_3$ | $-(CH_2)_4-CH_3$ |
| (3') | $-(CH_2)_8-S-(CH_2)_8-OH$ | $-(CH_2)_4-CH_3$ |
| (4') | $-(CH_2)_8-S-(CH_2)_2-NH2$ | $-(CH_2)_4-CH_3$ |
| (5') | $-(CH_2)_8-S-$Cycl | $-(CH_2)_4-CH_3$ |
| (6') | $-(CH_2)_8-S-CH_2-$Fur | $-(CH_2)_4-CH_3$ |
| (7') | $-(CH_2)_8-S-$Suc | $-(CH_2)_4-CH_3$ |
| (8') | $-(CH_2)_8-S-(CH_2)_2-$Ar | $-(CH_2)_4-CH_3$ |
| (9') | $-(CH_2)_8-S-CH_2-$Ar' | $-(CH_2)_4-CH_3$ |
| (10') | $-(CH_2)_8-S-CH(CH_3)-C(O)-OH$ | $-(CH_2)_5-CH_3$ |
| (11') | $-(CH_2)_5-$Hal | $-(CH_2)_5-CH_3$ |
| (12') | $-(CH_2)3-CN$ | $-(CH_2)_5-CH_3$ |
| (13') | 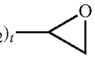 | $-(CH_2)_5-CH_3$ |
| (14') | $-(CH_2)_2-$Ar | $-(CH_2)_5-CH_3$ |
| (15') | $-(CH_2)_4-CH_3$ | $-(CH_2)_2-CH_3$ |
| (16') | $-(CH_2)_5-CH_3$ | $-(CH_2)3-CH_3$ |

-continued

| [Chem. 7]: | | | |
|---|---|---|---|
| (17') | $—(CH_2)_6—CH_3$ | $—(CH_2)_4—CH_3$ | |
| (18') | $—(CH_2)_8—CH_3$ | $—(CH_2)_6—CH_3$ | |
| (19') (ex. 3) | $—(CH_2)3—CH(CH_3)CH_3$ | $—CH_2—CH(CH_3)CH_3$ | |
| (20') | $—(CH_2)_6—CH{=}CH_2$ | $—(CH_2)_5—CH_3$ | |
| (21') | $—(CH_2)_2—CH{=}C(CH_3)CH_3$ | $—CH_2—CH(CH_3)CH_3$ | |
| Compounds | $R^1$ | $R^2$ | $R^3$ |
| (22) | $—(CH_2)_4—CH_3$ | $—(CH_2)_2—CH_3$ | $—CH_3$ |
| (23) | $—(CH_2)_5—CH_3$ | $—(CH_2)3—CH_3$ | $—CH_2—CH_3$ |
| (24) | $—(CH_2)_6—CH_3$ | $—(CH_2)_4—CH_3$ | $—(CH_2)_2—CH_3$ |

M, n, Hal, t, Ar, Ar', Cycl, Fur and Sug are as defined previously for compounds (1) to (14).

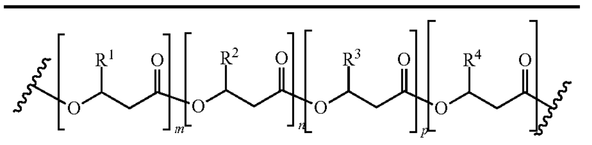

| Compounds | $R^1$ | $R^2$ | $R^3$ | $R^4$ |
|---|---|---|---|---|
| (25) | $—(CH_2)_8—CH_3$ | $—(CH_2)_6—CH_3$ | $—(CH_2)_4—CH_3$ | $—(CH_2)_2—CH_3$ |
| (26) | $—(CH_2)_6—CH_3$ | $—(CH_2)_4—CH_3$ | $—(CH_2)_2—CH_3$ | $—CH_3$ |

-continued

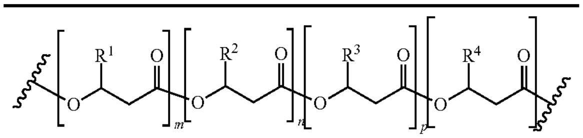

| Compounds | $R^1$ | $R^2$ | $R^3$ | $R^4$ |
|---|---|---|---|---|
| (27) | $—(CH_2)_2—CN$ | $—(CH_2)_5—CH_3$ | $—(CH_2)_3—CH_3$ | $—CN$ |
| (28) | $—(CH_2)_2—Ar$ | $—(CH_2)_5—CH_3$ | $—(CH_2)_3—CH_3$ | $—Ar$ |

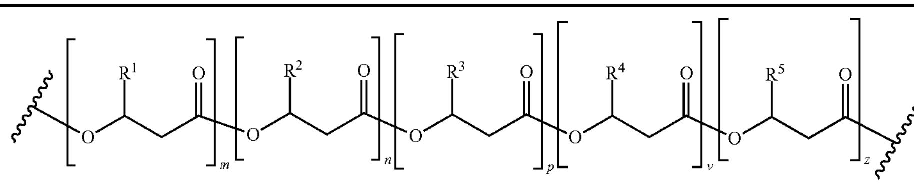

| Compounds | $R^1$ | $R^2$ | $R^3$ | $R^4$ | $R^5$ |
|---|---|---|---|---|---|
| (29) | $—(CH_2)_9—CH{=}CH_2$ | $—(CH_2)_5—CH_3$ | $—(CH_2)_3—CH_3$ | $—(CH_2)_7—CH{=}CH_2$ | $—(CH_2)_5—CH{=}CH_2$ |
| (30) | $—(CH_2)_9—CH{=}CH_2$ | $—(CH_2)_4—CH_3$ | $—(CH_2)_2—CH_3$ | $—(CH_2)_7—CH{=}CH_2$ | $—(CH_2)_5—CH{=}CH_2$ |
| (31) | $—(CH_2)_8—CH_3$ | $—(CH_2)_6—CH_3$ | $—(CH_2)_4—CH_3$ | $—(CH_2)_2—CH_3$ | $—CH_3$ |
| (32) | $—(CH_2)_{10}—CH_3$ | $—(CH_2)_8—CH_3$ | $—(CH_2)_6—CH_3$ | $—(CH_2)_4—CH_3$ | $—(CH_2)_2—CH_3$ |
| (33) | $—(CH_2)_8—S—CH(CH_3)—C(O)—OH$ | $—(CH_2)_4—CH_3$ | $—(CH_2)_2—CH_3$ | $—(CH_2)_6—S—CH(CH_3)—C(O)—OH$ | $—(CH_2)_4—S—CH(CH_3)—C(O)—OH$ |
| (34) | $—(CH_2)_8—S—(CH_2)_7—CH_3$ | $—(CH_2)_4—CH_3$ | $—(CH_2)_2—CH_3$ | $—(CH_2)_6—S—(CH_2)_7—CH_3$ | $—(CH_2)_4—S—(CH_2)_7—CH_3$ |
| (35) | $—(CH_2)_8—S—(CH_2)_8—OH$ | $—(CH_2)_4—CH_3$ | $—(CH_2)_2—CH_3$ | $—(CH_2)_6—S—(CH_2)_8—OH$ | $—(CH_2)_4—S—(CH_2)_8—OH$ |
| (36) | $—(CH_2)_8—S—(CH_2)_2—NH_2$ | $—(CH_2)_4—CH_3$ | $—(CH_2)_2—CH_3$ | $—(CH_2)_6—S—(CH_2)_2—NH_2$ | $—(CH_2)_4—S—(CH_2)_2—NH_2$ |
| (37) | $—(CH_2)_8—S—Cycl$ | $—(CH_2)_4—CH_3$ | $—(CH_2)_2—CH_3$ | $—(CH_2)_6—S—Cycl$ | $—(CH_2)_4—S—Cycl$ |
| (38) | $—(CH_2)_8—S—CH_2—Fur$ | $—(CH_2)_4—CH_3$ | $—(CH_2)_2—CH_3$ | $—(CH_2)_6—S—CH_2—Fur$ | $—(CH_2)_4—S—CH_2—Fur$ |
| (39) | $—(CH_2)_8—S—Sug$ | $—(CH_2)_4—CH_3$ | $—(CH_2)_2—CH_3$ | $—(CH_2)_6—S—Sug$ | $—(CH_2)_4—S—Sug$ |
| (40) | $—(CH_2)_8—S—(CH_2)_2—Ar$ | $—(CH_2)_4—CH_3$ | $—(CH_2)_2—CH_3$ | $—(CH_2)_6—S—(CH_2)_2—Ar$ | $—(CH_2)_4—S—(CH_2)_2—Ar$ |
| (41) | $—(CH_2)_8—S—CH_2—Ar'$ | $—(CH_2)_4—CH_3$ | $—(CH_2)_2—CH_3$ | $—(CH_2)_6—S—(CH_2)_2—Ar'$ | $—(CH_2)_4—S—CH_2—Ar'$ |
| (42) | $—(CH_2)_8—S—CH(CH_3)—C(O)—OH$ | $—(CH_2)_5—CH_3$ | $—(CH_2)_3—CH_3$ | $—(CH_2)_6—S—CH(CH_3)—C(O)—OH$ | $—(CH_2)_4—S—CH(CH_3)—C(O)—OH$ |
| (43) | $—(CH_2)_8—Hal$ | $—(CH_2)_5—CH_3$ | $—(CH_2)_3—CH_3$ | $—(CH_2)_3—Hal$ | $—(CH_2)—Hal$ |
| (44) | 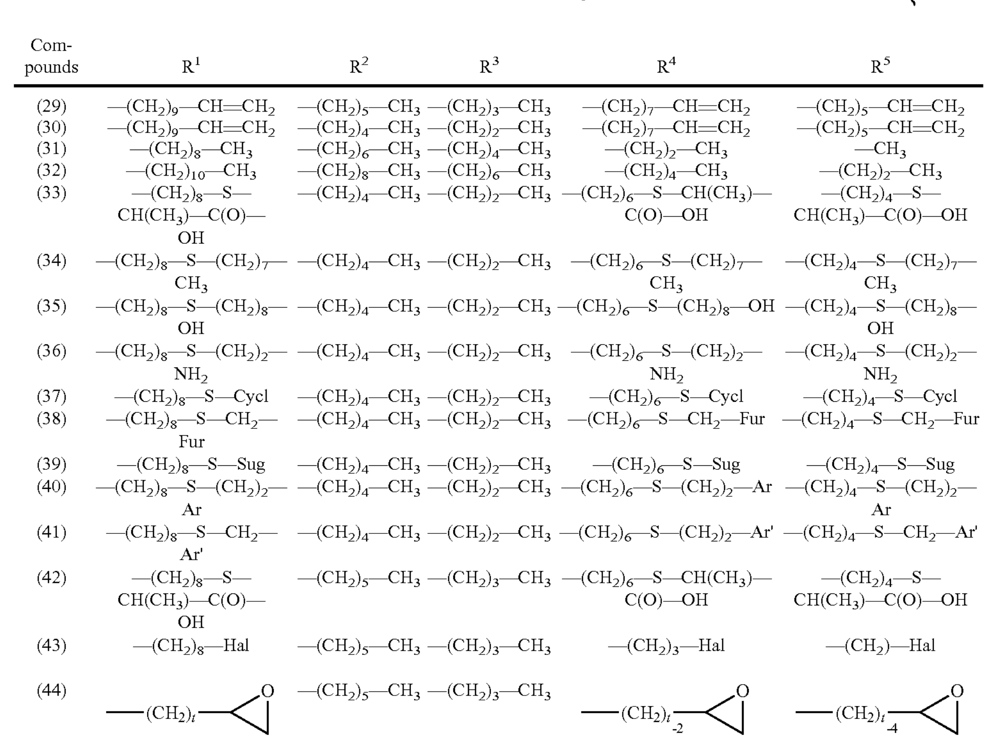 | $—(CH_2)_5—CH_3$ | $—(CH_2)_3—CH_3$ | | |

The PHA copolymer(s) of the invention preferably have a number-average molecular weight ranging from 50 000 to 150 000.

The molecular weight may notably be measured by size exclusion chromatography. A method is described below in the examples.

The PHA copolymer(s) are particularly present in the composition according to the invention in a content ranging from 0.1% to 30% by weight and preferably ranging from 0.1% to 25% by weight relative to the total weight of the composition.

The PHA copolymer(s) preferably have a number-average molecular weight ranging from 50 000 to 150 000.

The molecular weight may notably be measured by size exclusion chromatography. A method is described below in the examples.

The copolymer may be present in the composition according to the invention in a content ranging from 0.1% to 30% by weight, and preferably from 0.1% to 25% by weight, relative to the total weight of the composition.

Method for Preparing the PHA Copolymer(s):

The methods for preparing the PHA copolymer(s) of the invention are known to those skilled in the art. Mention may notably be made of the use of "functionalizable" PHA-producing microbial strains.

The term "functionalizable" means that the PHA copolymer(s) comprise a hydrocarbon-based chain comprising one or more atoms or groups that are capable of reacting chemically with another reagent—also referred to as "reactive atoms or reactive groups"- to give a Σ covalent bond with said reagent. The reagent is, for example, a compound comprising at least one nucleophilic group and said functionalized hydrocarbon-based chain comprises at least one electrophilic or nucleofugal atom or group, the nucleophilic group(s) reacting with the electrophilic group(s) to covalently graft Σ the reagent. The nucleophilic reagent may also react with one or more unsaturations of the alkenyl group(s) to also lead to grafting by covalent bonding of the functionalized hydrocarbon-based chain with said reagent. The addition may also be radical-based, an addition of Markovnikov or anti-Markovnikov type, or nucleophilic or electrophilic substitution. The addition or condensation reactions may or may not take place via a radical route, with or without the use of catalysts or of enzymes, with heating preferably to a temperature less than or equal to 100° C. or without supplying heat, under a pressure of greater than 1 atm or otherwise, under an inert atmosphere or otherwise, or under oxygen or otherwise.

The term "nucleophilic" refers to any atom or group which is electron-donating by an inductive effect +I and/or a mesomeric effect +M. Electron-donating groups that may be mentioned include hydroxyl, thiol and amino groups.

The term "electrophilic" refers to any atom or group which is electron-withdrawing by an inductive effect −I and/or a mesomeric effect −M. Electron-withdrawing species that may be mentioned include.

The microorganisms which produce PHAs of the invention notably bearing a hydrocarbon-based chain may be naturally produced by the bacterial kingdom, such as Cyanobacteria of the order of Nostocales (e.g.: *Nostoc muscorum, Synechocystis* and *Synechococcus*) but mainly by the Proteobacteria, for example in the class of:

- beta-Proteobacteria, of the order Burkholderiales (*Cupriavidus negator* synonym *Rasltonia eutropha*)
- alpha-Proteobacteria, of the order Rhodobacteriales (*Rhodobacter capsulatus* marine and photosynthetic)
- gamma-Proteobacteria, of the order Pseudomonales of the family Moraxellaceae (*Acinetobacter junii*).

Among the microorganisms of the bacterial kingdom, the genera *Azotobacter, Hydrogenomomas* or *Chromatium* are the most representative of the PHA-producing organisms.

The organisms which naturally produce PHAs notably bearing a $C_3$-$C_5$ hydrocarbon-based chain are notably Proteobacteria, such as gamma-Proteobacteria, and more particularly of the order Pseudomonales of the family *Pseudomonas* such as *Pseudomonas resinovorans, Pseudomonas putida, Pseudomonas fluorescens, Pseudomonas aeruginosa, Pseudomonas citronellolis, Pseudomonas mendocina, Pseudomonas chlororaphis* and preferably *Pseudomonas putida* GPo1 and *Pseudomonas putida* KT2440, preferably *Pseudomonas putida* and *Pseudomonas putida* and in particular *Pseudomonas putida* GPo1 and *Pseudomonas putida* KT2440.

Certain organisms may also naturally produce PHAs without belonging to the order of Pseudomonales, such as *Commamonas testosteroni* which belongs to the class of beta-Proteobacteria of the order Burkholderiales of the family of Comamonadaceae.

The PHA-producing microorganism according to the invention may also be a recombinant strain if a 3-oxidation PHA synthase metabolic pathway is present. The 3-oxidation PHA synthase metabolic pathway is mainly represented by four classes of enzymes, EC: 2.3.1 B2, EC: 2.3.1 B3, EC: 2.3.1 B4 and EC: 2.3.1 B5.

The recombinant strain may be from the Bacteria kingdom, for instance *Escherichia coli*, or from the Plantae kingdom, for instance *Chlorella pyrenoidosa* (*International Journal of Biological Macromolecules,* 116, 552-562 "Influence of nitrogen on growth, biomass composition, production, and properties of polyhydroxyalkanoates (PHAs) by microalgae") or from the Fungi kingdom, for instance *Saccharomyces cerevisiae* or *Yarrowia lipolytica: Applied Microbiology and Biotechnology* 91, 1327-1340 (2011) "Engineering polyhydroxyalkanoate content and monomer composition in the oleaginous yeast *Yarrowia lipolytica* by modifying the β-oxidation multifunctional protein").

Use may also be made of genetically modified microorganisms, which may make it possible, for example, to increase the production of PHA, and/or to increase the oxygen consumption capacity, and/or to reduce the autolysis and/or to modify the monomer ratio.

It is known that, for PHAs, a large portion of the total production cost is devoted to the culture medium and mainly to the substrate/carbon source. Use may thus be made of genetically modified microorganisms using a smaller amount of nutrient (carbon source) for their growth, for example microorganisms that are photo-autotrophic by nature, i.e. using light and $CO_2$ as main energy source.

The copolymer may be obtained in a known manner by biosynthesis, for example with the microorganisms belonging to the genus *Pseudomonas*, such as *Pseudomonas resinovorans, Pseudomonas putida, Pseudomonas fluorescens, Pseudomonas aeruginosa, Pseudomonas citronellolis, Pseudomonas mendocina, Pseudomonas chlororaphis* and preferably *Pseudomonas putida*; and with a carbon source which may be a $C_2$-$C_{20}$, preferably $C_6$-$C_{18}$, carboxylic acid, such as acetic acid, propionic acid, butyric acid, hexanoic acid, heptanoic acid, octanoic acid, nonanoic acid, dodecanoic acid; a saccharide, such as fructose, maltose, lactose, xylose, arabinose, etc.); an n-alkane, such as hexane, octane or dodecane; an n-alcohol, such as methanol, ethanol, octanol or glycerol; methane or carbon dioxide.

The biosynthesis may optionally be performed in the presence of an inhibitor of the β-oxidation pathway, such as acrylic acid, methacrylic acid, propionic acid, cinnamic acid, salicylic acid, pentenoic acid, 2-butynoic acid, 2-octynoic acid or phenylpropionic acid, and preferably acrylic acid.

According to one embodiment, the process for preparing the PHAs of the invention uses microbial cells which produce PHAs via genetically modified microorganisms (GMOs). The genetic modification may increase the production of PHA, increase the oxygen absorption capacity, increase the resistance to the toxicity of solvents, reduce the autolysis, modify the ratio of the PHA comonomers, and/or any combination thereof. In some of these embodiments, the modification of the comonomer ratio of the unit (A) increases the amount of predominant monomer versus (B) of the PHA of the invention which is obtained. In another embodiment, the PHA-producing microbial cells reproduce naturally.

By way of example, a genetically modified microbial strain producing PHA that is functionalizable or comprising a reactive group that may be mentioned is *Pseudomonas entomophila* LAC23 (*Biomacromolecules.* 2014 Jun. 9; 15(6):2310-9. doi: 10.1021/bm500669s).

It is also possible to use genetically modified microorganisms which produce phenylvaleric-co-3-hydroxydodecanoic copolymers (*Sci. China Life Sci*., Shen R., et al., 57 No. 1, (2014) with a strain such as *Pseudomonas entomophila* LAC23.

Nutrients, such as water-soluble salts based on nitrogen, phosphorus, sulfur, magnesium, sodium, potassium and iron, may also be used for the biosynthesis.

The known appropriate temperature, pH and dissolved oxygen ($O_D$) conditions may be used for the culturing of the microorganisms.

The microorganisms may be cultured according to any known method of culturing, such as in a bioreactor in continuous or batch mode, in fed or unfed mode.

The biosynthesis of the polymers used according to the invention is notably described in the article "Biosynthesis and Properties of Medium-Chain-Length Polyhydroxyalkanoates with Enriched Content of the Dominant Monomer", Xun Juan et al., Biomacromolecules 2012, 13, 2926-2932, and in patent application WO 2011/069244.

The microbial strains producing PHA which is functionalizable or comprising a reactive group, as defined previously, are, for example, of the genus *Pseudomonas* such as *P. cichorii* YN2, *P. citronellolis, P. jessenii*, and more generally with species of *Pseudomonas putida* such as *Pseudomonas putida* GPo1 (synonym of *Pseudomonas oleovorans*), *P. putida* KT2442, *P. putida* KCTC 2407, *P. putida* BM01.

The Carbon Source(s):

One means for gaining access to the PHAs of the invention is to introduce one or more organic compounds into the culture medium, this or these organic compounds representing a carbon source preferably chosen from alkanes, alkenes, alcohols, carboxylic acids and a mixture thereof.

In one embodiment, the organic compound(s) will preferably be chosen from alcohols, carboxylic acids and a mixture thereof.

The carbon source(s) may be classified in two categories:

1) Carbon Source Via One or More Organic Compounds Introduced into the Medium:

One means for gaining access to the PHAs of the invention is to introduce one or more organic compounds into the culture medium, this organic compound being a carbon source preferably chosen from alkanes, alkenes, alcohols, carboxylic acids and mixtures thereof.

According to a particular embodiment of the invention, the organic compound(s) are chosen from alcohols, in particular ($C_5$-$C_{20}$)alkanols, and/or carboxylic acids, in particular ($C_5$-$C_{20}$)alkanoic acids.

The carbon source(s) may be classified into three groups according to their intended use:

- group A: the organic compound may aid the growth of the productive strain and aid the production of PHA structural linked to the organic compound.
- group B: the organic compound may aid the growth of the strain but does not participate in the production of PHA structural linked to the organic compound.
- group C: the organic compound does not participate in the growth of the strain.

Such microbiological processes are known to those skilled in the art, notably in the scientific literature. Mention may be made of: *International Journal of Biological Macromolecules* 28, 23-29 (2000); *The Journal of Microbiology,* 45, No. 2, 87-97, (2007).

According to one variant, the integration of the substrate that is structurally linked to the reactive atom(s) or to the reactive group(s) of the PHAs of the invention is introduced directly into the medium as sole carbon source in a medium suitable for microbial growth. (Example: group A for *P. putida* GPo1: alkenoic acid, notably terminal).

According to another variant, the integration of the substrate that is structurally linked to the reactive atom(s), notably halogen, or to the reactive group(s) of the PHAs of the invention is introduced into the medium as carbon source with a second carbon source as co-substrate which is also structurally linked to the PHA, in a medium suitable for microbial growth. (Example: group B for *P. putida* GPo1: haloalkanoic acids which are preferably terminal, such as terminal bromoalkanoic acids).

According to yet another variant, the integration of the substrate that is structurally linked to the reactive atom(s), notably halogen, or to the reactive group(s) of the PHAs of the invention may be introduced directly into the medium as carbon source with a second carbon source as co-substrate which is also structurally linked to the PHAs and a third carbon source as co-substrate which is not structurally linked to the PHAs, in a medium suitable for microbial growth. (Example: group C glucose or sucrose).

In one embodiment, the β-oxidation pathway inhibitor is acrylic acid, 2-butynoic acid, 2-octynoic acid, phenylpropionic acid, propionic acid, trans-cinnamic acid, salicylic acid, methacrylic acid, 4-pentenoic acid or 3-mercaptopropionic acid.

In one embodiment of the first aspect, the functionalized fatty acid is a functionalized hexanoic acid, functionalized heptanoic acid, functionalized octanoic acid, functionalized nonanoic acid, functionalized decanoic acid, functionalized undecanoic acid, functionalized dodecanoic acid or functionalized tetradecanoic acid.

The functionalization may be introduced by means of an organic compound chosen from precursors of the alcohol and/or carboxylic acid category, notably:

- for functionalization of the PHA(s) with a branched alkyl group: see, for example *Applied and Environmental Microbiology,* 60, No. 9, 3245-325 (1994);
- for functionalization of the PHA(s) with a linear alkyl group comprising a terminal cyclohexyl unit: see, for example doi.org/10.1016/S0141-8130(01)00144-1;

- for functionalization of the PHA(s) with an unsaturated alkyl group which is preferably terminal: see, for example doi.org/10.1021/bm8005616);
- for functionalization of the PHA(s) with a linear alkyl group comprising a halogen preferably at the end of the hydrocarbon-based chain (doi.org/10.1021/ma00033a002);
- for functionalization of the PHA(s) with a (hetero)aromatic alkyl group, for example phenyl, benzoyl, phenoxy, see, for example *J. Microbiol. Biotechnol.,* 11, 3, 435-442 (2001);
- for functionalization of the PHA(s) with a linear alkyl group comprising a heteroatom notably at the end of the hydrocarbon-based chain, see, for example DOI 10.1007/s00253-011-3099-4;
- for functionalization of the PHA(s) with a linear alkyl group comprising a cyano function notably at the end of the hydrocarbon-based chain, see, for example doi.org/10.1111/j.1574-6968.1992.tb05839.x;
- for functionalization of the PHA(s) with a linear alkyl group comprising an epoxy function notably at the end of the hydrocarbon-based chain, see, for example doi.org/10.1016/S1381-5148(97)00024-2;

The review *International Microbiology* 16:1-15 (2013) doi: 10.2436/20.1501.01.175) also mentions the majority of the functionalized native PHAs.

In a particular embodiment of the invention, the fatty acid from group A is chosen from 11-undecenoic acid, 10-epoxyundecanoic acid, 5-phenylvaleric acid, citronellol and 5-cyanopentanoic acid.

In a particular embodiment of the invention, the fatty acid from group B is chosen from halooctanoic acids such as 8-bromooctanoic acid.

In a particular embodiment of the invention, the carbon source from group C is a monosaccharide, preferably glucose.

2) Carbon Source in the Presence of Oxidation Inhibitor Introduced into the Medium:

Another aspect of the invention is the use of the PHA-producing microbial strains in a medium that is suitable for microbial growth, said medium comprising: a substrate which is structurally linked to the PHA(s); at least one carbon source which is not structurally linked to the PHA(s); and at least one oxidation and notably β-oxidation pathway inhibitor. This allows the growth of the microbial cells to take place in said medium, the microbial cells synthesizing the PHA polymer(s) of the invention; preferably copolymer particularly containing more than 95% of identical units, which has a comonomer ratio of unit (A) and of unit (B) which differs from that obtained in the absence of the β-oxidation pathway inhibitor.

The scheme below illustrates, by way of example, the functionalization of PHA copolymers according to the invention starting from a PHA copolymer bearing an unsaturated hydrocarbon-based chain, according to Scheme 1 below:

[Chem. 8]

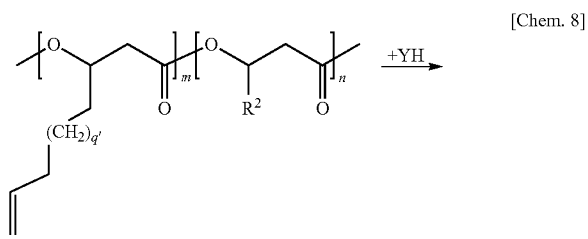

-continued

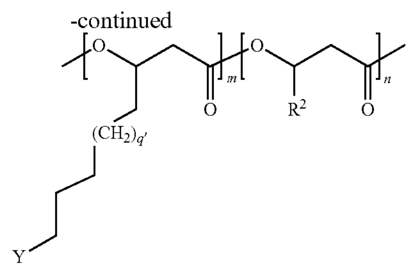

in which Scheme 1:

$R^2$, m and n are as defined previously;

Y represents a group chosen from Hal such as chlorine or bromine, hydroxyl, thiol, (di)($C_1$-$C_4$)(alkyl)amino, R—X with R representing a group chosen from α) cycloalkyl such as cyclohexyl, β) heterocycloalkyl such as a sugar, preferably a monosaccharide such as glucose, γ) (hetero)aryl such as phenyl; δ) a cosmetic active agent as defined previously; ε) ($C_1$-$C_{20}$)alkyl, ($C_2$-$C_{20}$)alkenyl, ($C_2$-$C_{20}$)alkynyl; and X representing a') O, S, N($R_a$) or Si($R_b$)($R_c$) or e) linear or branched ($C_1$-$C_{20}$)alkyl, with $R_a$, $R_b$ and $R_c$ as defined previously;

q' represents an integer inclusively between 2 and 20, preferably between 3 and 10, more preferentially between 4 and 8 such as 6, better still between 3 and 8, preferably between 4 and 6, such as 5.

Other reactions may be performed using double or triple unsaturations such as Michael or Diels-Alder additions, radical reactions, catalytic (notably with Pd or Ni) or non-catalytic hydrogenation reactions, halogenation reactions, notably with bromine, hydration reactions or oxidation reactions, which may or may not be controlled, and reactions on electrophiles as represented schematically below.

According to a particular embodiment of the invention, the PHA copolymers comprise

- a linear or branched, saturated hydrocarbon-based chain $R^1$, substituted and/or interrupted with groups as defined previously for $R^1$, comprising in total between 5 and 30 carbon atoms, preferably between 6 and 20 carbon atoms and more particularly between 7 and 11 carbon atoms, and
- a hydrocarbon-based chain $R^2$ representing a linear or branched ($C_3$-$C_{20}$)alkenyl, particularly ($C_5$-$C_{14}$)alkenyl and more particularly ($C_7$-$C_{10}$)alkenyl radical, which is preferably linear and comprising only one unsaturation at the chain end, in particular —$[CR^4(R^5)]_q$—$C(R^6)$═$C(R^7)$—$R^8$ with $R^4$, $R^5$, $R^6$, $R^7$ and $R^8$, which may be identical or different, representing a hydrogen atom or a ($C_1$-$C_4$)alkyl group such as methyl, preferably a hydrogen atom, and q represents an integer inclusively between 2 and 20, preferably between 3 and 10, more preferentially between 4 and 8 such as 6, such as —$[CH_2]_q$—CH═$CH_2$ and q represents an integer inclusively between 3 and 8, preferably between 4 and 6, such as 5, said chain $R^2$ comprising between 1% and 99%, preferentially between 2% and 50% and even more preferentially between 3% and 40% of unsaturations, and even more particularly between 3% and 30% of unsaturations, better still between 5% and 20% of unsaturations. According to this particular embodiment of the invention in which the PHA copolymers comprise unsaturations, these unsaturations may be chemically modified: A) via addition reactions, such as radical additions, Michael additions, electrophilic additions, Diels-Alder, halogenation, hydration or hydrogenation reaction, and preferably hydrothiolation reaction with particles, chemical compounds or polymers.

In particular, the hydrothiolation reactions may be performed in the presence of a thermal initiator, a redox initiator or a photochemical initiator and of an organic compound bearing a sulfhydryl group, notably chosen from:

- linear, branched, cyclic or aromatic alkanethiols including 1 to 14 carbon atoms, such as methane-, ethane-, propane-, pentane-, cyclopentane-, hexane-, cyclohexane-, heptane-, octane-, phenylethane-, 4-tert-butylphenylmethane- or 2-furanmethane-thiol, preferably hexane-, cyclohexane-, heptane-, octane-, phenylethane-, 4-tert-butylphenylmethane- or 2-furanmethane-thiol;
- organosiloxanes bearing a thiol function, such as (3-mercaptopropyl)trimethoxysilane, (3-mercaptopropyl) methyldimethoxysilane, 2-(triethoxysilyl)ethanethiol or mercaptopropyl-isobutyl-POSS;
- thiol-based silicone oils, notably those described in the document DOI: 10.1016/j.actbio.2015.01.020);
- thiol-based oligomers or polymers bearing a reactive function, such as an amine, an alcohol, an acid, a halogen, a thiol, an epoxide, a nitrile, an isocyanate, a heteroatom, preferably cysteine, cysteamine, N-acetylcysteamine, 2-mercaptoethanol, 1-mercapto-2-propanol, 8-mercapto-1-octanol, thiolactic acid, thioglycolic acid, 3-mercaptopropionic acid, 11-mercaptoundecanoic acid, polyethylene glycol dithiol, 3-mercaptopropionitrile, 1,3-propanedithiol, 4-cyano-1-butanethiol, 3-chloro-1-propanethiol, 1-thio-β-D-glucose tetraacetate; and
- thiols which may be obtained from disulfide reduction, such as phenyl disulfide or furfuryl disulfide.

Examples of initiators that may be mentioned include: tert-butyl peroxy-2-ethylhexanoate, cumene perpivalate, tert-butyl peroxylaurate, benzoyl peroxide, lauroyl peroxide, octanoyl peroxide, di-tert-butyl peroxide, tert-butylcumyl peroxide, dicumyl peroxide, 2,2'-azobisisobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1-bis(tert-butylperoxy)-3,3,5-trimethylcyclohexane, 1,1-bis(tert-butylperoxy)cyclohexane, 1,4-bis(tert-butylperoxycarbonyl)cyclohexane, 2,2-bis(tert-butylperoxy)octane, n-butyl 4,4-bis(tert-butylperoxy) valerate, 2,2-bis(tert-butylperoxy)butane, 1,3-bis(tert-butylperoxyisopropyl)benzene, 2,5-dimethyl-2,5-bis(tert-butylperoxy)hexane, 2,5-dimethyl-2,5-di(benzoylperoxy) hexane, di-tert-butyl diperoxyisophthalate, 2,2-bis(4,4-di-tert-butylperoxycyclohexyl)propane, di-tert-butyl peroxy-α-methylsuccinate, di-tert-butyl peroxydimethylglutarate, di-tert-butyl peroxyhexahydroterephthalate, di-tert-butyl peroxyazelate, 2,5-dimethyl-2,5-bis(tert-butylperoxy) hexane, diethylene glycol bis(tert-butylperoxycarbonate), di-tert-butyl peroxytrimethyladipate, tris(tert-butylperoxy) triazine, vinyltris(tert-butylperoxy)silane phenothiazine, tetracene, perylene, anthracene, 9,10-diphenylanthracene, thioxanthone, benzophenone, acetophenone, xanthone, fluorenone, anthraquinone, 9,10-dimethylanthracene, 2-ethyl-9,10-dimethyloxyanthracene, 2,6-dimethylnaphthalene, 2,5-diphenyl-1,3,4-oxadiazole, xanthopinacol, 1,2-benzanthracene, 9-nitroanthracene. Each of these initiators may be used alone or in combination with others.

The chemical reactions mentioned previously are known to those skilled in the art. Mention may notably be made of the following documents: Synthesis and preparation of PHAs modified with polyethylene glycol dithiol: 10.1021/acs.biomac.9b00479*; Biomacromolecules,* 19, 3536-3548 (2018); Synthesis and preparation of PHAs modified with mercaptohexanol: 10.1021/acs.biomac.8b01257*; Biomacromolecules,* 20, 2, 645-652 (2019); Synthesis and preparation of PHAs modified with hydroxycinnamic acid sulfate, and zosteric acid: 10.1021/bm049962e; *Biomacromolecules,* 5, 4, 1452-1456 (2004); Radical addition of methyl methacrylate to a PHOUn: 10.1002/1521-3935(20010701)202:11<2281::AID-MACP2281>3.0.CO; 2-9*; Macromolecular Chemistry and Physics*, vol. 202, 11, 2281-2286 (2001); Synthesis and preparation of PHAs modified with a polysilsesquioxane (POSS): 10.1016/j.polymer.2005.04.020*; Polymer* Vol. 46, 14, 5025-5031 (2005); Grafting of thio-beta-glucose to saturated side chains: 1022-1336/99/0202-0091$17.50+0.50/0*; Macromol. Rapid Commun.,* 20, 91-94 (1999)

and/or

B) via oxidation reactions, which may or may not be controlled, for example with permanganates of a concentrated or dilute alkaline agent, or ozonolysis, oxidation in the presence of a reducing agent, making it possible to obtain novel materials bearing hydroxyl, epoxide or carboxyl groups in the terminal position of the side chains.

The chemical reactions mentioned previously are known to those skilled in the art. Mention may notably be made of the following documents: 10.1021/bm049337*; Biomacromolecules*, vol. 6, 2, 891-896 (2005); 10.1016/S0032-3861(99)00347-X; *Polymer*, vol. 41, 5, 1703-1709 (2000); 10.1021/ma9714528 and 10.1016/S1381-5148(97)00024-2*; Macromolecules,* 23, 15, 3705-3707 (1990); 10.1016/S0032-3861(01)00692-9*; Polymer*, vol. 43, 4, 1095-1101 (2002); 10.1016/S0032-3861(99)00347-X; *Polymer*, vol. 41, 5, 1703-1709 (2000); and 10.1021/bm025728h; *Biomacromolecules*, vol. 4, 2, 193-195 (2003).

Example of functionalization of PHA copolymers according to the invention starting from a PHA copolymer bearing a hydrocarbon-based chain containing an epoxide group, according to Scheme 2 below:

[Chem. 9]

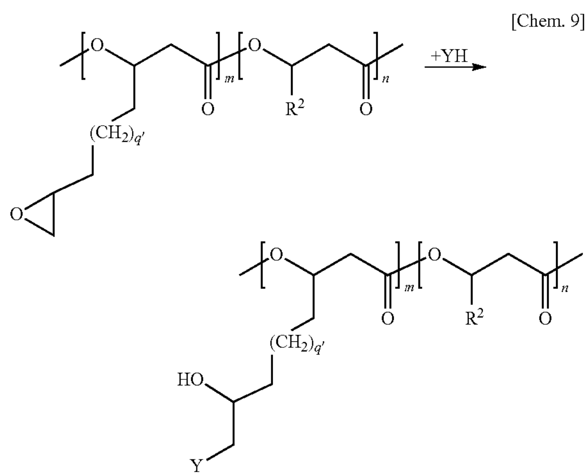

in which Scheme 2 Y, m, n, q' and R2 are as defined in Scheme 1.

The epoxide structure may be obtained via a conventional method known to those skilled in the art, whether via biotechnological processes or via chemical processes such as oxidation of unsaturation as mentioned previously. The peroxide group(s) may react with carboxylic acids, maleic anhydrides, amines, alcohols, thiols or isocyanates, all these reagents including at least one linear or branched, cyclic or acyclic, saturated or unsaturated $C_1$-$C_{20}$ hydrocarbon-based chain, or borne by an oligomer or polymer, in particular amino (poly)saccharides such as compounds derived from chitosan and (poly)sil(ox)anes; 3-glycidyloxypropyltrimethoxysilane, 3-aminopropyltriethoxysilane 3-(trimethoxysilyl)propylcarbamic acid, diethanolamine, or 3-mercapto-1-propanesulfonate of alkali metal or alkaline-earth metal salts such as sodium. The epoxide groups may also react with water.

Mention may notably be made of the following documents:

- Preparation of PHA bearing charges starting with diethanolamine: 10.1021/bm8005616, *Biomacromolecules*, vol. 9, 8, 2091-2096 (2008);
- Preparation of PHA bearing charges starting with sodium 3-mercapto-1-propanesulfonate: 10.1021/acs.biomac.9b00870 *Biomacromolecules*, vol. 20, 9, 3324-3332 (2019);
- Preparation of PHA including a native epoxide unit: 10.1016/S1381-5148(97)00024-2); *Reactive and Functional Polymers*, vol. 34, 1, 65-77 (1997)

Example of functionalization of PHA copolymers according to the invention starting from a PHA copolymer bearing a hydrocarbon-based chain containing a nucleofugal group, according to Scheme 3 below:

[Chem. 10]

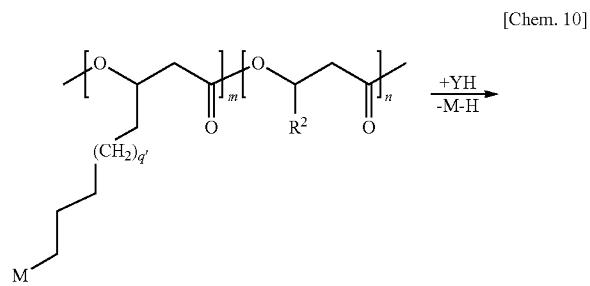

-continued

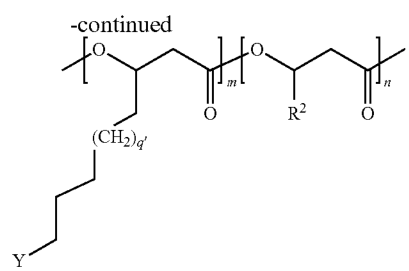

in which Scheme 3 Y, m, n, q' and $R^2$ are as defined in Scheme 1. M corresponds to an organic or inorganic nucleofugal group, which may be substituted with a nucleophilic group; preferably, said nucleophile is a heteroatom which is electron-donating via the +1 and/or +M effect such as O, S or N. Preferably, the nucleofugal group M is chosen from halogen atoms such as Br, and mesylate, tosylate or triflate groups. This is a reaction known to those skilled in the art. Mention may be made, for example, of the following document: 10.1016/j.ijbiomac.2016.11.118, *International Journal of Biological Macromolecules*, vol. 95, 796-808 (2017).

Example of functionalization of PHA copolymers according to the invention starting from a PHA copolymer bearing a hydrocarbon-based chain containing a cyano group, according to Scheme 4 below:

[Chem. 11]

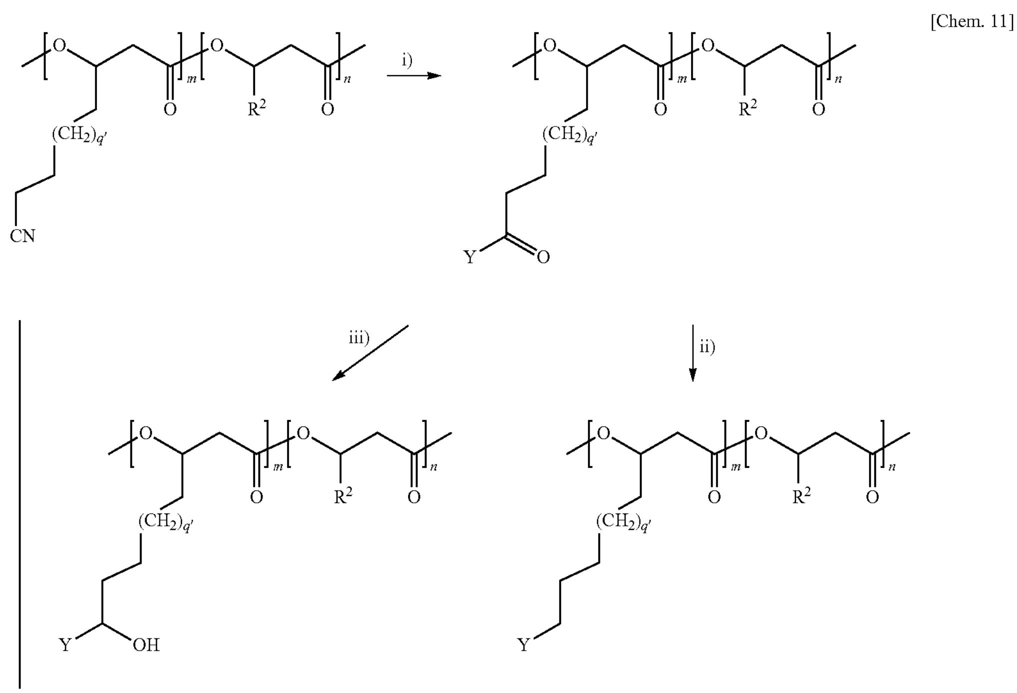

-continued

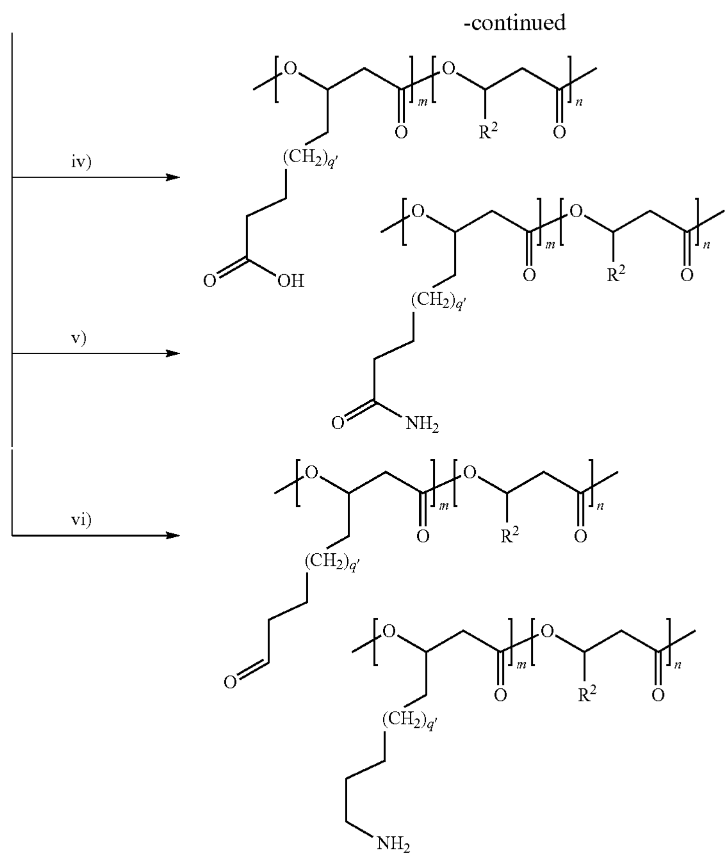

in which Scheme 4 Y, m, n, q' and R2 are as defined in Scheme 1.

In a first step i), the PHA copolymer bearing a side chain containing a cyano or nitrile group reacts with an organoalkali metal or organomagnesium compound Y—MgHal, Y—Li or Y—Na, followed by hydrolysis to give the PHA copolymer bearing a side chain containing a group Y grafted with a ketone function. The ketone function may be converted into a thio ketone by thionation, for example with S8 in the presence of amine, or with Lawesson's reagent. Said thio ketone, after total reduction ii) (for example by Clemmensen reduction) leads to the PHA copolymer bearing a side chain containing a group Y grafted with an alkylene group. Alternatively, said thio ketone may undergo a controlled reduction iii) with a conventional reducing agent to give the PHA copolymer bearing a side chain containing a group Y grafted with a hydroxyalkylene group. The cyano group of the starting PHA copolymer can react with water after hydration v) to give the amide derivative, or after hydrolysis iv) to the carboxyl derivative. The cyano group of the starting PHA copolymer may also, after reduction vi), give the amine derivative or the ketone derivative. The PHA copolymers bearing a hydrocarbon-based side chain containing a nitrile function are prepared via conventional methods known to those skilled in the art. Mention may be made, for example, of the document: 10.1016/0378-1097(92)90311-B, *FEMS Microbiology Letters*, vol. 103, 2-4, 207-214 (1992).

Example of functionalization of PHA copolymers according to the invention starting from a PHA copolymer bearing a hydrocarbon-based chain at the chain end, according to Scheme 5 below:

[Chem. 12]

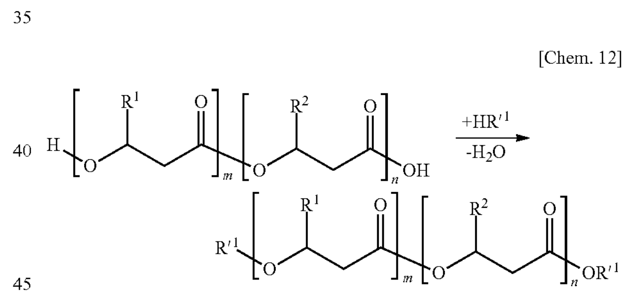

in which Scheme 5 $R^1$, $R^2$, m, n and Y are as defined previously, and $R'^1$ represents a hydrocarbon-based chain chosen from i) linear or branched $(C_1\text{-}C_{20})$alkyl, ii) linear or branched $(C_2\text{-}C_{20})$alkenyl, iii) linear or branched $(C_2\text{-}C_{20})$alkynyl; preferably, the hydrocarbon-based group is linear; said hydrocarbon-based chain being substituted with one or more atoms or groups chosen from: a) halogens such as chlorine or bromine, b) hydroxyl, c) thiol, d) (di)$(C_1\text{-}C_4)$(alkyl)amino, e) (thio)carboxyl, f) (thio)carboxamide —C(O)—$N(R_a)_2$ or —C(S)—$N(R_a)_2$, f) cyano, g) iso(thio)cyanate, h) (hetero)aryl such as phenyl or furyl, and i) (hetero)cycloalkyl such as anhydride, or epoxide, j) a cosmetic active agent chosen from coloured or uncoloured, fluorescent or non-fluorescent chromophores such as those derived from optical brighteners, or chromophores derived from UVA and/or UVB screening agents, and anti-ageing active agents.

These chain-end grafting agents on PHA polymers are known to those skilled in the art. Mention may be made, for example, of the following documents:

Preparation of PHA oligomers by thermal degradation: 10.1021/bm0156274; *Biomacromolecules*, vol. 3, 1, 219-224 (2002);

Preparation of PHA oligomers by transesterification: 10.1021/ma011420r, *Macromolecules*, vol. 35, 3, 684-689 (2002);

Preparation of PHA oligomers by hydrolysis: 10.1016/0032-3861(94)90590-8 *Polymer* vol. 35, 19, 4156-4162 (1994);

Preparation of PHA oligomers by methanolysis: 10.1021/bm060981t, *Biomacromolecules*, vol. 8, 4, 1255-1265 (2007).

Mention may also be made of other methods known to those skilled in the art:

Synthesis and characterization of PHA grafted with ascorbic acid: 10.1016/j.ijbiomac.2018.11.052; *International Journal of Biological Macromolecules*, vol. 123: 7 (2019);

Preparation of PHB-b-PHO copolymers by polycondensation with divinyl adipate catalysed with a lipase: 10.1021/bm9011634, *Biomacromolecules*, vol. 10, 12, 3176-3181 (2009);

Synthesis of PHB-b-PHO copolymers coupled via a diisocyanate junction: 10.1021/ma012223v; *Macromolecules*, vol. 35, 13, 4946-4950 (2002);

Preparation of PHO oligomers on chitosan by condensation between the carboxylic acid end of the PHO and the amine functions of the chitosan: 10.1002/app.24276; *Journal of Applied Polymer Science*, vol. 103, 1, (2006);

Transesterification of PHAs with propargyl alcohol in order to produce PHA oligomers that are modifiable by "click" chemistry: 10.1016/j.reactfunctpolym.2011.12.005; *Reactive and Functional Polymers*, vol. 72, 2, 160-167 (2012);

Preparation of PHO-b-PCL copolymer: 10.1002/mabi.200400104; *Macromolecular Bioscience*, vol. 4, 11 (2004);

Preparation of PHO-b-PEG copolymer: 10.1002/macp.201000562; *Macromolecular Chemistry and Physics*; vol. 212, 3, (2010);

Epoxidation of chain-end unsaturation and chain-end grafting of acid: 10.14314/polimery.2017.317; *Polimery*, vol. 62, 4, 317-322 (2017);

Grafting of organosiloxane unit at chain end onto PHA: 10.1016/j.reactfunctpolym.2014.09.008; *Reactive and Functional Polymers*, vol. 84, 53-59 (2014).

The combination of grafted PHA copolymers of the invention described previously, according to Scheme 6:

[Chem. 13]

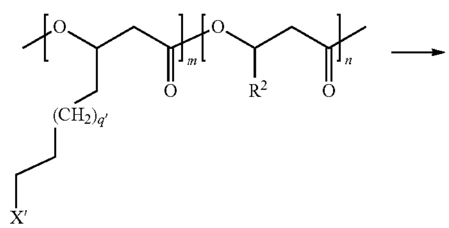

-continued

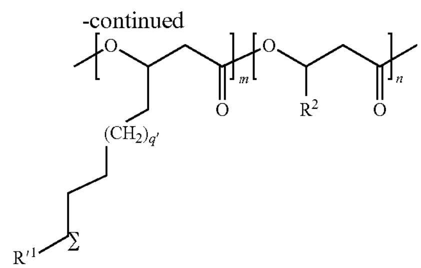

in which Scheme 6 $R'^1$, $R^2$, m, n and Y are as defined previously, and X' represents a reactive atom or group that is capable of reacting with an electrophilic $\mathcal{E}$ or nucleophilic $\mathcal{N}u$ atom or group to create a Σ covalent bond; if X' is an electrophilic or nucleofugal group, then it can react with a reagent $R'^1$-$\mathcal{N}u$; if X' is a nucleophilic group $\mathcal{N}u$, then it can react with $R'^1$-$\mathcal{E}$ to create a Σ covalent bond;

By way of example, the Σ covalent bonds or bonding group that may be generated are listed in the table below, from condensation of electrophiles with nucleophiles:

TABLE 1

| Electrophiles $\mathcal{E}$ | Nucleophiles $\mathcal{N}u$ | Covalent bonds |
|---|---|---|
| Activated esters* | Amines | Carboxamides |
| Acyl azides ** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salt thereof | Thiols | Thioethers |
| Sulfonic acids and salt thereof | Carboxylic acids | Esters |
| Sulfonic acids and salt thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazolakanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thicethers |
| Sulfonic esters | Amines | Alkylsmines |
| Sulfonic esters | Thiols | Thioethers |
| Sulfonic esters | Carboxylic acids | Esters |
| Sulfonic esters | Alcohols | Ethers |
| Sulfonyl halides | Amines | Sulfonamides |

*the activated esters of general formula —CO-LG, with LG representing a leaving group such as oxysuccinimidyl, oxybenzotriazolyl or aryloxy, optionally substituted;
**the acyl azides can rearrange to give isocyanate.

It is also possible, starting with a PHA functionalized on a side chain, to perform chain-end grafting in a second stage as described in Scheme 7. The reciprocal is also true, in which the chain-end grafting may be performed in a first stage, followed by performing functionalization of a functionalizable side chain in a second stage.

[Chem. 14]:

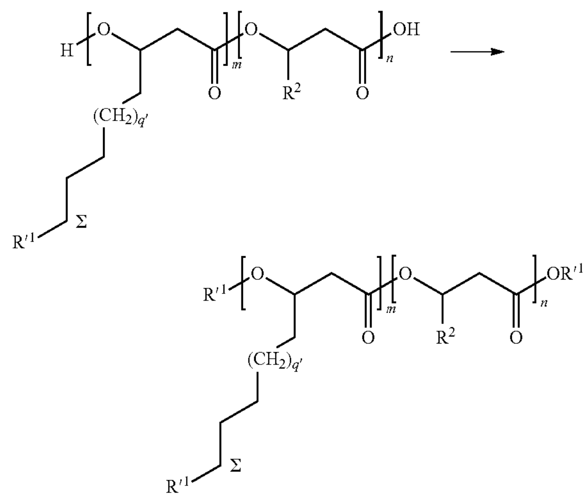

in which Scheme 7 $R'^1$, $R^2$, m, n and Y are as defined previously, and

All these chemical reactions are known to those skilled in the art. Mention may be made, for example, of the following documents:

Synthesis and preparation of PHAs modified with thiol-ene followed by reaction on the new grafted function: 10.1021/ma0304426; *Macromolecules*, vol. 37, 2, 385-389 (2004);

Grafting of PEG and of PLA onto PHAs functionalized with acids: 10.1002/marc.200900803 and 10.1002/mabi.200390033;

Synthesis and preparation of PHAs modified with polyethylene glycol dithiol: 10.1021/acs.biomac.9b00479.

b) The Surfactants

The composition also comprises b) one or more surfactants, which are preferably nonionic or ionic, or mixtures thereof.

The term "surfactant" means a compound which modifies the surface tension between two surfaces. The surfactant(s) are amphiphilic molecules, which have two parts of different polarity, one part being lipophilic (which retains fatty substances) which is apolar, the other hydrophilic part (miscible or soluble in water) being polar. The lipophilic part is generally a fatty chain, and the other water-miscible part is polar, and/or protic.

The term "ionic" means anionic, cationic, amphoteric or zwitterionic.

The term "fatty chain" means a linear or branched, saturated or unsaturated hydrocarbon-based chain comprising more than 6 atoms, preferably between 6 and 30 carbon atoms and preferably from 8 to 24 carbon atoms.

According to a first particular embodiment, the composition of the invention contains at least one nonionic surfactant. Among the nonionic surfactants according to the invention, mention may be made, alone or as mixtures, of fatty alcohols, α-diols and alkylphenols, these three types of compound being polyethoxylated, polypropoxylated or polyglycerolated and containing a fatty chain comprising, for example, 8 to 22 carbon atoms, the number of ethylene oxide or propylene oxide groups possibly ranging notably from 2 to 50 and the number of glycerol groups possibly ranging notably from 2 to 30. Mention may also be made of ethylene oxide and propylene oxide copolymers, condensates of ethylene oxide and of propylene oxide with fatty alcohols; polyethoxylated fatty amides preferably having from 2 to 30 ethylene oxide units, polyglycerolated fatty amides containing on average 1 to 5, and in particular 1.5 to 4, glycerol groups, ethoxylated fatty acid esters of sorbitan containing from 2 to 30 ethylene oxide units, fatty acid esters of sucrose, fatty acid esters of polyethylene glycol, alkylpolyglycosides, N-alkylglucamine derivatives, amine oxides such as $(C_{10}-C_{14})$alkylamine oxides or N-acylaminopropylmorpholine oxides.

More particularly, the surfactant(s) of the invention are chosen from nonionic surfactants, in particular chosen from: i) (poly)ethoxylated fatty alcohols; ii) glycerolated fatty alcohols; and iii) alkylpolyglycosides (APGs).

As regards the alkylpolyglycosides, these compounds are well known and may be represented more particularly by the following general formula:

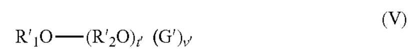

(V)

in which formula (V):

$R'_1$ represents a linear or branched alkyl and/or alkenyl radical, including from about 8 to 24 carbon atoms, or an alkylphenyl group whose linear or branched alkyl radical includes from 8 to 24 carbon atoms;

$R'_2$ represents an alkylene radical including from about 2 to 4 carbon atoms;

G' represents a sugar unit including from 5 to 6 carbon atoms;

t' is an integer inclusively between 0 and 10, preferably between 0 and 4, preferably between 0 and 4; and v' denotes an integer inclusively between 1 and 15.

Preferred alkylpolyglycosides according to the present invention are compounds of formula (V) in which $R_1$ more particularly denotes a linear or branched, saturated or unsaturated alkyl radical including from 8 to 18 carbon atoms, t' denotes a value ranging from 0 to 3 and even more particularly equal to 0, and G' may denote glucose, fructose or galactose, preferably glucose. The degree of polymerization, i.e. the value of v' in formula (V), may range from 1 to 15 and preferably from 1 to 4. The average degree of polymerization is more particularly between 1 and 2 and even more preferentially from 1.1 to 1.5.

The glycoside bonds between the sugar units are of 1-6 or 1-4 type and preferably of 1-4 type.

Compounds of formula (V) are notably represented by the products sold by the company Cognis under the names Plantaren® (600 CS/U, 1200 and 2000) or Plantacare® (818, 1200 and 2000). It is also possible to use the products sold by the company SEPPIC under the names Triton CG 110 (or Oramix CG 110) and Triton CG 312 (or Oramix® NS 10), the products sold by the company BASF under the name Lutensol GD 70 or those sold by the company Chem Y under the name AG10 LK.

It is also possible to use, for example, the $C_8/C_{16}$ alkyl 1,4-polyglucoside as an aqueous 53% solution sold by Cognis under the reference Plantacare® 818 UP.

As regards the mono- or polyglycerolated surfactants, they preferably include on average from 1 to 30 glycerol groups, more particularly from 1 to 10 and in particular from 1.5 to 5 glycerol groups.

The monoglycerolated or polyglycerolated surfactants are preferably chosen from the compounds of the following formulae:

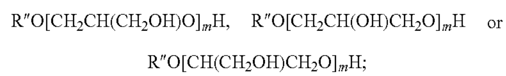

$R''O[CH_2CH(CH_2OH)O]_mH$, $R''O[CH_2CH(OH)CH_2O]_mH$ or $R''O[CH(CH_2OH)CH_2O]_mH$;

in which formulae R" represents a saturated or unsaturated, linear or branched hydrocarbon-based radical including from 8 to 40 carbon atoms and preferably from 10 to 30 carbon atoms; m is an integer between 1 and 30, preferably between 1 and 10, more particularly from 1.5 to 6.

R" may optionally comprise heteroatoms, for instance oxygen and nitrogen. In particular, R may optionally comprise one or more hydroxyl and/or ether and/or amide groups. R" preferably denotes optionally mono- or polyhydroxylated $C_{10}$-$C_{20}$ alkyl and/or alkenyl radicals.

Use may be made, for example, of the polyglycerolated (3.5 mol) hydroxylauryl ether sold under the name Chimexane® NF from Chimex.

The (poly)ethoxylated fatty alcohols that are suitable for use in the invention are more particularly chosen from alcohols including from 8 to 30 carbon atoms and preferably from 12 to 22 carbon atoms.

The (poly)ethoxylated fatty alcohols more particularly contain one or more linear or branched, saturated or unsaturated hydrocarbon-based groups, comprising 8 to 30 carbon atoms, which are optionally substituted, in particular with one or more (in particular 1 to 4) hydroxyl groups. If they are unsaturated, these compounds may comprise one to three conjugated or unconjugated carbon-carbon double bonds.

The (poly)ethoxylated fatty alcohol(s) preferably have the following formula (VI):

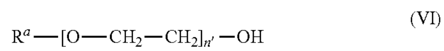

$$R^a—[O—CH_2—CH_2]_{n'}—OH \quad (VI)$$

in which formula (VI):

- $R^a$ represents a linear or branched $C_1$-$C_{40}$ alkyl or linear or branched $C_2$-$C_{30}$ alkenyl (preferentially $C_8$-$C_{30}$ alkyl) group; and
- n' is an integer between 1 and 200 inclusive, preferentially between 2 and 50 and more particularly between 2 and 30 inclusive, such as 20.

The (poly)ethoxylated fatty alcohols are more particularly fatty alcohols including from 8 to 22 carbon atoms and oxyethylenated with 1 to 30 mol of ethylene oxide (1 to 30 EO). Among these, mention may be made more particularly of lauryl alcohol 2 EO, lauryl alcohol 3 EO, decyl alcohol 3 EO, decyl alcohol 5 EO and oleyl alcohol 20 EO.

Mixtures of these (poly)oxyethylenated fatty alcohols may also be used.

Preferentially, the nonionic surfactants are chosen from ($C_6$-$C_{24}$)alkyl(poly)glycosides, and more particularly ($C_3$-$C_{13}$)alkyl(poly)glycosides, ethoxylated $C_8$-$C_{30}$ fatty acid esters of sorbitan, polyethoxylated $C_8$-$C_{30}$ fatty alcohols and polyoxyethylenated $C_8$-$C_{30}$ fatty acid esters, these compounds preferably containing from 2 to 150 mol of ethylene oxide, and mixtures thereof.

Among the nonionic surfactants, use is preferably made of $C_6$-$C_{24}$ alkyl polyglucosides and (poly)ethoxylated fatty alcohols, and $C_8$-$C_{16}$ alkyl polyglucosides are more particularly used.

The total amount of nonionic surfactants preferably ranges from 0.01% to 60% by weight relative to the total weight of the composition, preferably from 0.5% to 30% by weight and more particularly from 2% to 10% by weight relative to the total weight of the composition of the invention.

According to a particular embodiment of the invention, the composition comprises one or more ionic surfactants.

According to a particular embodiment of the invention, the composition comprises one or more cationic surfactants. They are advantageously chosen from optionally polyoxyalkylenated primary, secondary or tertiary fatty amine salts, quaternary ammonium salts, and mixtures thereof.

As quaternary ammonium salts, mention may notably be made of:

the quaternary ammonium salts of formula (VII):

[Chem. 15]

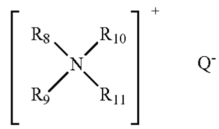

(VII)

in which formula (VII):

- the groups $R_8$ to $R_{11}$, which may be identical or different, represent a linear or branched aliphatic group including from 1 to 30 carbon atoms, or an aromatic group such as aryl or alkylaryl, at least one of the groups $R_3$ to $R_{11}$ including from 8 to 30 carbon atoms and preferably from 12 to 24 carbon atoms, it being possible for the linear or branched aliphatic groups to include heteroatoms notably such as oxygen, nitrogen or sulfur, these heteroatoms being non-adjacent, and halogens; and
- $Q^-$ is an anionic counterion notably chosen from i) halides such as bromides, chlorides, iodides or fluorides, ii) phosphates, iii) acetates, iv) lactates, v) ($C_1$-$C_4$)alkyl sulfates, vi) ($C_1$-$C_4$)alkylsulfonates and vii) ($C_1$-$C_4$)alkylarylsulfonates.

Mention may notably be made of tetraalkylammonium halides, notably chlorides, such as dialkyldimethylammonium or alkyltrimethylammonium chlorides in which the alkyl group includes from 12 to 22 carbon atoms, in particular from 14 to 20 carbon atoms, such as behenyltrimethylammonium chloride, distearyldimethylammonium chloride, cetyltrimethylammonium chloride (cetrimonium chloride) and benzyldimethylstearylammonium chloride. Mention may also be made of palmitylamidopropyltrimethylammonium or stearamidopropyldimethyl-(myristyl acetate)-ammonium halides, and notably chlorides; notably the product sold under the name Ceraphyl® 70 by the company Van Dyk.

Preferably, the cationic surfactants of formula (VII) that may be used denote alkyltrimethylammonium halides in which the alkyl group contains from 12 to 22 carbon atoms, more preferentially from 14 to 20 carbon atoms, and more particularly alkyltrimethylammonium chlorides such as behenyltrimethylammonium chloride or cetrimonium chloride;

the quaternary ammonium salts of imidazoline of formula (VIII):

[Chem. 16]

(VIII)

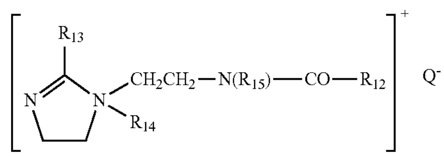

in which formula (VIII):

$R_{12}$ represents an alkenyl or alkyl group including from 8 to 30 carbon atoms, for example tallow or plant, preferably plant, fatty acid derivatives;

$R_{13}$ represents a hydrogen atom, a $C_1$-$C_4$ alkyl group or an alkenyl or alkyl group including from 8 to 30 carbon atoms, $R_{14}$ represents a $C_1$-$C_4$ alkyl group, $R_{15}$ represents a hydrogen atom or a $C_1$-$C_4$ alkyl group, Q− is as defined previously.

Preferably, $R_{12}$ and $R_{13}$ denote a mixture of alkenyl or alkyl groups including from 12 to 21 carbon atoms, for example derived from tallow fatty acids, $R_{14}$ denotes a methyl group and $R_{15}$ denotes a hydrogen atom. Such a product is sold, for example, under the name Rewoquat® W75 or W90 by the company Evonik.

quaternary di- or triammonium salts of formula (IX):

[Chem. 17]

(IX)

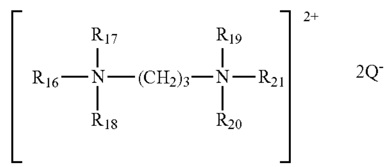

in which formula (IX):

$R_{16}$ represents an alkyl group including from 16 to 30 carbon atoms, which is optionally hydroxylated and/or optionally interrupted with one or more oxygen atoms, $R_{17}$ represents hydrogen, an alkyl group including from 1 to 4 carbon atoms or a group —$(CH_2)_3$—N*($R_{16a}$)($R_{17a}$)($R_{18a}$); $R_{16a}$, $R_{17a}$ and $R_{18a}$, which may be identical or different, denoting hydrogen or an alkyl group including from 1 to 4 carbon atoms, $R_{18}$, $R_{19}$, $R_{20}$ and $R_{21}$, which may be identical or different, denote hydrogen or an alkyl group including from 1 to 4 carbon atoms, and $Q^-$ is as defined previously.

Such compounds are, for example, Finquat CT-P (Quaternium 89) and Finquat CT (Quaternium 75), sold by the company Finetex;

quaternary ammonium salts containing one or more ester functions, of formula (X) below:

[Chem 18]

(X)

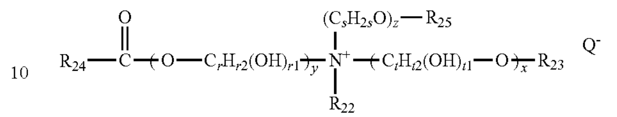

in which formula (X):

$R_{22}$ is chosen from $C_1$-$C_6$ alkyl groups and $C_1$-$C_6$ hydroxyalkyl or dihydroxyalkyl groups;

$R_{23}$ is chosen from the group $R_{26}$—C(O)—; linear or branched, saturated or unsaturated $C_1$-$C_{22}$ hydrocarbon-based groups $R_{27}$; and a hydrogen atom;

$R_{25}$ is chosen from the group $R_{28}$—C(O)—; linear or branched, saturated or unsaturated $C_1$-$C_6$ hydrocarbon-based groups $R_{29}$; and a hydrogen atom;

$R_{24}$, $R_{26}$ and $R_{28}$, which may be identical or different, are chosen from linear or branched, saturated or unsaturated $C_7$-$C_{21}$ hydrocarbon-based groups;

r, s and t, which may be identical or different, are integers ranging from 2 to 6;

r1 and t1, which may be identical or different, are equal to 0 or 1;

y is an integer ranging from 1 to 10;

x and z, which may be identical or different, are integers ranging from 0 to 10, $Q^-$ is as defined previously;

it being understood that r2+r1=2r and t1+t2=2t, and that the sum x+y+z ranges from 1 to 15, with the proviso that when x=0 then $R_{23}$ denotes $R_{27}$ and that when z=0 then $R_{25}$ denotes $R_{29}$.

The alkyl groups $R_{22}$ may be linear or branched, preferably linear. Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may comprise from 12 to 22 carbon atoms, or else may comprise from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched $C_{11}$-$C_{21}$ alkyl and alkenyl groups.

Preferably, x and z, which may be identical or different, are equal to 0 or 1. Advantageously, y is equal to 1.

Preferably, r, s and t, which may be identical or different, are equal to 2 or 3, and even more particularly are equal to 2.

The anionic counterion $Q^-$ is preferably a halide, preferably chloride, bromide or iodide, a ($C_1$-$C_4$)alkyl sulfate, a ($C_1$-$C_4$)alkylsulfonate or a ($C_1$-$C_4$)alkylarylsulfonate, a methanesulfonate, a phosphate, a nitrate, a tosylate, an anion derived from organic acid such as an acetate or a lactate or any other anion that is compatible with the ammonium bearing an ester function. The anion $Q^-$ is more particularly a chloride, a methyl sulfate or an ethyl sulfate.

Use is made more particularly, in the composition according to the invention, of the ammonium salts of formula (X) in which:

$R_{22}$ denotes a methyl or ethyl group, x and y are equal to 1, z is equal to 0 or 1, r, s and t are equal to 2, $R_{23}$ is chosen from the group $R_{26}$—C(O)—; methyl, ethyl or $C_{14}$-$C_{22}$ hydrocarbon-based groups, and a hydrogen atom, $R_{25}$ is chosen from the group $R_{28}$—C(O)—; and a hydrogen atom, $R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (X), mention may be made of the salts, notably the halides such as chloride, or the ($C_1$-$C_6$)alkyl sulfates such as methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures notably of plant or animal origin, or by transesterification of the methyl esters thereof. This esterification may be followed by quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin. Such compounds are sold, for example, under the names Dehyquart® by the company Henkel, Stepanquat® by the company Stepan, Noxamium® by the company CECA or Rewoquat® WE 18 by the company Evonik.

The composition according to the invention may contain, for example, a mixture of quaternary ammonium monoester, diester and triester salts with a weight majority of diester salts. Use may also be made of the ammonium salts containing at least one ester function that are described in U.S. Pat. Nos. 4,874,554 and 4,137,180. Use may also be made of the behenoylhydroxypropyltrimethylammonium chloride sold, for example, by the company Kao under the name Quartamin BTC 131.

Preferably, the ammonium salts containing at least one ester function contain two ester functions.

Preferably, the surfactants are cationic and are chosen from those of formula (VII), (IX) or (X), and better still from cetyltrimethylammonium, behenyltrimethylammonium and dipalmitoylethylhydroxyethylmethylammonium salts and mixtures thereof; and more particularly from behenyltrimethylammonium chloride or methosulfate, cetyltrimethylammonium chloride or methosulfate, dipalmitoylethylhydroxyethylmethylammonium chloride or methosulfate, and mixtures thereof.

More preferentially, the cationic surfactant(s) according to the invention are chosen from those of formula (VII) and better still from alkyltrimethylammonium salts in which the alkyl group contains from 12 to 22 carbon atoms and more preferentially from 14 to 20 carbon atoms, and more particularly behenyltrimethylammonium salts, cetrimonium salts and in particular cetyltrimethylammonium chloride, behenyltrimethylammonium chloride or mixtures thereof in all proportions.

According to another particular embodiment of the invention, the composition comprises one or more anionic surfactants.

The term "anionic surfactant" means a surfactant including, as ionic or ionizable groups, only anionic groups. These anionic groups are preferably chosen from the groups —C(O)OH, —C(O)O$^-$, —$SO_3$H, —S$(O)_2$O$^-$, —OS$(O)_2$OH, —OS$(O)_2$O$^-$, —P(O)$OH_2$, —P$(O)_2$O$^-$, —P(O)$O_2$$^-$, —P$(OH)_2$, ═P(O)OH, —P(OH)O$^-$, ═P(O)O$^-$, ═POH, ═PO$^-$, the anionic parts comprising a cationic counterion such as those derived from an alkali metal, an alkaline-earth metal, or an amine or an ammonium.

As examples of anionic surfactants that may be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefin sulfonates, paraffin sulfonates, alkyl sulfosuccinates, alkyl ether sulfosuccinates, alkylamide sulfosuccinates, alkyl sulfoacetates, acylsarcosinates, acylglutamates, alkyl sulfosuccinamates, acylisethionates and N-acyltaurates, polyglycoside polycarboxylic acid and alkyl monoester salts, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds comprising from 6 to 24 carbon atoms and the aryl group denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salts.

Examples of amino alcohol salts that may notably be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Use is preferably made of alkali metal or alkaline-earth metal salts, and in particular sodium or magnesium salts.

Among the anionic surfactants mentioned, use is preferably made of ($C_6$-$C_{24}$)alkyl sulfates, ($C_6$-$C_{24}$)alkyl ether sulfates comprising from 2 to 50 ethylene oxide units, notably in the form of alkali metal, ammonium, amino alcohol and alkaline-earth metal salts, or a mixture of these compounds.

In particular, it is preferred to use ($C_{12}$-$C_{20}$)alkyl sulfates, ($C_{12}$-$C_{20}$)alkyl ether sulfates comprising from 2 to 20 ethylene oxide units, notably in the form of alkali metal, ammonium, amino alcohol and alkaline-earth metal salts, or a mixture of these compounds. Better still, it is preferred to use sodium lauryl ether sulfate in particular those containing 2.2 mol of ethylene oxide, more preferentially ($C_{12}$-$C_{20}$) alkyl sulfates such as the lauryl sulfate of an alkali metal such as sodium.

According to a particular embodiment of the invention, the composition comprises one or more amphoteric or zwitterionic surfactants. The amphoteric or zwitterionic surfactants of the invention are not silicone-based, and are notably optionally quaternized secondary or tertiary aliphatic amine derivatives, in which the aliphatic group is a linear or branched chain including from 8 to 22 carbon atoms, said amine derivatives containing at least one anionic group, for instance a carboxylate, sulfonate, sulfate, phosphate or phosphonate group. Mention may be made in particular of ($C_8$-$C_{20}$)alkyl betaines, sulfobetaines, ($C_8$-$C_{20}$) alkylamido($C_3$-$C_8$)alkyl betaines and ($C_8$-$C_{20}$)alkylamido ($C_6$-$C_8$)alkyl sulfobetaines.

Among the amphoteric or zwitterionic surfactants mentioned above, use is preferably made of (($C_8$-$C_{20}$)alkylbetaines such as cocoylbetaine, and ($C_8$-$C_{20}$)alkylamido($C_3$-$C_8$)alkylbetaines such as cocamidopropylbetaine, and mixtures thereof. More preferentially, the amphoteric or zwitterionic surfactant(s) are chosen from cocamidopropylbetaine and cocoylbetaine.

According to a particular embodiment, the composition comprises one or more cationic surfactants, in particular optionally polyoxyalkylenated primary, secondary or tertiary fatty amine salts, or quaternary ammonium salts, and mixtures thereof. Among the cationic surfactants that may be present in the composition according to the invention, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

According to a particular embodiment of the invention, the surfactant(s) have a high HLB, i.e. greater than 10 and preferably greater than 15.

According to another particular embodiment of the invention, the surfactant(s) have a low HLB, i.e. less than or equal to 10, more preferentially between 1 and 6.

The term "HLB" or Hydrophilic-Lipophilic Balance means a hydrophilic/lipophilic balance value, according to the definition given by W. C. Griffin (Classification of Surface-Active Agents by HLB, *Journal of the Society of Cosmetic Chemists* 1, 311 (1949). It is possible to calculate the HLB via the conventional method of J. T. Davies (Davies J. T., *A quantitative kinetic theory of emulsion type, I. Physical chemistry of the emulsifying agent*, Gas/Liquid and Liquid/Liquid Interface. Proceedings of the International Congress of Surface Activity (1957): 426-438).

TABLE 2

| Compound | HLB |
|---|---|
| Calcium Stearoyl lactylate | HLB 5.1 |
| Ceteareth-20 | HLB 15.2 |
| Cetearyl Glucoside | HLB 11 |
| Ceteth-10 | HLB 12.9 |
| Ceteth-2 | HLB 5.3 |
| Ceteth-20 | HLB 15.7 |
| Cocamide MEA | HLB 13.5 |
| Decaglycerol Laurate | HLB 14 |
| Dermofeel PP (Polyglyceryl-3 Palmitate) | HLB 9 |
| Dipolyhydroxystearate | HLB 5.5 |
| Base emulsifier (INCI: glyceryl monostearate) | HLB 3.8 |
| Emulsifier L (INCI: Alkyl alcohol and Alkyl glucoside) | HLB 10.3 |
| Emulsifier MF (INCI: sodium stearoyl lactylate) | HLB 17 |

TABLE 2-continued

| Compound | HLB |
|---|---|
| Emulsifier VE (INCI: glyceryl stearate) | HLB 3.8 |
| Diacetyltartaric acid monoglyceride ester | HLB 9.2 |
| Succinic acid monoglyceride ester | HLB 5.3 |
| Sugar ester | HLB 11 |
| Sugar ester (INCI: Sucrose stearate) | HLB 15 |
| Glyceryl Monostearate | HLB 3.8 |
| Glyceryl Laurate | HLB 5.2 |
| Glyceryl Oleate | HLB 4 |
| Glyceryl Stearate | HLB 3.8 |
| Glyceryl Stearate (and) PEG-100 Stearate | HLB 11 |
| Glyceryl stearate citrate | HLB 11 |
| Glyceryl Stearate SE | HLB 5.8 |
| Glycol distéarate | HLB 1 |
| Glycol Stearete | HLB 2.9 |
| Hydrogenated palm glyceride (emulsifier TEGOMULS) | HLB 12 |
| Hydroxypropyl Oxidized Starch PG-Trimonium Chloride Polyglyceryl-10 Laurate | HLB 16 |
| Isoceteth-20 | HLB 15.7 |
| Isosteareth-20 | HLB 15 |
| L7D (Decaglyceryl Laurate) | HLB 14 |
| Glyceryl lactopelmitate | HLB 3.7 |
| Lauramide DEA | HLB 15 |
| Laureth-23 | HLB 18.9 |
| Laureth-4 | HLB 9.7 |
| Propylene Glycol Monolaurate | HLB 4.6 |
| Sorbitan Monolaurate | HLB 6.6 |
| Polyoxyethylene (20) Sorbitan Monooleate | HLB 15.8 |
| Polyoxyethylene (5) Sorbitan Monooleate | HLB 10.9 |
| Sorbitan Monopalmitate | HLB 6.6 |
| Diglyceryl Monostearate | HLB 5.5 |
| Glyceryl Monostearate | HLB 3.7 |
| Polyoxyethylene Sorbitan Monostearate | HLB 14.9 |
| Propylene Glycol Monostearate | HLB 1.8 |
| Sorbitan Monostesrate | HLB 5.7 |
| sorbitene Monostearate | HLB 4.7 |
| Triethanolamine Oleate | HLB 12 |
| Oleic acid | HLB 4.3 |
| Oleth-10 | HLB 12.4 |
| Oleth-10/Polyoxyl 10 Oleyl Ether NF | HLB 12.4 |
| Oleth-2 | HLB 4.9 |
| Oleth-20 | HLB 13.3 |
| P3R (Polyglyceryl-3 Polyricinoleate) | HLB 3.5 |
| PEG-100 Stearate | HLB 18.8 |
| PEG-20 Almond Glycerides | HLB 10 |
| PEG-20 Methyl Glucose Sesquistearate | HLB 15 |
| PEG-25 Hydrogenated Castor Oil | HLB 10.8 |
| PEG-30 Dipolyhydroxystearate | HLB 5.5 |
| PEG-4 Dilaurate | HLB 6 |
| PEG-40 Sorbitan Peroleate | HLB 9 |
| PEG-60 Almond Glycerides | HLB 15 |
| PEG-7 Glyceryl Cocoate | HLB 10 |
| PEG-7 Olivate | HLB 11 |
| PEG-8 Dioleate | HLB 8 |
| PEG-8 Laurate | HLB 13 |
| PEG-8 Oleate | HLB 11.6 |
| PEG-80 Sorbitan Laurate | HLB 19.1 |
| Polyethylene Glycol 400 Monostearate | HLB 11.6 |
| Polyglyceryl-2 Laurate | HLB 10 |
| Polyglyceryl-10 Leurate Aqua (diluted with 50% water) | HLB 16 |
| Polyglyceryl-2 Laureate | HLB 10 |
| Polyglyceryl-3 Laurate | HLB 11 |
| Polyglyceryl-3 Methyglucose Distearate | HLB 12 |
| Polyglyceryl-3 Palmitate | HLB 10 |
| Polyglyceryl-3 Ricinoleate | HLB 3.5 |
| Polyglyceryl-3 Polyricinoleate | HLB 4 |
| Polyglyceryl-3 Stearate | HLB 9 |
| Polyglyceryl-5 Laurate | HLB 13 |
| Polyglyceryl-6 Caprylate | HLB 11.5 |
| Polyglyceryl-6 Caprylate | HLB 11.5 |
| Polyoxyethylene-20 Sorbitan Monolaurate | HLB 16.7 |
| Polyoxyethylene-20 Sorbitan Monooleate | HLB 16 |
| Polyoxyethylene-20 Sorbitan Monopalmitate | HLB 15.8 |
| Polyoxyethylene-4 Lauryl Ether | HLB 9.5 |
| Polyoxyethylene-4 Sorbitan Monolaurate | HLB 13.3 |
| Polyoxyethylene-40 Stearate | HLB 16.9 |
| Polysorbate 20 | HLB 16.7 |

TABLE 2-continued

| Compound | HLB |
|---|---|
| Polysorbate 60 NF | HLB 14.9 |
| Polysorbate 80 | HLB 15 |
| Polysorbate 80 NF | HLB 15 |
| Polysorbate 85 | HLB 11 |
| Potassium oleate | HLB 20 |
| PPG-15 Stearyl Ether | HLB 7 |
| Propylene Glycol Monolsurate | HLB 4.5 |
| Propylene Glycol Monostearate | HLB 3.4 |
| Retinyl Palmitate | HLB 6 |
| Sabosorb MS (Sorbitane Monostearate) | HLB 4.7 |
| Saccharose Cocoste | HLB 6 |
| Sodium Lauryl Sulfate | HLB 40 |
| Sodium oleate | HLB 18 |
| Sodium stearoyl lactylate | HLB 8.3 |
| Sodium Stearoyl Lactylste | HLB 17 |
| Sorbitan Isostearate | HLB 4.7 |
| Sorbitan Laurate | HLB 8.8 |
| Sorbitan Monolaurate | HLB 8.6 |
| Sorbitan Monooleate | HLB 4.3 |
| Sorbiten Monopalmitate | HLB 6.7 |
| Sorbitan Monosterarate | HLB 4.7 |
| Sorbitan oleste | HLB 4.3 |
| Sorbitan sesquioleate | HLB 3.7 |
| Sorbitan stéarate | HLB 4.7 |
| Sorbitan Stearate (and) Sucrose Cocoate | HLB 6 |
| Sorbitan Trioleate | HLB 1.8 |
| Sorbitan Tristearate | HLB 2.1 |
| Stearamide MEA | HLB 11 |
| Steareth-100 | HLB 18.8 |
| Steareth-2 | HLB 4.9 |
| Steareth-20 | HLB 13.3 |
| Steareth-21 | HLB 15.5 |
| Sodium Stearoyllactylate | HLB 17 |
| Sodium stearyl-2-lactylate (SSL) | HLB 21 |

Preferably, the surfactant(s) in which b) the surfactant(s) of the invention are ionic, preferably anionic or cationic, more preferentially anionic of sulfate type and/or the surfactant(s) and b) have a high HLB value, i.e. greater than 10, preferably greater than 15.

More preferentially, the surfactant(s) are chosen from:

TABLE 3

| INCI name | HLB |
|---|---|
| Oxyethylenated (200E) sorbitan monopalmitate | 15.3 |
| Laureth-23 | 16.3 |
| Laureth-4 | 10 |
| polyglyceryl-4-isostearate | 5 |

According to a particular embodiment, the composition comprises a mixture of surfactants or several surfactants that are nonionic characterized by a high HLB value. Preferably, the surfactant(s) are chosen from:

When the surfactant(s) b) are composed of a mixture of at least one ionic surfactant and of at least one nonionic surfactant in all proportions.

Preferably, the ionic surfactant(s) are chosen from:

N-lauroyl sarcosinate of alkali metals or alkaline-earth metals such as sodium laureth sulfate of alkali metals or alkaline-earth metals such as sodium behenyltrimethylammonium halide, preferably chloride cetrimonium halide, preferably chloride dodecyl sulfate of alkali metals or alkaline-earth metals such as sodium N-cocoyl glycinate of alkali metals or alkaline-earth metals such as sodium and the nonionic surfactant(s) are chosen from:

4 OE and/or 23 OE polyoxyethylenated lauryl alcohols (laureth-23 and/or laureth-4)

polyoxyethylenated (20 OE) sorbitan monopalmitate polyglyceryl-4 isostearate.

According to a particular embodiment of the invention, the surfactant(s) are a mixture of nonionic surfactants in ratios such that the HLB of the mixture is a high HLB; preferably, the nonionic surfactants are chosen from:

polyglyceryl-4 isostearate

4 OE and/or 23 OE polyoxyethylenated lauryl alcohols (laureth-23 and/or laureth-4)

polyoxyethylenated (20 OE) sorbitan monopalmitate

Preferably, the surfactant(s) b) are only one type of surfactant, preferably ionic surfactant. Even more preferentially, the ionic surfactant is lauroyl sarcosinate.

The amount of the surfactant(s) included in the composition of the invention represents from 0.1% to 30% by weight, preferably from 1% to 20% by weight, and even more preferably from 2% to 10% by weight relative to the total weight of the composition.

In a second preferred variant of the invention, the composition comprises only one type of surfactant, which is preferably nonionic, characterized by a high HLB value, chosen from:

23 OE polyoxyethylenated lauryl alcohol (=laureth-23) and polyoxyethylenated sorbitan monopalmitate Even more preferentially, the surfactant(s) b) of the invention are characterized by a high HLB value, such as polyoxyethylenated sorbitan monopalmitate.

According to a preferred variant of the invention, the composition comprises a mixture of ionic surfactant and of nonionic surfactant preferably chosen from:

lauryl alcohols/alkali metal or alkaline-earth metal (such as sodium) N-lauroyl sarcosinate polyoxyethylenated with 4 OE and/or 23 OE in particular in proportions of from 1/99 to 99/1;

N-lauroyl sarcosinate of alkali metals or alkaline-earth metals such as sodium/polyoxyethylenated sorbitan monopalmitate in particular in proportions of from 1/99 to 99/1;

laureth sulfate of alkali metals or alkaline-earth metals such as sodium/lauryl alcohols polyoxyethylenated with 4 OE and/or 23 OE in particular in proportions of from 1/99 to 99/1;

laureth sulfate of alkali metals or alkaline-earth metals such as sodium/polyoxyethylenated sorbitan monopalmitate in particular in proportions of from 1/99 to 99/1;

behenyltrimethylammonium halide (such as chloride)/lauryl alcohols polyoxyethylenated with 4 OE and/or 23 OE in particular in proportions of from 1/99 to 99/1;

behenyltrimethylammonium halide (such as chloride)/polyoxyethylenated sorbitan monopalmitate in particular in proportions of from 1/99 to 99/1;

cetrimonium halide (such as chloride)/lauryl alcohols polyoxyethylenated with 4 OE and/or 23 OE in particular in proportions of from 1/99 to 99/1;

cetrimonium halide (such as chloride)/polyoxyethylenated sorbitan monopalmitate in particular in proportions of from 1/99 to 99/1;

dodecyl sulfate of alkali metals or alkaline-earth metals/lauryl alcohols polyoxyethylenated with 4 OE and/or 23 OE in particular in proportions of from 1/99 to 99/1;

dodecyl sulfate of alkali metals or alkaline-earth metals such as sodium/polyoxyethylenated sorbitan monopalmitate in particular in proportions of from 1/99 to 99/1;

N-cocoyl glycinate of alkali metals or alkaline-earth metals such as sodium/lauryl alcohols polyoxyethylenated with 4 OE and/or 23 OE in particular in proportions of from 1/99 to 99/1;

N-cocoyl glycinate of alkali metals or alkaline-earth metals such as sodium/polyoxyethylenated sorbitan monopalmitate in particular in proportions of from 1/99 to 99/1;

N-lauroyl sarcosinate of alkali metals or alkaline-earth metals such as sodium/polyglyceryl-4 isostearate in particular in proportions of from 1/99 to 99/1;

laureth sulfate/polyglyceryl-4 isostearate in particular in proportions of from 1/99 to 99/1;

behenyltrimethylammonium halide such as chloride/polyglyceryl-4 isostearate in particular in proportions of from 1/99 to 99/1;

cetrimonium halide such as chloride/polyglyceryl-4 isostearate in particular in proportions of from 1/99 to 99/1;

dodecyl sulfate of alkali metals or alkaline-earth metals such as sodium/polyglyceryl-4 isostearate in particular in proportions of from 1/99 to 99/1; and sodium N-cocoyl glycinate/polyglyceryl-4 isostearate in particular in proportions of from 1/99 to 99/1.

Preferably, the surfactant(s) b) of the composition are a mixture of surfactants chosen from:

dodecyl sulfate of alkali metals or alkaline-earth metals such as sodium/polyoxyethylenated sorbitan monopalmitate in particular in proportions of 10/90;

dodecyl sulfate of alkali metals or alkaline-earth metals such as sodium/polyoxyethylenated sorbitan monopalmitate in particular in proportions of 50/50;

N-lauroyl sarcosinate of alkali metals or alkaline-earth metals such as sodium/polyoxyethylenated sorbitan monopalmitate in proportions of 90/10;

laureth of alkali metals or alkaline-earth metals such as sodium/polyoxyethylenated sorbitan monopalmitate in particular in proportions of 90/10;

laureth sulfate of alkali metals or alkaline-earth metals such as sodium/polyoxyethylenated sorbitan monopalmitate in particular in proportions of 50/50;

cetrimonium halide (preferably chloride)/polyoxyethylenated sorbitan monopalmitate in particular in proportions of 10/90;

behenyltrimethylammonium halide (preferably chloride)/polyoxyethylenated sorbitan monopalmitate in particular in proportions of 10/90;

N-lauroyl sarcosinate of alkali metals or alkaline-earth metals such as sodium/polyglyceryl-4 isostearate in particular in proportions of 90/10;

N-lauroyl sarcosinate of alkali metals or alkaline-earth metals such as sodium/polyglyceryl-4 isostearate in particular in proportions of 10/90;

laureth sulfate of alkali metals or alkaline-earth metals such as sodium/polyglyceryl-4 isostearate in particular in proportions of 10/90;

laureth sulfate of alkali metals or alkaline-earth metals such as sodium/polyglyceryl-4 isostearate in particular in proportions of 50/50;

cetrimonium halide (preferably chloride)/polyglyceryl-4 isostearate in particular in proportions of 10/90; and behenyltrimethylammonium (preferably chloride)/polyglyceryl-4 isostearate in particular in proportions of 10/90.

Even more preferentially, the mixture of surfactants is chosen from the following combinations:

laureth sulfate of alkali metals or alkaline-earth metals such as sodium/polyoxyethylenated sorbitan monopalmitate in particular in proportions of from 90/10 to 50/50, preferably from 75/25 to 50/50 and more preferentially 50/50; and;

laureth sulfate of alkali metals or alkaline-earth metals such as sodium/polyglyceryl-4 isostearate in particular in proportions of from 10/90 to 90/10, preferably from 25/75 to 75/25 and more preferentially 50/50.

In a fourth preferred variant of the invention, the compositions of the invention are formed from 2% to 50%, preferentially 10% to 40% by weight of surfactants, preferably nonionic surfactants, in proportions such that the mixture is characterized by a high HLB value, i.e. chosen from the following mixtures:

laureth 23 and laureth 4 in particular in a proportion of (80/20) to obtain an HLB value for the mixture of 15.1; and laureth 23 and laureth 4 in particular in a proportion of (95/5) to obtain an HLB value for the mixture of 16.

More preferentially, the surfactant(s) b) are a mixture of surfactants in particular chosen from:

laureth 23 and laureth 4 in particular in a proportion of (80/20) to obtain an HLB value for the mixture of 15.1.

The term "nonionic surfactant" preferably means Laureth-23, Laureth-4, oxyethylenated (20 OE) sorbitan monopalmitate, or polyglyceryl-4 isostearate.

As examples of nonionic surfactants with a high HLB value, examples that may be mentioned include: oxyethylenated (20 OE) sorbitan monopalmitate and laureth-23.

As examples of nonionic surfactants with a low HLB value, examples that may be mentioned include laureth-4 and polyglyceryl-4 isostearate.

According to another particular embodiment of the invention, the composition comprises one or more silicone surfactants.

The composition according to the invention may comprise one or more silicone surfactants. The silicone surfactants may be water-soluble, spontaneously water-dispersible or water-insoluble. Preferably, they are water-soluble or spontaneously water-dispersible.

Preferably, the silicone surfactants are oxyalkylenated, preferably oxyethylenated.

Composition b) may comprise silicone surfactants. The silicone surfactants may be chosen from the compounds of formulae (XI), (XII), (XIII), (XIV) and (XV) below:

[Chem. 19]

(XI)

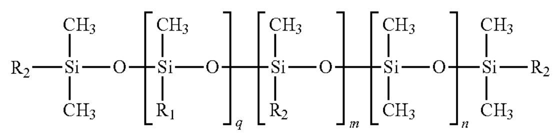

[Chem. 20]

(XII)

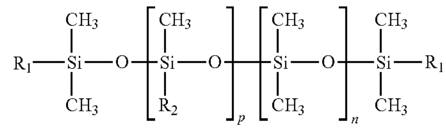

-continued

[Chem. 21]

(XIII)

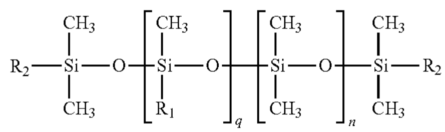

[Chem. 22]

(XIV)

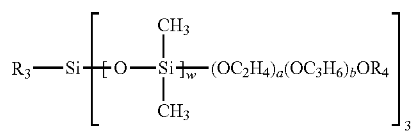

[Chem. 22]

(XV)

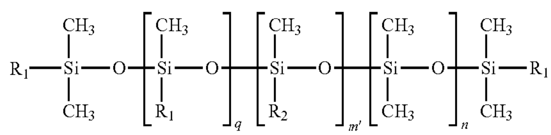

in which formulae (XI) to (XV):

$R_1$, which may be identical or different, represents a linear or branched C1-C30 alkyl radical or a phenyl radical;

R3 and R4, which may be identical or different, denote a linear or branched C1 to C12 alkyl radical and preferably a methyl radical;

R2, which may be identical or different, represent a group —$(CH_2)$c-O—$(C_2H_4O)$a'-$(C_6H_6O)$b'-R5 or —$(CH_2)$c-O—$(C_4H_8O)$a'-R5 in which a' ranges from 0 to 50; b' ranges from 0 to 50 and a'+b' is greater than or equal to 1; c ranges from 0 to 4; and R5, which may be identical or different, is chosen from a hydrogen atom, a linear or branched alkyl group including from 1 to 12 carbon atoms; a linear or branched alkoxy group including from 1 to 6 carbon atoms; a linear or branched acyl group including from 2 to 12 carbon atoms; a hydroxyl group, a group —SO3M, a group —OCOR6, a C1-C6 aminoalkoxy group optionally substituted on the amine with one or two C1-C4 alkyl radicals, optionally bearing at least one hydroxyl group; a C2-C6 aminoacyl group optionally substituted on the amine with one or two C1-C4 alkyl radicals, optionally bearing at least one hydroxyl group; a group —NHCH2CH2OOOM, a group —N(CH2CH2OOOM)2; a C1-C12 aminoalkyl group, optionally substituted on the amine and on the alkyl chain with one or two C1-C4 alkyl radicals, optionally bearing at least one hydroxyl group, a C1-C30 carboxyacyl group, a phosphono group optionally substituted with one or two substituted C1-C12 aminoalkyl groups, a group —CO$(CH_2)$dCOOM, a group —OCO-CHR7$(CH_2)$dCOOM, a group —NHCO$(CH_2)$dOH, a group —NH3Y; in which M, which may be identical or different, denotes a hydrogen atom, Na, K, Li, NH4 or an organic amine; R6 denotes a linear or branched C1-C30 alkyl group; R7 denotes a hydrogen atom or a group SO3M; d ranges from 1 to 10; and Y represents an anion such as a halide (chloride, bromide), a sulfate or a carboxylate (acetate, lactate, citrate);

m ranges from 0 to 20;

m' ranges from 1 to 20;

n ranges from 0 to 500;

p ranges from 1 to 50;

q ranges from 0 to 20;

w varies from 1 to 100;

a ranges from 0 to 50; b ranges from 0 to 50; and a+b is greater than or equal to 1, in formula (XIV).

Preferably, the silicone surfactants correspond to the general formula (XI) or (XII) as defined above, and more particularly correspond to formula (XI) or (XII) in which at least one and preferably all of the following conditions are satisfied:

R1 denotes a methyl group;

R2, c=2 or 3;

R2, R5 represents a hydrogen atom, a methyl group or an acetyl group, preferably a hydrogen atom;

R2, a' ranges from 1 to 25 and more particularly from 2 to 25;

R2, b' ranges from 0 to 25, preferably from 10 to 20;

n ranges from 0 to 100;

p ranges from 1 to 20.

Mention may notably be made of the silicone surfactants sold under the trade names Fluid DC 193 and DC 5225C by the company Dow Corning, Silwet® L 77 by the company OSI, and Mazil® 756 by the company Mazer PPG.

Preferably, the silicone surfactant is a mixture of silicones comprising hydrophilic grafts. It is preferentially composed of a mixture of oxyethylenated (OE) oxypropylenated (OP) (18 OE/18 OP) polydimethylsiloxane, cyclopentadimethylsiloxane and water (10/88/2), such as the product sold under the name Dow Corning 5225C Formulation Aid by the company Dow Corning.

The composition according to the invention may comprise the silicone surfactants in an amount ranging from 0.1% to 30% by weight, notably from 1% to 20% by weight relative to the total weight of the composition.

According to a particular embodiment of the invention, the composition comprises one or more surfactants chosen from:

N-lauroyl sarcosinate of alkali metals or alkaline-earth metals such as sodium;

laureth sulfate of an alkali metal or alkaline-earth metal such as sodium;

behenyltrimethylammonium halide (preferably chloride);

cetrimonium halide (preferably chloride);

N-cocoyl glycinate of an alkali metal or alkaline-earth metal such as sodium;

decyl sulfate of alkali metals or alkaline-earth metals such as sodium;

lauroyl sarcosinate of alkali metals or alkaline-earth metals such as sodium;

[Chem. 23]

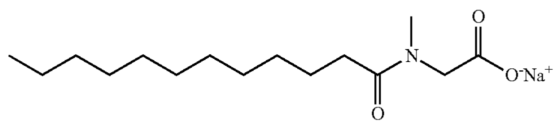

lauryl ether sulfate of alkali metals or alkaline-earth metals such as sodium;

[Chem. 24]

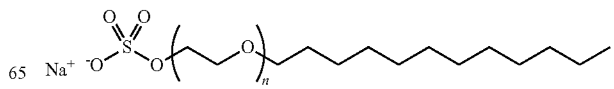

sarcosinates and acylglycinates of alkali metals or alkaline-earth metals such as sodium

[Chem. 25]

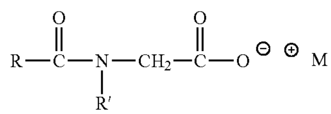

Preferably, the surfactant(s) of the invention are ionic, preferably anionic or cationic. According to a particular embodiment of the invention, the surfactant(s) have a high HLB, i.e. greater than 10 and preferably greater than 15.

According to a particular embodiment, the composition comprises one or more nonionic surfactants characterized by a high HLB value. Preferably, the surfactants are chosen from:

23 OE polyoxyethylenated lauryl alcohols (laureth-23) and polyoxyethylenated sorbitan monopalmitate The surfactant(s) represent in total particularly from 0.01% to 60% by weight, preferably from 0.5% to 30% by weight and even more preferentially from 1% to 20% by weight, relative to the total weight of the composition.

The amount of surfactants b) represents 0.1% to 30% by weight relative to the total amount of the composition, preferably 1% to 20% and even more preferably 2% to 10%.

c) The Fatty Substances

According to a particular embodiment of the invention, the composition also comprises one or more fatty substances.

The composition may also comprise water. Preferably, the composition of the invention predominantly comprises on a weight basis one or more fatty substances versus the amount by weight of water.

The term "fatty substance" means an organic compound that is insoluble in water at ordinary room temperature (25° C.) and at atmospheric pressure (760 mmHg) (solubility of less than 5%, preferably 1% and even more preferentially 0.1%). They bear in their structure at least one hydrocarbon-based chain including at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

The fatty substance(s) of the invention are of natural or synthetic origin, preferably natural, more preferentially of plant origin. These fatty substances are preferably neither polyoxyethylenated nor polyglycerolated. They are different from fatty acids since salified fatty acids constitute soaps which are generally soluble in aqueous media.

According to a particular embodiment of the invention, the composition comprises one or more fatty substances that are not liquid at 25° C. and at atmospheric pressure.

The Wax(es)

According to a particular embodiment, the composition of the invention comprises one or more waxes.

The term "wax" means a lipophilic compound that is solid at room temperature (25° C.), with a reversible solid/liquid change of state, having a melting point of greater than or equal to 30° C., which may be up to 200° C. and notably up to 120° C.

In particular, the wax(es) that are suitable for use in the invention may have a melting point of greater than or equal to 45° C. and in particular of greater than or equal to 55° C.

The composition according to the invention preferably comprises a content of wax(es) ranging from 3% to 20% by weight relative to the total weight of the composition, in particular from 5% to 15% and more particularly from 6% to 15%.

According to a particular form of the invention, the composition of the invention is solid, in particular anhydrous. It may then be in stick form; use will be made of polyethylene microwaxes in the form of crystallites with an aspect ratio at least equal to 2, and with a melting point ranging from 70 to 110° C. and preferably from 70 to 100° C., so as to reduce or even eliminate the presence of strata in the solid composition. These crystallites in needle form and notably the dimensions thereof may be characterized visually according to the following method.

The Pasty Compound(s)

According to a particular embodiment, the composition of the invention comprises one or more pasty compounds.

For the purposes of the present invention, the term "pasty compound" means a lipophilic fatty compound that undergoes a reversible solid/liquid change of state, having anisotropic crystal organization in the solid state, and including, at a temperature of 23° C., a liquid fraction and a solid fraction.

Preferably, the composition contains one or more fatty substances c) which are liquid fatty substances; in particular, the liquid fatty substance(s) are chosen from non-silicone oils; preferably, the liquid fatty substance(s) are chosen from:

ester oils, carbonate oils;

apolar branched hydrocarbon-based oils containing from 8 to 14 carbon atoms, as a mixture with a monoalcohol containing from 2 to 6 carbon atoms in a monoalcohol/apolar branched hydrocarbon-based oil weight ratio preferably ranging from 1/99 to 10/90.

Preferably, the composition comprises one or more oils.

The term "oil" means a hydrophobic (i.e. water-immiscible) fatty (i.e. non-aqueous) substance that is liquid at room temperature (25° C.) and at atmospheric pressure (1 atm or 760 mmHg).

The term "liquid fatty substances" notably means liquid fatty substance(s) preferably having a viscosity of less than or equal to 7000 centipoises at 20° C.

The liquid fatty substance(s) of the invention more particularly have a viscosity of less than or equal to 2 Pa·s, more particularly less than or equal to 1 Pa·s, even more particularly less than or equal to 0.1 Pa·s, and more preferentially less than or equal to 0.09 Pa·s at a temperature of 25° C. and at a shear rate of 1 $s^{-1}$.

According to a particular embodiment of the invention, the liquid fatty substance(s) have a viscosity of between 0.001 Pa·s and 2 Pa·s, more particularly inclusively between 0.01 and 1 Pa·s and even more particularly inclusively between 0.014 and 0.1 Pa·s, more preferentially inclusively between 0.015 and 0.09 Pa·s at a temperature of 25° C. and at a shear rate of 1 $s^{-1}$.

The PHA copolymer(s) according to the invention are soluble in the liquid fatty substances at 25° C. and at atmospheric pressure.

According to the invention, the medium is said to be carbon-based if it comprises at least 50% by weight, notably from 50% to 100% by weight, for example from 60% to 99% by weight, or else from 65% to 95% by weight, or even from 70% to 90% by weight, relative to the total weight of the carbon-based medium, of carbon-based compound, which is liquid at 25° C.

Preferably, the liquid fatty substance(s) have an overall solubility parameter according to the Hansen solubility space of less than or equal to 20 $(MPa)^{1/2}$, or a mixture of such compounds.

The global solubility parameter δ according to the Hansen solubility space is defined in the article "Solubility parameter values" by Grulke in the book "Polymer Handbook", 3rd Edition, Chapter VII, pages 519-559, by the relationship $\delta=(dD_2+dP_2+dH_2)^{1/2}$ in which:

- $d_D$ characterizes the London dispersion forces derived from the formation of dipoles induced during molecular impacts,
- $d_p$ characterizes the Debye interaction forces between permanent dipoles,
- $d_H$ characterizes the forces of specific interactions (such as hydrogen bonding, acid/base, donor/acceptor, etc.).

The definition of solvents in the Hansen three-dimensional solubility space is described in the article by Hansen: "The three-dimensional solubility parameters", *J. Paint Technol.* 39, 105 (1967).

Among the liquid carbon-based compounds having an overall solubility parameter according to the Hansen solubility space of less than or equal to 20 $(MPa)^{112}$, mention may be made of liquid fatty substances, notably oils, which may be chosen from natural or synthetic, carbon-based, or hydrocarbon-based oils, which are optionally fluorinated, and optionally branched, alone or as a mixture.

The liquid fatty substances are notably chosen from $C_6$-$C_{16}$ hydrocarbons or hydrocarbons comprising more than 16 carbon atoms and up to 60 carbon atoms and in particular alkanes, oils of animal origin, oils of plant origin, glycerides or fluoro oils of synthetic origin, fatty alcohols, fatty acid and/or fatty alcohol esters, non-silicone waxes, and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they are linear or branched, and possibly cyclic. Examples that may be mentioned include hexane, dodecane and isoparaffins such as isohexadecane and isodecane. The linear or branched hydrocarbons containing more than 16 carbon atoms may be chosen from liquid paraffins, petroleum jelly, liquid petroleum jelly, polydecenes, and hydrogenated polyisobutene.

According to a particular embodiment, the fatty substance(s) used in the process of the invention are chosen from volatile linear alkanes.

The term "one or more volatile linear alkanes" means, without distinction, "one or more volatile linear alkane oils".

A volatile linear alkane that is suitable for use in the invention is liquid at room temperature (about 25° C.) and atmospheric pressure (101 325 Pa or 760 mmHg).

The term "volatile linear alkane" that is suitable for use in the invention means a linear alkane that can evaporate on contact with the skin in less than one hour, at room temperature (25° C.) and atmospheric pressure (101 325 Pa), which is liquid at room temperature, notably having an evaporation rate ranging from 0.01 to 15 $mg/cm^2$/minute, at room temperature (25° C.) and atmospheric pressure (101 325 Pa).

Preferably, the volatile linear alkanes that are suitable for use in the invention have an evaporation rate ranging from 0.01 to 3.5 $mg/cm^2$/minute and better still from 0.01 to 1.5 $mg/cm^2$/minute, at room temperature (25° C.) and atmospheric pressure (101 325 Pa).

More preferably, the volatile linear alkanes that are suitable for use in the invention have an evaporation rate ranging from 0.01 to 0.8 $mg/cm^2$/minute, preferentially from 0.01 to 0.3 $mg/cm^2$/minute and even more preferentially from 0.01 to 0.12 $mg/cm^2$/minute, at room temperature (25° C.) and atmospheric pressure (101 325 Pa).

The evaporation rate of a volatile alkane in accordance with the invention (and more generally of a volatile solvent) may notably be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 $m^3$ with regulated temperature (25° C.) and hygrometry (50% relative humidity).

The volatile hydrocarbon-based solvent is allowed to evaporate freely, without stirring it, while providing ventilation by means of a fan (Papst-Motoren, reference 8550 N, rotating at 2700 rpm) placed in a vertical position above the crystallizing dish containing the volatile hydrocarbon-based solvent, the blades being directed towards the crystallizing dish, 20 cm away from the bottom of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in $mg/cm^2$) as a function of the time (in min).

The evaporation rate is then calculated, which corresponds to the tangent to the origin of the curve obtained. The evaporation rates are expressed in mg of volatile solvent evaporated per unit area ($cm^2$) and per unit time (minutes).

According to a preferred embodiment, the volatile linear alkanes that are suitable for use in the invention have a non-zero vapour pressure (also known as the saturation vapour pressure), at room temperature, in particular a vapour pressure ranging from 0.3 Pa to 6000 Pa.

Preferably, the volatile linear alkanes that are suitable for use in the invention have a vapour pressure ranging from 0.3 to 2000 Pa and better still from 0.3 to 1000 Pa, at room temperature (25° C.).

More preferably, the volatile linear alkanes that are suitable for use in the invention have a vapour pressure ranging from 0.4 to 600 Pa, preferentially from 1 to 200 Pa and even more preferentially from 3 to 60 Pa, at room temperature (25° C.).

According to one embodiment, a volatile linear alkane that is suitable for use in the invention may have a flash point that is within the range from 30 to 120° C. and more particularly from 40 to 100° C. The flash point is in particular measured according to the standard ISO 3679.

According to one embodiment, the volatile linear alkanes that are suitable for use in the invention may be linear alkanes including from 7 to 15 carbon atoms, preferably from 8 to 14 carbon atoms and better still from 9 to 14 carbon atoms.

More preferably, the volatile linear alkanes that are suitable for use in the invention may be linear alkanes including from 10 to 14 carbon atoms and even more preferentially from 11 to 14 carbon atoms.

A volatile linear alkane that is suitable for use in the invention may advantageously be of plant origin.

According to a particular embodiment of the invention, the fatty medium of the composition is oily. More particularly, the composition comprises one or more oils, preferably non-silicone oils, notably hydrocarbon-based oils.

The term "hydrocarbon-based oil" means an oil consisting of carbon and hydrogen atoms.

Preferably, the liquid fatty substances of the invention are chosen from hydrocarbons, fatty alcohols, fatty esters, silicones and fatty ethers, or mixtures thereof.

More particularly, the fatty substances of the invention are not (poly)oxyalkylenated.

The term "liquid hydrocarbon" means a hydrocarbon composed solely of carbon and hydrogen atoms, which is liquid at ordinary temperature (25° C.) and at atmospheric pressure (760 mmHg; i.e. $1.013\times10^5$ Pa).

More particularly, the liquid hydrocarbons are chosen from:

- linear or branched, optionally cyclic, $C_6$-$C_{16}$ alkanes. Examples that may be mentioned include hexane, undecane, dodecane, tridecane, and isoparaffins, for instance isohexadecane, isododecane and isodecane;
- linear or branched hydrocarbons of mineral, animal or synthetic origin, containing more than 16 carbon atoms, such as liquid paraffins, liquid petroleum jelly, polydecenes hydrogenated polyisobutene such as Parleam®, and squalane.

In a preferred variant, the liquid hydrocarbon(s) are chosen from liquid paraffins and liquid petroleum jelly.

The term "liquid fatty alcohol" means a non-glycerolated and non-oxyalkylenated fatty alcohol that is liquid at ordinary temperature (25° C.) and at atmospheric pressure (760 mmHg; i.e. $1.013\times10^5$ Pa).

Preferably, the liquid fatty alcohols of the invention include from 8 to 30 carbon atoms, more preferentially $C_{10}$-$C_{22}$, even more preferentially $C_{14}$-$C_{20}$, better still $C_{16}$-$C_{18}$.

The liquid fatty alcohols of the invention may be saturated or unsaturated.

The saturated liquid fatty alcohols are preferably branched. They may optionally comprise in their structure at least one aromatic or non-aromatic ring.

Preferably, they are acyclic.

More particularly, the saturated liquid fatty alcohols of the invention are chosen from octyldodecanol, isostearyl alcohol and 2-hexyldecanol.

According to another variant of the invention, the fatty substance(s) are chosen from liquid unsaturated fatty alcohols. These liquid unsaturated fatty alcohols contain in their structure at least one double or triple bond. Preferably, the fatty alcohols of the invention bear in their structure one or more double bonds. When several double bonds are present, there are preferably two or three of them, and they may be conjugated or non-conjugated.

These unsaturated fatty alcohols may be linear or branched.

They may optionally comprise in their structure at least one aromatic or non-aromatic ring. Preferably, they are acyclic.

More particularly, the liquid unsaturated fatty alcohols of the invention are chosen from oleyl alcohol, linolyl alcohol, linolenyl alcohol and undecylenyl alcohol.

Oleyl alcohol is most particularly preferred.

The term "liquid fatty ester" or "ester oil" means a compound comprising one or more ester groups derived from a fatty acid and/or from a fatty alcohol and that is liquid at ordinary temperature (25° C.) and at atmospheric pressure (760 mmHg; i.e. $1.013\times10^5$ Pa).

The esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms in the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate, isostearyl neopentanoate, and $C_{10}$-$C_{22}$ and preferably $C_{12}$-$C_{20}$ alkyl (iso)stearates such as isopropyl isostearate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may notably be made of diethyl sebacate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which include at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be notably chosen from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates and arachidonates, or mixtures thereof such as, notably, oleopalmitate, oleostearate and palmitostearate mixed esters.

More particularly, use is made of monoesters and diesters and notably sucrose, glucose or methylglucose monooleate or dioleate, stearate, behenate, oleopalmitate, linoleate, linolenate or oleostearate.

An example that may be mentioned is the product sold under the name Glucate® DO by the company Amerchol, which is a methylglucose dioleate.

Finally, use may also be made of natural or synthetic glycerol esters of mono-, di- or triacids.

Among these, mention may be made of plant oils.

As oils of plant origin or synthetic triglycerides that may be used in the composition of the invention as liquid fatty esters, examples that may be mentioned include:

triglyceride oils of plant or synthetic origin, such as liquid fatty acid triglycerides including from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, caprylic/capric acid triglycerides, for instance those sold by the company Stéarinerie Dubois or those sold under the names Miglyol® 810, 812 and 818 by the company Dynamit Nobel, jojoba oil and shea butter oil.

Use will preferably be made, as esters according to the invention, of liquid fatty esters derived from monoalcohols.

Isopropyl myristate or isopropyl palmitate is preferred.

The liquid fatty ethers are chosen from liquid dialkyl ethers such as dicaprylyl ether.

According to a preferred embodiment of the invention, the composition comprises one or more hydrocarbon-based oils containing from 8 to 16 carbon atoms.

More particularly, the hydrocarbon-based oil(s) containing from 8 to 16 carbon atoms are chosen from:

- branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane, isohexadecane and, for example, the oils sold under the Isopar or Permethyl trade names,
- linear $C_8$-$C_{16}$ alkanes, for instance n-dodecane ($C_{12}$) and n-tetradecane ($C_{14}$) sold by Sasol under the references, respectively, Parafol 12-97 and Parafol 14-97, and also mixtures thereof, the undecane-tridecane mixture, mixtures of n-undecane ($C_{11}$) and of n-tridecane ($C_{13}$) obtained in Examples 1 and 2 of patent application WO 2008/155059 from the company Cognis, and mixtures thereof.

The term "ester oil" means an oily compound containing one or more ester groups in its chemical structure.

The ester oil(s) are particularly chosen from:

- oils of plant origin, such as triglycerides consisting of fatty acid esters of glycerol in which the fatty acids may have varied chain lengths from $C_4$ to $C_{24}$, these chains possibly being linear or branched, and saturated or unsaturated; these oils are notably heptanoic acid or octanoic acid triglycerides. The oils of plant origin may be chosen from wheatgerm oil, sunflower oil, grapeseed oil, sesame seed oil, groundnut oil, corn oil, apricot oil, castor oil, shea oil, avocado oil, olive oil, soybean oil, sweet almond oil, palm oil, rapeseed oil, cottonseed oil, coconut oil, hazelnut oil, walnut oil, rice oil, linseed oil, macadamia oil, alfalfa oil, poppy oil, pumpkin oil, sesame seed oil, marrow oil, rapeseed oil, blackcurrant oil, evening primrose oil, millet oil, barley oil, quinoa oil, rye oil, safflower oil, candlenut oil, passion flower oil, musk rose oil and argan oil; shea butter; or alternatively caprylic/capric acid triglycerides such as those sold by the company Stéarinerie Dubois or those sold under the names Miglyol 810®, 812® and 818® by the company Dynamit Nobel;
- monoester oils of formula $R^9$—C(O)—$OR^{10}$ in which $R^9$ represents a linear or branched hydrocarbon-based chain including from 5 to 19 carbon atoms and $R^{10}$ represents a linear or branched, notably branched, hydrocarbon-based chain containing from 4 to 20 carbon atoms, on condition that $R^9+R^{10}\geq 9$ carbon atoms and preferably less than 29 carbon atoms, for instance palmitates, adipates, myristates and benzoates, notably diisopropyl adipate and isopropyl myristate; cetearyl octanoate (purcellin oil), isopropyl myristate, isopropyl palmitate, hexyl laurate, isononyl isononanoate, 2-ethylhexyl palmitate, isostearyl isostearate, 2-hexyldecyl laurate, 2-octyldecyl palmitate, 2-octyldodecyl myristate, 2-ethylhexyl hexanoate, isononyl hexanoate, neopentyl hexanoate, caprylyl heptanoate or octyl octanoate;
- esters of lactic acid and of $C_{10}$-$C_{20}$ alcohol, such as isostearyl lactate, 2-octyldodecyl lactate, myristyl lactate, $C_{12}$-$C_{13}$ alkyl lactate (Cosmacol® ELI from Sasol), cetyl lactate or lauryl lactate;
- diesters of malic acid and of $C_{10}$-$C_{20}$ alcohol, such as diisostearyl malate, di($C_{12}$-$C_{13}$)alkyl malate (Cosmacol® EMI from Sasol), dibutyloctyl malate, diethylhexyl malate or dioctyldodecyl malate;
- esters of pentaerythritol and of $C_8$-$C_{22}$ carboxylic acid (in particular tetraesters or diesters), such as pentaerythrityl tetraoctanoate, pentaerythrityl tetraisostearate, pentaerythrityl tetrabehenate, pentaerythrityl tetracaprylate/tetracaprate, pentaerythrityl tetracocoate, pentaerythrityl tetraethylhexanoate, pentaerythrityl tetraisononanoate, pentaerythrityl tetrastearate, pentaerythrityl tetraisostearate, pentaerythrityl tetralaurate, pentaerythrityl tetramyristate, pentaerythrityl tetraoleate or pentaerythrityl distearate;
- diesters of the following formula (VII) $R^{11}$—O—C(O)—$R^{12}$—C(O)—O—$R^{13}$, with $R^{11}$ and $R^{13}$, which may be identical or different, representing a linear or branched, saturated or unsaturated (preferably saturated) $C_4$ to $C_{12}$ and preferentially $C_5$ to $C_{10}$ alkyl chain, optionally containing at least one saturated or unsaturated, preferably saturated, ring, and $R^{12}$ representing a saturated or unsaturated $C_1$ to $C_4$, preferably $C_2$ to $C_4$, alkylene chain, for instance an alkylene chain derived from succinate (in this case $R^{12}$ is a saturated $C_2$ alkylene chain), maleate (in this case $R^{12}$ is an unsaturated $C_2$ alkylene chain), glutarate (in this case $R^{12}$ is a saturated $C_3$ alkylene chain) or adipate (in this case $R^{12}$ is a saturated $C_4$ alkylene chain); in particular, $R^{11}$ and $R^{13}$ are chosen from isobutyl, pentyl, neopentyl, hexyl, heptyl, neoheptyl, 2-ethylhexyl, octyl, nonyl and isononyl; mention may be made preferentially of dicaprylyl maleate or bis(2-ethylhexyl) succinate;
- diesters of the following formula (VIII) $R^{14}$—C(O)—O—$R^{15}$—O—C(O)—$R^{16}$, with $R^{14}$ and $R^{16}$, which may be identical or different, representing a linear or branched, saturated or unsaturated (preferably saturated) $C_4$ to $C_{12}$ and preferentially $C_5$ to $C_{10}$ alkyl chain and $R^{15}$ representing a saturated or unsaturated $C_1$ to $C_4$ and preferably $C_2$ to $C_4$ alkylene chain. Mention may notably be made of 1,3-propanediol dicaprylate ($R^{14}$ as $C_7$ and $R^{16}$ as $C_3$), sold under the name Dub Zenoat by the company Stéarinierie Dubois, or dipropylene glycol dicaprylate;
- the carbonate oils may be chosen from the carbonates of formula $R^{17}$—O—C(O)—O—$R^{18}$, with $R^{17}$ and $R^{18}$, which may be identical or different, representing a linear or branched $C_4$ to $C_{12}$ and preferentially $C_6$ to $C_{10}$ alkyl chain; the carbonate oils may be dicaprylyl carbonate (or dioctyl carbonate), sold under the name Cetiol CC® by the company BASF, bis(2-ethylhexyl) carbonate, sold under the name Tegosoft DEC® by the company Evonik, dipropylheptyl carbonate (Cetiol 4 All from BASF), dibutyl carbonate, dineopentyl carbonate, dipentyl carbonate, dineoheptyl carbonate, diheptyl carbonate, diisononyl carbonate or dinonyl carbonate and preferably dioctyl carbonate.

In particular, the fatty substance(s) b) are chosen from:

plant oils formed by fatty acid esters of polyols, in particular triglycerides, such as sunflower oil, sesame oil, rapeseed oil, macadamia oil, soybean oil, sweet almond oil, beauty-leaf oil, palm oil, grapeseed oil, corn oil, arara oil, cottonseed oil, apricot oil, avocado oil, jojoba oil, olive oil or cereal germ oil;

linear, branched or cyclic esters containing more than 6 carbon atoms, notably 6 to 30 carbon atoms; and notably isononyl isononanoate; and more particularly esters of formula R—C(O)—O—R' in which R represents a higher fatty acid residue including from 7 to 19 carbon atoms and R' represents a hydrocarbon-based chain including from 3 to 20 carbon atoms, such as palmitates, adipates, myristates and benzoates, notably diisopropyl adipate and isopropyl myristate;

hydrocarbons and notably volatile or non-volatile, linear, branched and/or cyclic alkanes, such as $C_5$-$C_{60}$ isoparaffins, which are optionally volatile, such as isododecane, Parleam (hydrogenated polyisobutene), isohexadecane, cyclohexane or Isopars; or else liquid paraffins, liquid petroleum jelly, or hydrogenated polyisobutylene;

ethers containing 6 to 30 carbon atoms;

ketones containing 6 to 30 carbon atoms;

aliphatic fatty monoalcohols containing 6 to 30 carbon atoms, the hydrocarbon-based chain not including any substitution groups, such as oleyl alcohol, decanol, dodecanol, octadecanol, octyldodecanol and linoleyl alcohol;

polyols containing 6 to 30 carbon atoms, such as hexylene glycol; and mixtures thereof.

Preferably, the composition comprises, in the fatty medium, at least one oil chosen from:

plant oils formed by fatty acid esters of polyols, in particular triglycerides, esters of formula RC(O)—OR' in which R represents a higher fatty acid residue including from 7 to 19 carbon atoms and R' represents a hydrocarbon-based chain including from 3 to 20 carbon atoms, volatile or non-volatile, linear or branched $C_8$-$C_{30}$ alkanes, volatile or non-volatile, non-aromatic cyclic $C_5$-$C_{12}$ alkanes, ethers containing 7 to 30 carbon atoms, ketones containing 8 to 30 carbon atoms, aliphatic fatty monoalcohols containing 12 to 30 carbon atoms, the hydrocarbon-based chain not including any substitution groups, and mixtures thereof.

Preferably, when the copolymer is such that the alkyl group $R^1$ comprises from 6 to 9 carbon atoms, the fatty substance(s) b) are chosen from apolar hydrocarbon-based oils containing from 8 to 14 carbon atoms in the absence of monoalcohol containing from 2 to 6 carbon atoms.

Preferably, when the copolymer is such that the alkyl group $R^1$ comprises 9 carbon atoms, the fatty substance(s) b) are chosen from hydrogenated polyisobutylenes.

In particular, the fatty substance(s) are chosen from non-silicone oils; preferably, the liquid fatty substance(s) are chosen from:

ester oils, carbonate oils; and branched apolar hydrocarbon-based oils containing from 8 to 14 carbon atoms; as a mixture with a monoalcohol containing from 2 to 6 carbon atoms preferably in a monoalcohol/branched apolar hydrocarbon-based oil weight ratio ranging from 1/99 to 10/90.

Advantageously, the composition comprises one or more fatty substances, which are notably liquid at 25° C. and at atmospheric pressure, preferably one or more oils, of the fatty medium in a content ranging from 2% to 99.9% by weight, relative to the total weight of the composition, preferably ranging from 5% to 90% by weight, preferably ranging from 10% to 80% by weight, preferably ranging from 20% to 80% by weight.

According to one embodiment of the invention, the composition comprises an aqueous phase. The composition is notably formulated as aqueous lotions or as water-in-oil or oil-in-water emulsions or as multiple emulsions (oil-in-water-in-oil or water-in-oil-in-water triple emulsion (such emulsions are known and described, for example, by C. Fox in "*Cosmetics and Toiletries*"—November 1986—Vol. 101—pages 101-112)).

According to a particular embodiment of the invention, the composition is a direct emulsion, i.e. an emulsion of oil-in-water or O/W type. The weight amount of oil is preferably less than or equal to 30% in the inverse emulsion, preferably less than 20% by weight relative to the total weight of the composition. More particularly, in the direct emulsion, the amount of water is greater than or equal to 40% by weight relative to the total weight of the composition.

According to another particular embodiment of the invention, the composition of the invention is an inverse emulsion, i.e. of water-in-oil or W/O type. The weight amount of oil is preferably greater than 30% in the inverse emulsion, preferably greater than 40% by weight relative to the total weight of the composition. More particularly, in the inverse emulsion, the amount of water is less than 40% by weight relative to the total weight of the composition, preferably less than or equal to 30% by weight, more preferably less than 20% by weight.

The aqueous phase of the composition contains water and in general other water-soluble or water-miscible solvents such as polar and protic solvents as defined below (see additional solvents).

The composition according to the invention preferably has a pH ranging from 3 to 9, depending on the support chosen.

According to a particular embodiment of the invention, the pH of the composition(s) is neutral or even slightly acidic. Preferably, the pH of the composition is between 6 and 7. The pH of these compositions may be adjusted to the desired value by means of acidifying or basifying agents usually used in cosmetics, or alternatively using standard buffer systems.

The term "basifying agent" or "base" means any agent for increasing the pH of the composition in which it is present. The basifying agent is a Brønsted, Lowry or Lewis base. It may be mineral or organic. Particularly, said agent is chosen from a) aqueous ammonia, b) (bi)carbonate, c) alkanolamines such as monoethanolamine, diethanolamine, triethanolamine and derivatives thereof, d) oxyethylenated and/or oxypropylenated ethylenediamines, e) organic amines, f) mineral or organic hydroxides, g) alkali metal silicates such as sodium metasilicates, h) amino acids, preferably basic amino acids such as arginine, lysine, ornithine, citrulline and histidine, and i) the compounds of formula (F) below:

[Chem. 26]

(F)

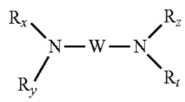

in which formula (F):

W is a divalent $C_1$-$C_6$ alkylene radical optionally substituted with one or more hydroxyl groups or a $C_1$-$C_6$ alkyl radical, and/or optionally interrupted with one or more heteroatoms such as O or $NR_u$;

$R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (E) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Among the mineral or organic hydroxides, mention may be made of those chosen from a) hydroxides of an alkali metal, b) hydroxides of an alkaline-earth metal, for instance sodium hydroxide or potassium hydroxide, c) hydroxides of a transition metal, d) hydroxides of lanthanides or actinides, quaternary ammonium hydroxides and guanidinium hydroxide. The mineral or organic hydroxides a) and b) are preferred.

Among the acidifying agents for the compositions used in the invention, examples that may be mentioned include mineral or organic acids, for instance hydrochloric acid, orthophosphoric acid, sulfuric acid, carboxylic acids, for instance acetic acid, tartaric acid, citric acid or lactic acid, or sulfonic acids.

The basifying agents and the acidifying agents as defined previously preferably represent from 0.001% to 20% by weight relative to the weight of the composition containing them and more particularly from 0.005% to 8% by weight of the composition.

According to a preferred embodiment of the invention, the composition comprises an amount of water of less than or equal to 10% by weight relative to the total weight of the composition. Even more preferentially, the composition comprises an amount of water of less than or equal to 5%, better still less than 2%, even better still less than 0.5%, and is notably free of water. Where appropriate, such small amounts of water may notably be introduced by ingredients of the composition that may contain residual amounts thereof.

Even more preferentially, the composition does not comprise any water.

Advantageously, the composition according to the invention comprises a physiologically acceptable medium. In particular, the composition is a cosmetic composition.

The term "physiologically acceptable medium" means a medium that is compatible with human keratin materials, for instance the skin, the lips, the nails, the eyelashes, the eyebrows or the hair.

The term "cosmetic composition" means a composition that is compatible with keratin materials, which has a pleasant colour, odour and feel and which does not cause any unacceptable discomfort (stinging, tautness or redness) liable to discourage the consumer from using it.

The term "keratin materials" means the skin (body, face, contour of the eyes, scalp), head hair, the eyelashes, the eyebrows, bodily hair, the nails or the lips.

The composition according to the invention may comprise a cosmetic additive chosen from water, fragrances, preserving agents, fillers, colouring agents, UV-screening agents, oils, waxes, surfactants, moisturizers, vitamins, ceramides, antioxidants, free-radical scavengers, polymers and thickeners. In particular, the composition according to the invention also comprises one or more colouring agents chosen from pigments, direct dyes and mixtures thereof, preferably pigments; more preferentially, the pigment(s) of the invention are chosen from carbon black, iron oxides, notably black iron oxides, and micas coated with iron oxide, triarylmethane pigments, notably blue and violet triarylmethane pigments, such as Blue 1 Lake, azo pigments, notably red azo pigments, such as D&C Red 7, an alkali metal salt of lithol red, such as the calcium salt of lithol red B, even more preferentially red iron oxides.

Advantageously, the composition according to the invention is a makeup composition, in particular a lip makeup composition, a mascara, an eyeliner, an eyeshadow or a foundation.

Additional Solvents

According to a particular embodiment of the invention, the composition comprises one or more solvents, which are preferably polar and/or protic, other than water in the predominantly fatty medium.

The solvent(s), which are preferably polar and/or protic, other than water are present in the composition in a weight percentage of between 0 and 10% relative to the total weight of the solvent mixture, preferentially between 0.5% and 8%, more particularly between 1% and 5%, such as 2% by weight, relative to the total weight of the composition. Preferably, the solvent(s) are polar protic solvents such as alkanols, more preferentially $C_2$-$C_6$ alkanols, such as ethanol.

The Adjuvants

The composition according to the invention may also comprise one or more fillers, notably in a content ranging from 0.01% to 30% by weight and preferably ranging from 0.01% to 20% by weight relative to the total weight of the composition. The term "fillers" should be understood as meaning colourless or white, mineral or synthetic particles of any shape, which are insoluble in the medium of the composition, irrespective of the temperature at which the composition is manufactured. These fillers notably serve to modify the rheology or texture of the composition.

The composition according to the invention may also contain ingredients commonly used in cosmetics, such as vitamins, thickeners, trace elements, softeners, sequestrants, fragrances, preserving agents, sunscreens, antioxidants, agents for combating loss, antidandruff agents and propellants, or mixtures thereof.

The composition according to the invention may be in the form of an anhydrous composition, a water-in-oil emulsion or an oil-in-water emulsion.

The term "anhydrous composition" means a composition containing less than 2% by weight of water, or even less than 0.5% of water, and is notably free of water. Where appropriate, such small amounts of water may notably be introduced by ingredients of the composition that may contain residual amounts thereof.

The invention is illustrated in greater detail in the examples that follow. The amounts are indicated as weight percentages.

EXAMPLES

The PHAs illustrated in the various examples were prepared in 3-litre chemostats and/or 5-litre Fernbach flasks depending on whether or not a β-oxidation pathway inhibitor is used. The isolation of the PHAs is similar for all the examples obtained.

In a first step, the microorganism generates the PHAs which are stored in intracellular granules, the proportion of which varies as a function of the applied conditions such as the temperature or the nature of the culture medium. The generation of PHA granules may or may not be associated with the growth of the microorganism as a function of the nature of the microorganisms. During the second step, the biomass containing the PHAs is isolated, i.e. separated from the fermentation medium, and then dried. The PHAs are extracted from the biomass before being purified, if necessary.

A mixture of saturated and unsaturated carbon sources is, for certain examples, necessary for the stability of the PHA obtained.

TABLE 5

| Carbon source | CAS |
|---|---|
| Caprylic acid (RADIACID 608) | 124-07-2 |
| Nonanoic acid | 112-05-0 |
| Undecylenic acid (10-Undecenoic acid) | 112-38-9 |

TABLE 6

| Carbon source | Genus and species | Source |
|---|---|---|
| Caprylic and undecylenoic acid mixture | *Pseudomonas putida* | ATCC ® 47054 ™ |
| Nonanoic and undecylenoic acid mixture | *Pseudomonas putida* | ATCC ® 47054 ™ |

Example 1: PHA Bearing a Side Chain $R^1$ Representing a Linear 10% Unsaturated n-Octenyl Group and $R^2$ Representing an n-Pentyl Group

[Chem. 27]

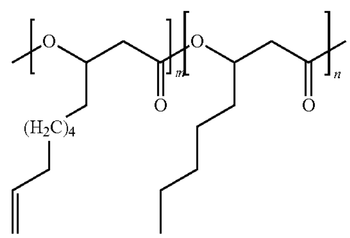

The process for synthesizing the compound of Example 1 is adapted from the article: *Fed-batch production of unsaturated medium-chain-length polyhydroxyalkanoates with controlled composition by Pseudomonas putida* KT2440, Z. Sun, J. A. Ramsay, M. Guay, B. A. Ramsay, Applied Microbiology Biotechnology, 82, 657-662, 2009.

The microorganism used is *Pseudomonas putida* KT2440 ATCC® 47054™. The culture method is performed under fed-batch growth axenic conditions with a maintenance solution containing a mixture of carbon source at a rate $\mu=0.15\ h^{-1}$ in a 3 L chemostat containing 2.5 L of culture medium.

The system is aerated with a flow of 0.5 vvm of air for a nominal dissolved oxygen ($O_D$) value at 30% of saturation. The pH is regulated with 15% aqueous ammonia solution. The temperature of the fermentation medium is regulated at 30° C.

Assembly for the Fed-Batch Growth Fermentation Mode

The fermentation medium is regulated in terms of temperature-pressure of dissolved oxygen and pH (not shown) See FIG. 1

The production process is performed using three different culture media. The first culture medium, defined CM1 "inoculum", is used for the preparation of the preculture. The second culture medium, defined CM2 "batch", is used for unfed batch growth of the microorganism with the primary carbon sources in the Fernbach flasks. The third culture medium, defined CM3 "maintenance", is used for the fed-batch or maintenance fermentation mode with the carbon sources of interest at a flow rate calibrated as a function of the growth of the microorganism.

TABLE 7

| Ingredients in grams per litre | CM1 <<inoculum>> | CM2 <<batch>> | CM3 <<maintenance>> |
|---|---|---|---|
| $(NH_4)_2SO_4$ | 4.7 | 4.7 | |
| $Na_2HPO_4$•$7H_2O$ | 12 | 9 | |
| $KH_2PO_4$ | 2.7 | 2.03 | |
| $MgSO_4$•$7H_2O$ | 0.8 | 1.03 | |
| Nutrient Broth | 3 | / | |
| Caprylic acid | / | 0.9 | 900 |
| Undecylenic acid | / | 0.1 | 100 |
| Microelement solution | / | 10 | |
| Acrylic acid | / | / | |
| 2N NaOH | | QSP pH = 6.8 | |
| MilliQ water | | QSP 1000 g | |

The composition of the Nutrient Broth, as mass percentages, is 37.5% beef extract and 62.5% peptone. Reference 233000 DIFCO™.

TABLE 8

| Ingredients in grams per litre | Amount |
|---|---|
| $FeSO_4$•$7H_2O$ | 10.0 g |
| $CaCl_2$•$2H_2O$ | 3.0 g |
| $ZnSO_4$•$7H_2O$ | 2.2 g |
| $MnSO_4$•$4H_2O$ | 0.5 g |
| $H_3BO_3$ | 0.3 g |
| $CoCl_2$•$6H_2O$ | 0.2 g |
| $Na_2MoO_4$•$2H_2O$ | 0.15 g |
| $NiCl_2$•$6H_2O$ | 0.02 g |
| $CuSO_4$•$5H_2O$ | 1.00 g |
| MilliQ water (or 0.5N HCL) | QSP 1000 g |

100 mL of preculture are prepared by suspending a cryotube containing 1 mL of the strain with 100 mL of "inoculum" culture medium at a pH adjusted to 6.8 with 2N NaOH in a 250 mL Fernbach flask and are then incubated at 30° C. at 150 rpm for 24 hours. 1.9 L of CM2 "batch" culture medium placed in a presterilized 3 L chemostat are inoculated at OD=0.1 with the 100 mL of preculture, after 4 hours at 30° C. at 850 rpm.

At the end of the introduction, the biomass is isolated by centrifugation and then washed three times with water. The biomass is dried by lyophilization before being extracted with ethyl acetate for 24 hours. The suspension is clarified by filtration on a GF/A filter (Whatman®). The filtrate, the PHA compound dissolved in the ethyl acetate, is concentrated by evaporation and then dried under high vacuum at 40° C. to constant mass.

The PHA may optionally be purified by successive dissolution and precipitation from an ethyl acetate/ethanol 70% methanol system, for example.

The PHA was fully characterized by spectroscopic and spectrometric methods and is in accordance with the expected chemical structure.

Example 2: Poly(3-Hydroxyoctanoate-Co-Undecenoate) Containing 10% Unsaturations 100% Grafted with Thiolactic Acid (Compound of Example 1 Grafted with Thiolactic Acid TLA)

[Chem. 28]

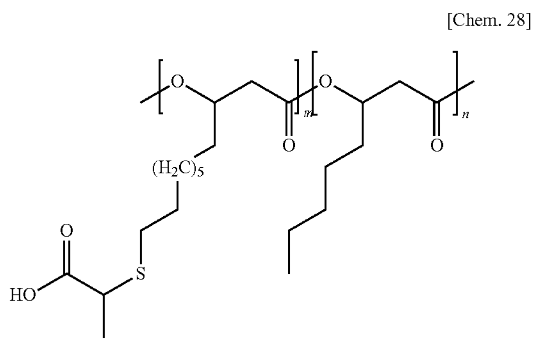

1 g of the compound of Example 1 and 150 mg of thiolactic acid were dissolved in 20 mL of ethyl acetate at room temperature with stirring. 20 mg of 2,2-dimethoxy-2-phenylacetophenone (Irgacure 651) were added to the mixture. The medium was then irradiated under a 100 W UV lamp at 365 nm (reference) and with stirring for at least 10 minutes.

20 mL of the reaction medium were then precipitated from a 200 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 2 was fully characterized by spectroscopic and spectrometric methods and is in accordance with the expected chemical structure.

Example 3: Poly(3-hydroxyoctanoate-co-undecenoate) Containing 10% Unsaturations 100% Grafted with Octanethiol (Compound of Example 1 Grafted with n-octanethiol)

[Chem. 30]

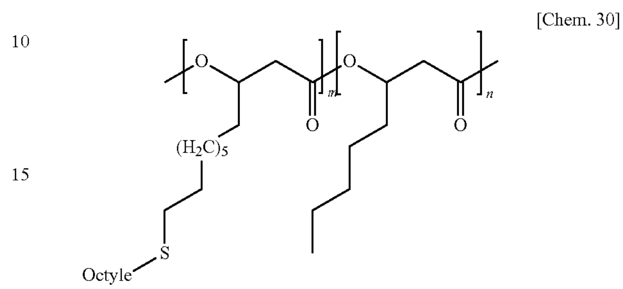

0.5 g of the compound of Example 1 and 125 mg of octanethiol were dissolved in 10 mL of ethyl acetate at room temperature with stirring. 15 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 100 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 3 was fully characterized by spectroscopic and spectrometric methods and is in accordance with the expected chemical structure.

Example 4: Poly(3-hydroxyoctanoate-co-undecenoate) Containing 10% Unsaturations 75% Grafted with 8-mercapto-1-octanol (Compound of Example 1 Grafted with 8-mercapto-1-octanol)

[Chem. 31]

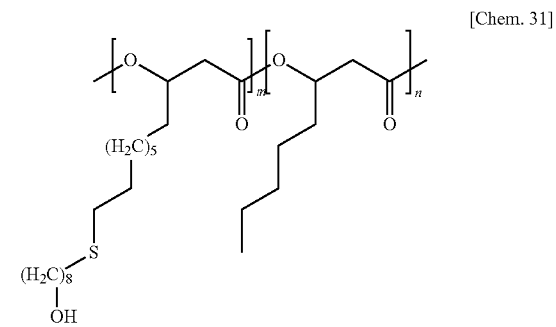

50 mg of the compound of Example 1 and 10 mg of 8-mercapto-1-octanol were dissolved in 5 mL of ethyl acetate at room temperature with stirring. 2 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 50 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 4 was fully characterized by spectroscopic and spectrometric methods and is in accordance with the expected chemical structure. Grafting to 75% or 7.5% of functions in total.

Example 5: Poly(3-hydroxyoctanoate-co-undecenoate) Containing 10% Unsaturations 32% Grafted with Cysteamine (Compound of Example 1 Grafted with Cysteamine)

[Chem. 32]

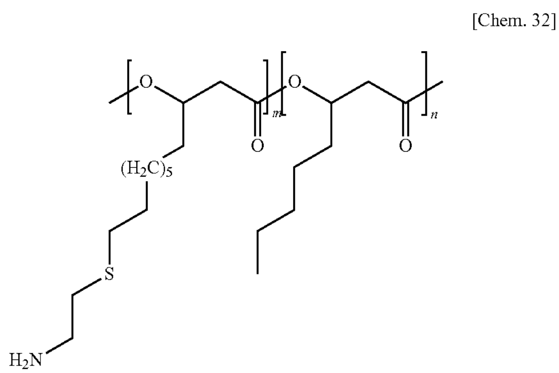

0.5 g of the compound of Example 1 and 54 mg of cysteamine were dissolved in a mixture of 10 mL of dichloromethane and 2 mL of ethanol at room temperature with stirring. 10 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 100 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 5 was fully characterized by spectroscopic and spectrometric methods and is in accordance with the expected chemical structure. Grafting to 32% (see the spectrum below) or 3.2% of functions in total.

Example 6: Poly(3-hydroxyoctanoate-co-undecenoate) Containing 10% Unsaturations 73% Grafted with Cyclohexanethiol (Compound of Example 1 Grafted with CHT)

[Chem. 33]

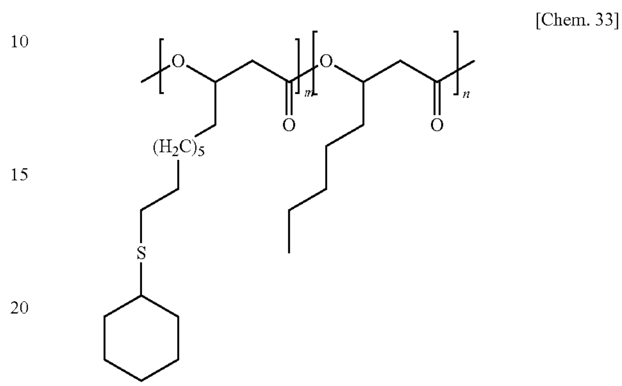

100 mg of the compound of Example 1 and 26 mg of cyclohexanethiol were dissolved in 5 mL of dichloromethane at room temperature with stirring. 5 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 50 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 6 was fully characterized by spectroscopic and spectrometric methods and is in accordance with the expected chemical structure. Grafting to 73% or 7.3% of functions in total.

Example 7: Poly(3-hydroxyoctanoate-co-undecenoate) Containing 10% Unsaturations 66% Grafted with 2-furanmethanethiol (FT) (Compound of Example 1 Grafted with FT)

[Chem. 34]

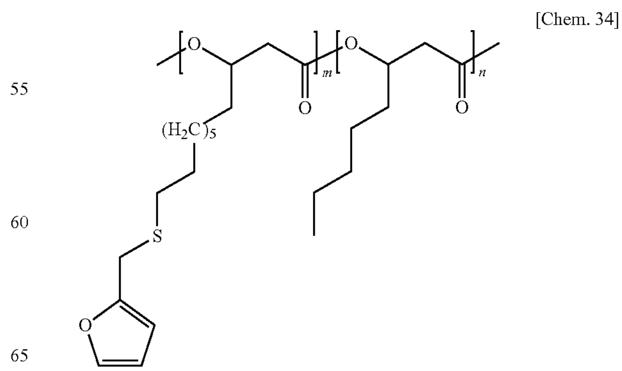

100 mg of the compound of Example 1 and 26 mg of 2-furanmethanethiol were dissolved in 5 mL of dichloromethane at room temperature with stirring. 5 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 50 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 7 was fully characterized by spectroscopic and spectrometric methods and is in accordance with the expected chemical structure. Grafting to 66% or 6.6% of functions in total.

Example 8: Poly(3-hydroxyoctanoate-co-undecenoate) Containing 10% Unsaturations 66% Grafted with 1-thio-β-D-glucose tetraacetate (Compound of Example 1 Grafted with TGT)

[Chem. 35]

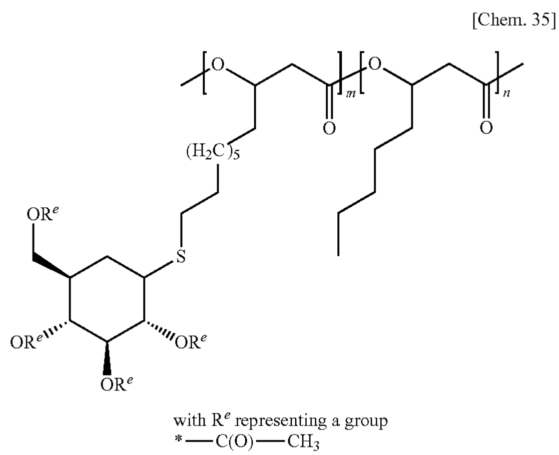

with $R^e$ representing a group $*—C(O)—CH_3$ 100 mg of the compound of Example 1 and 26 mg of 1-thio-β-D-glucose tetraacetate were dissolved in 5 mL of dichloromethane at room temperature with stirring. 5 mg of 2,2-dimethoxy-2-phenylacetophenone (Irgacure 651) were added to the mixture.

The medium was then irradiated under a 100 W UV lamp at 365 nm (reference) and with stirring for at least 10 minutes. The reaction medium was then precipitated from a 50 mL mixture of 70/30 v/v ethanol/water. A viscous white precipitate was obtained. This step may be repeated.

The product thus obtained was dissolved in a minimum amount of ethyl acetate, poured onto a Teflon plate and then dried under dynamic vacuum at 40° C. to obtain a homogeneous film.

The grafted PHA of Example 8 was fully characterized by spectroscopic and spectrometric methods and is in accordance with the expected chemical structure. Grafting to 70% or 7% of functions in total.

Example 9: Poly(3-hydroxyoctanoate-co-undecenoate) Containing 10% Unsaturations 50% Grafted with 2-phenylethanethiol (PT) (compound of Example 1 grafted with PT)

[Chem. 36]

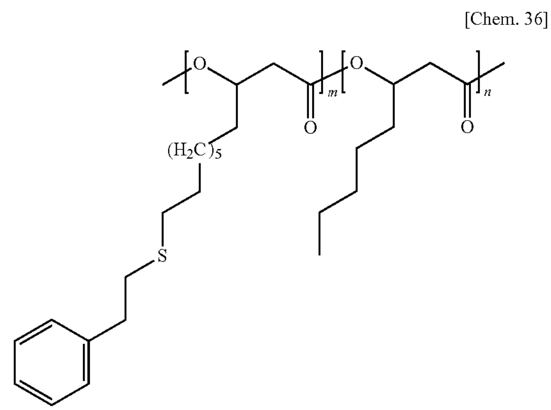

100 mg of the compound of Example 1 and 26 mg of 2-phenylethanethiol were dissolved in 5 mL of dichloromethane at room temperature with stirring. 5 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 50 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 9 was fully characterized by spectroscopic and spectrometric methods and is in accordance with the expected chemical structure. Grafting to 50% or 5% of functions in total.

Example 10: Poly(3-hydroxyoctanoate-co-undecenoate) Containing 10% Unsaturations 64% Grafted with 4-tert-butylbenzyl mercaptan (TBM) (Compound of Example 1 Grafted with TBM)

[Chem. 39]

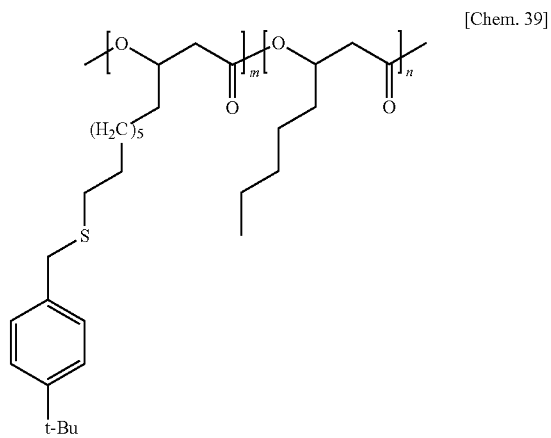

100 mg of the compound of Example 1 and 26 mg of 4-tert-butylbenzyl mercaptan were dissolved in 5 mL of dichloromethane at room temperature with stirring. 5 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 50 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 10 was fully characterized by spectroscopic and spectrometric methods and is in accordance with the expected chemical structure. Grafting to 64% or 6.4% of functions in total.

Example 11: Poly(3-hydroxynonanoate-co-undecenoate) Containing 10% Unsaturations 100% Grafted with Thiolactic Acid

[Chem. 40]

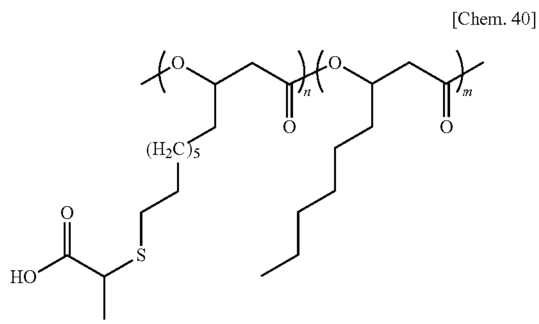

0.1 g of the compound of Example 1 and 15 mg of thiolactic acid were dissolved in 5 mL of chloroform at room temperature with stirring. 5 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 50 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 11 was fully characterized by spectroscopic and spectrometric methods and is in accordance with the expected chemical structure. Grafting to 100%.

Example 12: Poly(3-hydroxynonanoate-co-undecenoate) Containing 5% Unsaturations 100% Grafted with Octanethiol

[Chem. 41]

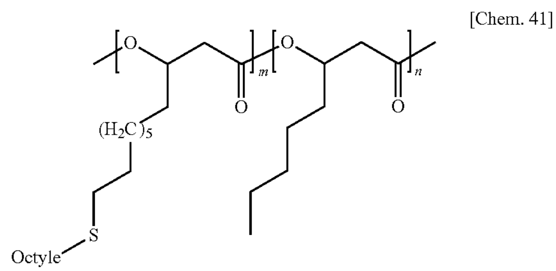

Preparation of Example 1: Copolymer of PHA Bearing a Side Chain $R^1$ Representing an n-Hexyl Group and $R^2$ Representing an n-Hexyl Group

[Chem. 42]

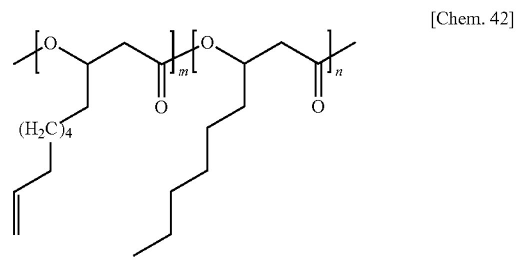

The production process of Example 1 is adapted to that of Example 1', replacing the n-octanoic acid carbon source of Example 1 with n-nonanoic acid.

The PHA copolymer of Example 1' was fully characterized by spectroscopic and spectrometric methods and is in accordance with the expected chemical structure, with a degree of unsaturation of 5%.

1 g of the PHA copolymer of Example 1' and 150 mg of octanethiol were dissolved in 15 mL of ethyl acetate at room temperature with stirring. 20 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 500 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The grafted PHA of Example 12 was fully characterized by spectroscopic and spectrometric methods and is in accordance with the expected chemical structure. Grafting to 100%.

Example 13: Poly(3-hydroxynonanoate-co-undecenoate) Containing 5% Unsaturations 100% Epoxidized

[Chem. 43]

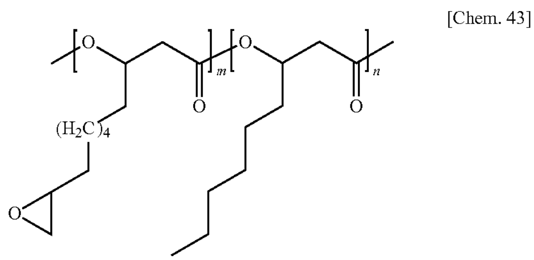

20 g of the PHA copolymer of Example 1' were dissolved in 80 mL of anhydrous dichloromethane. A suspension of 1.9 g of 77% m-CPBA was prepared with 20 mL of anhydrous dichloromethane and added to the mixture with stirring, at room temperature for at least 120 hours.

The reaction medium was then precipitated from a 500 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The PHA of Example 13 was fully characterized by spectroscopic and spectrometric methods and is in accordance with the expected chemical structure. Epoxidation to 100%.

Example 14: Poly(3-hydroxynonanoate-co-undecenoate) Containing 10% Unsaturations 100% Epoxidized 10 g of the PHA copolymer identical to that of Example 1' but with a degree of unsaturation of 10% were dissolved in 40 mL of anhydrous dichloromethane. A suspension of 1.9 g of 77% m-CPBA was prepared with 10 mL of anhydrous dichloromethane and added to the mixture with stirring, at room temperature for at least 120 hours.

The reaction medium was then precipitated from a 500 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The PHA of Example 14 was fully characterized by spectroscopic and spectrometric methods and is in accordance with the expected chemical structure. Epoxidation to 100%.

Example 15: Poly(3-hydroxynonanoate-co-undecenoate) Containing 30% Unsaturations 100% Epoxidized 10 g of the PHA copolymer identical to that of Example 1' but with a degree of unsaturation of 30% were dissolved in 40 mL of anhydrous dichloromethane. A suspension of 6.2 g of 77% m-CPBA was prepared with 10 mL of anhydrous dichloromethane and added to the mixture with stirring, at room temperature for at least 120 hours.

The reaction medium was then precipitated from a 250 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The PHA of Example 15 was fully characterized by spectroscopic and spectrometric methods and is in accordance with the expected chemical structure. Epoxidation to 100%.

Example 16: Poly(3-hydroxynonanoate-co-undecenoate) Containing 5% Unsaturations 100% Grafted with 4-tert-butylbenzyl mercaptan (TBM) (Compound of Example 1' Grafted with TBM)

[Chem. 45]

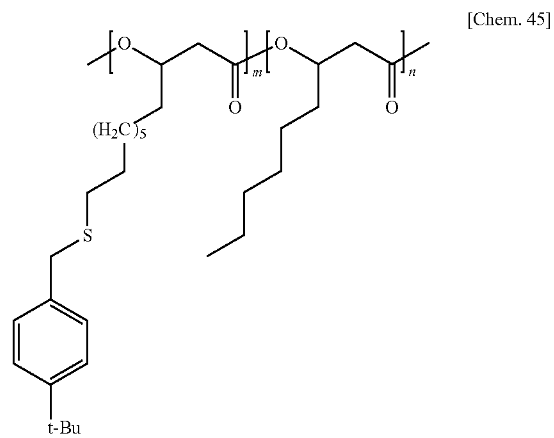

2 g of the PHA copolymer of Example 1' and 300 mg of 4-tert-butylbenzyl mercaptan were dissolved in 25 mL of ethyl acetate at room temperature with stirring. 25 mg of 2,2-dimethoxy-2-phenylacetophenone (Irgacure 651) were added to the mixture. The medium was then irradiated under a 100 W UV lamp at 365 nm (reference) and with stirring for at least 10 minutes.

The reaction medium was then precipitated from a 500 mL mixture of 70/30 v/v ethanol/water. A viscous white precipitate was obtained. This step may be repeated. The product thus obtained was dissolved in a minimum amount of ethyl acetate, poured onto a Teflon plate and then dried under dynamic vacuum at 40° C. to obtain a homogeneous film.

The PHA of Example 16 was fully characterized by spectroscopic and spectrometric methods and is in accordance with the expected chemical structure. Grafting to 100%.

Example 17: Copolymer of PHA Bearing a Side Chain $R^1$ Representing an Isohexenyl Group and $R^2$ Representing an Isobutyl Group

[Chem. 46]

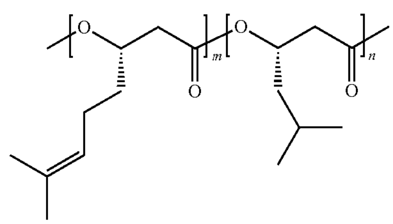

The production process of Example 3 is an adaptation of *Applied and Environmental Microbiology*, Vol. 60, No. 9. 3245-3254 (1994) "Polyester Biosynthesis Characteristics of *Pseudomonas citronellolis* Grown on Various Carbon Sources, Including 3-Methyl-Branched Substrate". Mun Hwan Choi and Sung Chul Yoon. The microorganism used is *Pseudomonas citronellolis* ATCC® 13674™. The culture method is performed under unfed-batch axenic culture conditions in 5 L Fernbach flasks (Corning® ref. 431685) containing 2 L of culture medium, shaken at 110 rpm at 30° C. in an orbital incubator (diameter of the orbit of 2.5 cm).

The production process is performed using two different culture media. The first culture medium, defined CM1 "inoculum", is used for the preparation of the preculture. The second culture medium, defined CM2 "batch", is used for unfed batch culture growth of the microorganism with the carbon source of interest in the Fernbach flasks.

TABLE 9

| Ingredients in grams per litre | CM1 <<inoculum>> | CM2 <<batch>> |
|---|---|---|
| $(NH_4)_2SO_4$ | / | 0.66 |
| $Na_2HPO_4$•$7H_2O$ | / | 7.3 |
| $KH_2PO_4$ | / | 2.3 |
| $NaHCO_3$ | / | 0.3 |
| $CaCl_2$•$2H_2O$ | / | 0.1 |
| $MgSO_4$•$7H_2O$ | / | 0.25 |
| Citric acid | / | 1.03 |
| Citronellol | / | 5.5 |
| Microelement solution | / | 1 |
| Nutrient broth | 1.5 | / |
| Yeast extract | 1 | / |
| 2N NaOH | QSP pH = 6.8 | |
| MilliQ water | QSP m = 1000 g | |

The composition of the Nutrient Broth, as mass percentages, is 37.5% beef extract and 62.5% peptone. Reference 233000 DIFCO™ ED.

The composition of the yeast extract, as a mass percentage, is 100% autolysate of the yeast *Saccharomyces cerevisiae*. Reference 210933 DIFCO™ ED.

TABLE 10

| Ingredients in grams per litre | Amount |
|---|---|
| $FeSO_4$•$7H_2O$ | 5.56 g |
| $CaCl_2$•$2H_2O$ | 3.0 g |
| $ZnSO_4$•$7H_2O$ | 0.58 g |
| $MnCl_2$•$4H_2O$ | 3.86 g |
| $H_3BO_3$ | 0.6 g |
| $CoCl_2$•$6H_2O$ | 5.62 g |
| $Na_2MoO_4$•$2H_2O$ | 0.06 g |
| $NiCl_2$•$6H_2O$ | 0.04 g |
| $CuSO_4$•$5H_2O$ | 0.34 g |
| HCl 0.5N | QSP 1000 g |

100 mL of preculture are prepared by suspending a cryotube containing 1 mL of the strain with 100 mL of "inoculum" culture medium at a pH adjusted to 6.8 with 2N NaOH in a 250 mL Fernbach flask and then incubated at 30° C. at 150 rpm for 24 hours. 1.9 L of CM2 "batch" culture medium placed in a presterilized 5 L Fernbach flask are inoculated at OD=0.1 with 100 mL of inoculum.

After 70 hours at 30° C. at 110 rpm, the biomass is dried by lyophilization before being extracted with dichloromethane for 24 hours. The suspension is clarified by filtration on a GF/A filter (Whatman®). The filtrate, composed of PHA dissolved in dichloromethane, is concentrated by evaporation and then dried under high vacuum at 40° C. to constant mass.

The PHA may optionally be purified by successive dissolution and precipitation, for instance using a dichloromethane/methanol system.

The PHA copolymer of Example 3 was fully characterized by spectroscopic and spectrometric methods and is in accordance with the expected chemical structure, with: 68 mol % of unit (A) for which $R^1$=isohexenyl and 32 mol % of unit (B) for which $R^2$=isobutyl.

Example 18: Copolymer of PHA Bearing a Side Chain $R^1$ Representing an Isohexyl Group and $R^2$ Representing an Isobutyl Group

[Chem. 48]

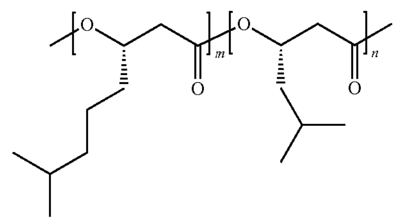

Example 18 is obtained by hydrogenation of Example 17 using an H-Cube Midi® continuous hydrogenator from ThalesNano Technologies.

A solution of 2 g (8.83 mmol) of Example 3 is prepared with a mixture composed of 100 mL of ethyl acetate (Sigma-Aldrich-CAS: 141-78-6) and 100 mL of methanol (Sigma-Aldrich-CAS: 67-56-1) is introduced at a flow rate of 3 mL per minute into a hydrogenation cartridge containing the catalyst containing 5% palladium on charcoal (Midi-Card ref. DHS 2141; ThalesNano Technologies) maintained at 100° C. under a pressure of 80 bar in the presence of hydrogen in the ThalesNano Technologies H-Cube Midi® system. The reduction of the double bond is monitored by NMR. After six consecutive cycles of reduction, the solution is concentrated by evaporation and then dried under vacuum to constant mass.

The PHA may optionally be purified by successive dissolution and precipitation, for instance using a dichloromethane/methanol system.

The PHA copolymer of Example 4 was fully characterized by spectroscopic and spectrometric methods and is in accordance with the expected chemical structure, with: 68 mol % of unit (A) for which $R^1$=isohexyl and 32 mol % of unit (B) for which $R^2$=isobutyl.

Example 19

A polymer was prepared using the microorganism *Pseudomonas putida* KT2440 ATCC® 47054™, octanoic acid.

The culture method was performed under batch axenic conditions in 5 L Fernbach flasks (Corning® ref. 431685) containing 2 L of culture medium, shaken at 110 rpm at 30° C. in an orbital incubator (diameter of the orbit of 2.5 cm).

The synthetic process was performed using two different culture media. The first culture medium, defined CM1 "inoculum", was used for the preparation of the inoculum. The second culture medium, defined CM2 "batch", was used for unfed batch growth of the microorganism with the octanoic acid in the Fernbach flasks.

The composition in grams per litre of the two media is described in Table 11 below:

TABLE 11

| | CM1 «inoculum» | CM2 «batch» |
|---|---|---|
| $(NH_4)_2SO_4$ | 4.7 | 5.02 |
| $Na_2HPO_4•7H_2O$ | 12 | 2.24 |
| $KH_2PO_4$ | 2.7 | 0.5 |
| Glucose | 9 | 3.9 |
| $MgSO_4•7H_2O$ | 0.8 | 1.03 |
| Citric acid | 1.6 | 1.03 |
| Nutrient Broth (1) | 1 | / |
| Octanoic acid | / | 3.8 |
| Microelement solution (2) | / | 1.4 |
| 2N NaOH | QSP pH = 6.8 | |
| Water | QSP 1000 g | |

(1) The composition of the Nutrient Broth, as mass percentages, is 37.5% beef extract and 62.5% peptone. Reference 233000 DIFCO™.
(2) The composition of the microelement solution in grams per litre is described in Table 12 below:

TABLE 12

| | |
|---|---|
| $FeSO_4•7H_2O$ | 10.0 g |
| $CaCl_2•2H_2O$ | 3.0 g |
| $ZnSO_4•7H_2O$ | 2.2 g |
| $MnSO_4•4H_2O$ | 0.5 g |
| $H_3BO_3$ | 0.3 g |
| $CoCl_2•6H_2O$ | 0.2 g |
| $Na_2MoO_4•2H_2O$ | 0.15 g |
| $NiCl_2•6H_2O$ | 0.02 g |
| $CuSO_4•5H_2O$ | 1.00 g |
| 0.5N HCl | QSP 1000 g |

100 mL of inoculum were prepared by suspending a cryotube containing 1 mL of the strain with 100 mL of "inoculum" culture medium at a pH adjusted to 6.8 with 2N NaOH in a 250 mL Fernbach flask and then incubated at 30° C. at 150 rpm for 24 hours. 1.9 L of CM2 "batch" culture medium placed in a presterilized 5 L Fernbach flask were inoculated at 00=0.1 with 100 mL of inoculum. After 70 hours at 30° C. at 110 rpm, the biomass was dried by lyophilization before being extracted with dichloromethane for 24 hours. The suspension was clarified by filtration on a GF/A filter (Whatman®). The filtrate, containing the copolymer dissolved in the dichloromethane, was concentrated by evaporation and then dried under high vacuum at 40° C. to constant mass. The crude polyhydroxyalkanoate was purified by precipitation from a solution of the latter dissolved in 10 times its weight of dichloromethane, in 10 volumes of cold methanol solution. The solid obtained was dried under high vacuum at 40° C. to constant mass.

The molecular weight of the polyhydroxyalkanoate obtained was characterized by size exclusion chromatography, with detection by refractive index.

Eluent: THF
Analytical flow rate: 1 mL/min
Injection: 100 µL
Columns: 1 Agilent PLGel Mixed-D 5 µm column; 300×7.5 mm; 1 Agilent PLGel Mixed-C 5 µm column; 300×7.5 mm; 1 Agilent Oligopore column; 300×7.5 mm
at room temperature (25° C.)
Detection: Waters 2487 Dual I Absorbance Detector, Waters 2414 Refractive Index Detector
Integrator: refractive index at 45° C. and 64 mV
Empower (GC Relative molar mass/conventional module)
Empower injection time: 40 min
Standards: High mass/EasiVial PS-H 4 mL polystyrene from Agilent Technologies, Part No. PL2010-0200

The analysis makes it possible to measure the weight-average molecular weight (Mw in g/mol), the number-average molecular weight (Mn in g/mol), the polydispersity index Ip (Mw/Mn) and the degree of polymerization DPn.

The monomer composition of the polyhydroxyalkanoate obtained was defined by gas chromatography equipped with a flame ionization detector.

The identification is performed by injection of commercial standards and the monomer composition was determined by a methanolysis and silylation treatment.

To determine the monomer composition, 7 mg of the polyhydroxyalkanoate polymer were dissolved in 1.5 mL of chloroform and subjected to methanolysis in the presence of 1.5 mL of an MeOH/HCl solution (17/2, v/v) at 100° C. for 4 hours. The organic phase was then washed with 1 mL of water and then dried over MgSO4. Silylation of the methyl esters formed was performed by adding 100 µL of BSTFA (N,O-bis(trimethylsilyl)trifluoroacetamide) and 100 µL of pyridine to the methylated sample. The solution was heated at 70° C. for 1 hour and then evaporated to dryness. The sample was then dissolved in 600 µL of dichloromethane and analysed by chromatography under the following conditions:

Hewlett Packard 6890 Series machine
ZB-5 HT stationary phase column from Phenomenex (length: 30 m, diameter: 0.25 mm)
Temperature: isotherm 60° C. to 300° C. in 6 min (heating rate: 10° C./min)
Gas: Helium; flow rate: 0.8 mL/min
Injector: Temperature: 250° C.; 50 ml/min
Flame ionization detector; Temperature: 300° C.
Injection: Volume 1 µL A copolymer containing 91% by weight of poly(3-hydroxyoctanoate), 6% by weight of poly(3-hydroxyhexanoate) and 3% by weight of poly(3-hydroxybutanoate) was thus obtained.

Mn=68 100 g/mol
Mw=149 100 g/mol
Ip=2.2
DPn=531

Example 2

A polymer was prepared using the microorganism *Pseudomonas putida* KT2440 ATCC® 47054™, octanoic acid and acrylic acid.

The culture method was performed under continuous axenic conditions at a dilution $D=0.25\ h^{-1}$ in a 3 L chemostat containing 1.1 L of culture medium. The system was aerated with air at a flow of 3 vvm (vvm=volume of air per volume of fermentation medium per minute) for a nominal dissolved oxygen ($O_D$) value at 30% of saturation.

The production process was performed using three different culture media. The first defined culture medium (CM1) was used for the preparation of the inoculum. The second defined culture medium (CM2) was used for unfed batch growth of the microorganism in the fermenter. The third defined culture medium (CM3) was used for the feeding, or maintenance, of the continuous fermentation containing octanoic acid and acrylic acid (β-oxidation pathway inhibitor).

The media CM1 and CM2 are identical to those described in Example 1. The composition in grams per litre of the medium CM3 is described in Table 13 below:

TABLE 13

| | CM3 «continuous» |
|---|---|
| $(NH_4)_2SO_4$ | 5.02 |
| $Na_2HPO_4$•$7H_2O$ | 2.24 |
| $KH_2PO_4$ | 0.5 |
| Glucose | 3 |
| $MgSO_4$•$7H_2O$ | 1.03 |
| Citric acid | 1.03 |
| Nutrient Broth (1) | / |
| Octanoic acid | 3.8 |
| Microelement solution (2) | 1.4 |
| Acrylic acid | 0.2 |
| 2N NaOH | QSP pH = 6.8 |
| Water | Qsp 1000 g |

100 mL of inoculum were prepared by suspending a cryotube containing 1 mL of the strain with 100 mL of Nutrient Broth at a pH adjusted to 7.0 with 2N NaOH in a 250 mL Fernbach flask and were then incubated at 30° C. at 150 rpm for 24 hours.

The fermenter containing 1 litre of culture medium CM2 at 30° C. was inoculated at an optical density of 0.1 at 630 nm (OD630=0.1). The system was maintained at 30° C. with shaking at 700±200 rpm and regulated in cascade with oxygenation for about 16 hours and/or the time for the microorganism to be able to reach its growth plateau.

Feeding of the fermenter with the medium CM3 was initiated when the microorganism reached its growth plateau, and withdrawal was then performed so as to maintain the initial mass of fermentation medium. Once the equilibrium state was reached in continuous culturing, a fraction of the withdrawn material was centrifuged so as to separate the biomass from the fermentation medium. The biomass was dried by lyophilization and then extracted with dichloromethane for 24 hours. The suspension obtained was clarified by filtration through a GF/A filter (Whatman®). The filtrate obtained, comprising the copolymer dissolved in dichloromethane, was concentrated by evaporation and then dried under high vacuum at 40° C. to constant mass. The crude polyhydroxyalkanoate was purified by precipitation from a solution of the latter dissolved in 10 times its weight of dichloromethane, in 10 volumes of cold methanol solution. The solid obtained was dried under high vacuum at 40° C. to constant mass.

A copolymer comprising 96% by weight of poly(3-hydroxyoctanoate), 3% by weight of poly(3-hydroxyhexanoate) and 1% by weight of poly(3-hydroxybutanoate) was thus obtained.

Mn=67 900 g/mol:

Mw=142 000 g/mol:

Ip=2.1:

DPn=611

Example 20

A polymer was prepared according to the procedure of Example 2, using nonanoic acid (instead of octanoic acid).

A copolymer comprising 86% by weight of poly(3-hydroxynonanoate), 9% by weight of poly(3-hydroxyheptanoate) and 5% by weight of poly(3-hydroxypentanoate) was thus obtained.

Mn=65 900 g/mol

Mw=143 600 g/mol

Ip=2.2

DPn=531

Example 21

A polymer was prepared according to the procedure of Example 2, using nonanoic acid (instead of octanoic acid) and without acrylic acid.

A copolymer comprising 68% by weight of poly(3-hydroxynonanoate), 27% by weight of poly(3-hydroxyheptanoate) and 5% by weight of poly(3-hydroxypentanoate) was thus obtained.

Mn=55 800 g/mol

Mw=124 500 g/mol

Ip=2.2

DPn=469

Example 22

A polymer was prepared according to the procedure of Example 2, using dodecanoic acid (instead of octanoic acid).

A copolymer comprising 44% by weight of poly(3-hydroxydodecanoate), 38% by weight of poly(3-hydroxydecanoate) and 18% by weight of poly(3-hydroxyoctanoate) was thus obtained.

Mn=67 400 g/mol

Mw=129 800 g/mol

Ip=1.9

DPn=484

Example 23: Copolymer of PHA Bearing a Side Chain $R^1$ Representing an n-Pentyl Group and $R^2$ Representing an n-Propyl Group

[Chem. 49]

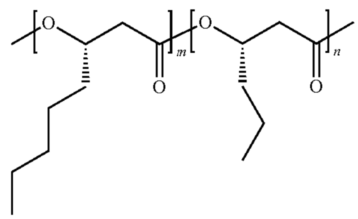

The production process of Example 23 is an adaptation of the article *Biomacromolecules* 2012, 13, 2926-2932: "Biosynthesis and Properties of Medium-Chain-Length Polyhydroxyalkanoates with Enriched Content of the Dominant Monomer"

The microorganism used is *Pseudomonas putida* ATCC® 47054™.

The culture method is performed under continuous axenic conditions at a dilution D=0.25 $h^{-1}$ in a 3 L chemostat containing 1.1 L of culture medium.

The system is aerated with a flow of 3 vvm of air for a nominal dissolved oxygen ($O_D$) value at 30% of saturation.

Assembly:

See FIG. 2

The production process is performed using three different culture media.

The first defined culture medium (CM1) is used for the preparation of the inoculum.

The second defined culture medium (CM2) is used for batch growth of the microorganism in the fermenter.

The third defined culture medium (CM3) is used for the feeding, or maintenance, of the continuous fermentation containing the carbon source of interest and the β-oxidation pathway inhibitor.

The composition in grams per litre of the three media is described in Table 14: composition in grams per litre of the culture media for the inoculum and the maintenance.

TABLE 14

| | CM1 «inoculum» | CM2 «batch» | CM3 «continuous» |
|---|---|---|---|
| $(NH4)_2SO4$ | 4.7 | 5.02 | 5.02 |
| $Na_2HPO4$•7H2O | 12 | 2.24 | 2.24 |
| $KH_2PO4$ | 2.7 | 0.5 | 0.5 |
| Glucose | 9 | 3.9 | 3 |
| MgSO4•7H2O | 0.8 | 1.03 | 1.03 |
| Citric acid | 1.8 | 1.03 | 1.03 |
| Nutrient Broth | 1 | / | / |
| Octanoic acid | / | / | 3.8 |
| Microelement solution | / | 1.4 | 1.4 |
| Acrylic acid | / | / | 0.2 |
| 2N NaOH | | QSP pH = 6.8 | |
| Milli water | | QSP m = 1000 g | |

The composition of the Nutrient Broth, as mass percentages, is 37.5% beef extract and 62.5% peptone. Reference 233000 DIFCO™.

The composition of the microelement solution in grams per litre is described in Table 15: composition in grams per litre of the microelement solution

TABLE 15

| | |
|---|---|
| FeSO4•7H2O | 10.0 g |
| CaCl2•2H2O | 3.0 g |
| ZnSO4•7H2O | 2.2 g |
| MnSO4•4H2O | 0.5 g |
| H3BO3 | 0.3 g |
| CoCl2•6H2O | 0.2 g |
| Na2MoO4•2H2O | 0.15 g |
| NiCl2•6H2O | 0.02 g |
| CuSO4•5H2O | 1.00 g |
| MilliQ | QSP 1000 g |

100 mL of inoculum are prepared by suspending a cryotube containing 1 mL of the strain with 100 mL of Nutrient Broth at a pH adjusted to 7.0 with 2N NaOH in a 250 mL Fernbach flask and are then incubated at 30° C. at 150 rpm for 24 hours.

The fermenter containing 1 litre of culture medium CM2 at 30° C. is inoculated at an optical density of 0.1 at 630 nm (OD630=0.1). The system is maintained at 30° C. with shaking at 700±200 rpm and regulated in cascade with oxygenation for about 16 hours and/or the time for the microorganism to be able to reach its growth plateau.

Feeding of the fermenter with the medium CM3 is initiated when the microorganism has reached its growth plateau, and withdrawal is then performed so as to maintain the initial mass of fermentation medium. Once the equilibrium state is reached in continuous culturing, a fraction of the withdrawn material is centrifuged so as to separate the biomass from the fermentation medium. The biomass is dried by lyophilization and is then extracted with dichloromethane for 24 hours. The suspension is clarified by filtration on a GF/A filter (Whatman®). The filtrate, composed of PHA dissolved in dichloromethane, is concentrated by evaporation and then dried under high vacuum at 40° C. to constant mass.

The PHA may optionally be purified by successive dissolution and precipitation, for instance using a dichloromethane/methanol system.

The PHA copolymer of Example 23 was fully characterized by spectrometric and spectroscopic methods. By gas chromatography equipped with an FID detector, it is seen that the copolymer contains 96% of radical $R^1$=n-pentyl and 4% of radical $R^2$=n-propyl.

Example 24: Copolymer of PHA Bearing a Side Chain $R^1$ Representing an n-Hexyl Group and $R^2$ Representing an n-Butyl Group

[Chem. 50]

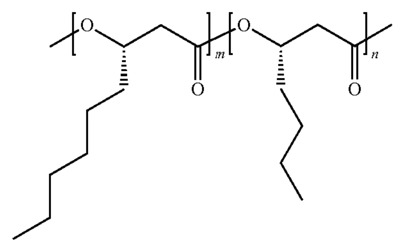

The production process of Example 24 is an adaptation of the article *Biomacromolecules,* 13, 2926-2932 (2012): "Biosynthesis and Properties of Medium-Chain-Length Polyhydroxyalkanoates with Enriched Content of the Dominant Monomer"

The microorganism used is *Pseudomonas putida* ATCC® 47054™.

The culture method is performed under continuous axenic conditions at a dilution D=0.25 $h^{-1}$ in a 3 L chemostat containing 1.1 L of culture medium.

The system is aerated with a flow of 3 vvm of air for a nominal dissolved oxygen ($O_D$) value at 30% of saturation. The assembly is identical to that of the preceding example.

The composition in grams per litre of the three media is described in Table 16: composition in grams per litre of the culture media for the inoculum and the maintenance.

TABLE 16

| | CM1 «inoculum» | CM2 «batch» | CM3 «continuous» |
|---|---|---|---|
| $(NH4)_2SO4$ | 4.7 | 5.02 | 5.02 |
| $Na_2HPO4$•7H2O | 12 | 2.24 | 2.24 |
| $KH_2PO4$ | 2.7 | 0.5 | 0.5 |
| Glucose | 9 | 3.9 | 3.9 |

TABLE 16-continued

| | CM1 «inoculum» | CM2 «batch» | CM3 «continuous» |
|---|---|---|---|
| MgSO4•7H2O | 0.8 | 1.03 | 1.03 |
| Citric acid | 1.6 | 1.03 | 1.03 |
| Nutrient Broth | 1 | / | / |
| Nonanoic acid | / | / | 3.8 |
| Microelement solution | / | 1.4 | 1.4 |
| Acrylic acid | / | / | 0.2 |
| 2N NaOH | QSP pH = 6.8 | | |
| MilliQ | QSP m = 1000 g | | |

The composition of the Nutrient Broth, as mass percentages, is 37.5% beef extract and 62.5% peptone. Reference 233000 DIFCO™.

The composition of the microelement solution in grams per litre is described in Table 15.

100 mL of inoculum are prepared by suspending a cryotube containing 1 mL of the strain with 100 mL of Nutrient Broth at a pH adjusted to 7.0 with 2N NaOH in a 250 mL Fernbach flask and are then incubated at 30° C. at 150 rpm for 24 hours.

The fermenter containing 1 litre of culture medium CM2 at 30° C. is inoculated at an optical density of 0.1 at 630 nm (00630=0.1). The system is maintained at 30° C. with shaking at 700±200 rpm and regulated in cascade with oxygenation for about 16 hours and/or the time for the microorganism to be able to reach its growth plateau.

Feeding of the fermenter with the medium CM3 is initiated when the microorganism has reached its growth plateau, and withdrawal is then performed so as to maintain the initial mass of fermentation medium. Once the equilibrium state is reached in continuous culturing, a fraction of the withdrawn material is centrifuged so as to separate the biomass from the fermentation medium. The biomass is dried by lyophilization and is then extracted with dichloromethane for 24 hours. The suspension is clarified by filtration on a GF/A filter (Whatman®). The filtrate, composed of PHA dissolved in dichloromethane, is concentrated by evaporation and then dried under high vacuum at 40° C. to constant mass.

The PHA copolymer of Example 24 may optionally be purified by successive dissolution and precipitation, for instance using a dichloromethane/methanol system.

The PHA copolymer of Example 24 was fully characterized by spectrometric and spectroscopic methods. By gas chromatography equipped with an FID detector, it is seen that the copolymer contains 86% of radical $R^1$=n-hexyl and 14% of radical $R^2$=n-butyl.

Example 25: Copolymer of PHA Bearing a Side Chain $R^1$ Representing an n-Nonyl Group and $R^2$ Representing an n-Heptyl Group

[Chem. 51]

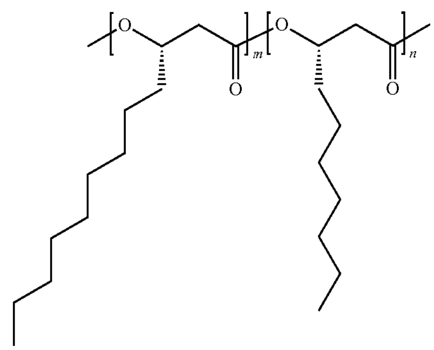

The production process of Example 25 is an adaptation of patent CA2781699C, Example 10.

The microorganism used is *Pseudomonas putida* ATCC® 47054™.

The culture method is performed under continuous axenic conditions at a dilution D=0.25 $h^{-1}$ in a 3 L chemostat containing 1.1 L of culture medium.

The system is aerated with a flow of 3 vvm of air for a nominal dissolved oxygen ($O_D$) value at 30% of saturation. The assembly is identical to that of Example 23.

The production process is performed using three different culture media.

The first defined culture medium (CM1) is used for the preparation of the inoculum.

The second defined culture medium (CM2) is used for batch growth of the microorganism in the fermenter.

The third defined culture medium (CM3) is used for the feeding, or maintenance, of the continuous fermentation containing the carbon source of interest and the β-oxidation pathway inhibitor.

The composition in grams per litre of the three media is described in Table 17: composition in grams per litre of the culture media for the inoculum and the maintenance.

TABLE 17

| | CM1 «inoculum» | CM2 «batch» | CM3 «continuous» |
|---|---|---|---|
| $(NH4)_2SO4$ | 4.7 | 5.02 | 5.02 |
| $Na_2HPO4$•7H2O | 12 | 2.24 | 2.24 |
| $KH_2PO4$ | 2.7 | 0.5 | 0.5 |
| Glucose | 9 | 3.9 | 3 |
| MgSO4•7H2O | 0.8 | 1.03 | 1.03 |
| Citric acid | 1.6 | 1.03 | 1.03 |
| Nutrient Broth | 1 | / | / |
| Dodecanoic acid | / | / | 1.14 |
| Microelement solution | / | 1.4 | 1.4 |
| Acrylic acid | / | / | 0.2 |
| 2N NaOH | QSP pH = 6.8 | | |
| MilliQ | QSP m = 1000 g | | |

The composition of the Nutrient Broth, as mass percentages, is 37.5% beef extract and 62.5% peptone. Reference 233000 DIFCO™.

The composition of the microelement solution in grams per litre is described in Table 15.

100 mL of inoculum are prepared by suspending a cryotube containing 1 mL of the strain with 100 mL of Nutrient Broth at a pH adjusted to 7.0 with 2N NaOH in a 250 mL Fernbach flask and are then incubated at 30° C. at 150 rpm for 24 hours. The fermenter containing 1 litre of culture medium CM2 at 30° C. is inoculated at an optical density of 0.1 at 630 nm (OD630=0.1). The system is maintained at 30° C. with shaking at 700±200 rpm and regulated in cascade with oxygenation for about 16 hours and/or the time for the microorganism to be able to reach its growth plateau. Feeding of the fermenter with the medium CM3 is initiated when the microorganism has reached its growth plateau, and withdrawal is then performed so as to maintain the initial mass of fermentation medium. Once the equilibrium state is reached in continuous culturing, a fraction of the withdrawn material is centrifuged so as to separate the biomass from the fermentation medium. The biomass is dried by lyophilization and is then extracted with dichloromethane for 24 hours. The suspension is clarified by filtration on a GF/A filter (Whatman®). The filtrate, composed of PHA dissolved in dichloromethane, is concentrated by evaporation and then dried under high vacuum at 40° C. to constant mass. The PHA copolymer may optionally be purified by successive dissolution and precipitation, for instance using a dichloromethane/methanol system.

The PHA copolymer of Example 25 was fully characterized by spectrometric and spectroscopic methods. By GC chromatography, it is seen that the copolymer contains 55% of radical $R^1$=n-nonyl, 33% of radical $R^2$=n-heptyl; 11% of radical $R^3$=n-pentyl, 1.1% of R4=propyl and % $R^5$=methyl.

Emulsification

Example 26: Direct Emulsion Using the PHA Copolymer of Example 23

Sodium laureth sulfate; sodium lauryl ether sulfate SLES (2.0 or 2.2 OE) anionic surfactants as an aqueous solution at 70% AM in water 5 g of PHA copolymers of Example 23 are dissolved at room temperature with 45 g of ethyl acetate (EtOAc) before being dispersed with a solution of 50 g of SLES at 1% AM (0.7 g qs 50 g of demineralized water) using an Ultra-Turrax blender (25 mm spindle) at 24 000 rpm (revolutions per minute) in a jacketed reactor at 5° C. for 10 minutes. A temperature rise from 18° C. to 33° C. is observed.

The EtOAc is distilled off in successive stages on a bath at 45° C.

The mixture is made up to 35 g with water to obtain a white dispersion with blueish tints.

The dispersion is filtered at 0.45 μm under PSM.

Example 27: Direct Emulsion Using the PHA Copolymer of Example 24

The emulsion was prepared in the same manner as in the preceding example, starting with 5 g of copolymer of Example 24 instead of Example 23.

Example 28: Direct Emulsion Using the PHA Copolymer of Example 25

The emulsion was prepared in the same manner as in the preceding example, starting with 5 g of copolymer of Example 25 instead of Example 23.

Example 29: Inverse Emulsion Starting with the Copolymer of Example 24 (13% in the Fatty Phase)

Composition:

TABLE 18

| Ingredients | Amount in g/100 g |
|---|---|
| Copolymer of Example 24 | 4.80 |
| CETYL PEG/PPG-10/1 DIMETHICONE (surfactant) | 3.6 |
| Poluglyceryl-4 isostearate (surfactant) | 1.2 |
| Isododecane | 31.7 |
| Butylene glycol | 7.2 |
| Magnesium sulfate | 0.8 |
| Denatured alcohol | 9.5 |
| Water | Qsp 100 |

Protocol:

An aqueous phase is prepared by successive introduction of the ingredients of Table 8 with stirring at room temperature.

TABLE 19

| | Ingredients | Amount in g |
|---|---|---|
| Aqueous phase. | Butylene glycol | 7.2 |
| | Magnesium sulfate | 0.8 |
| | Denatured alcohol | 9.5 |
| | Water | 41.2 |

The fatty phase is prepared in a 20 mL vial by introduction of the ingredients of Table 9 with stirring at 70° C. for 1 hour. The clear solution is brought to room temperature with stirring.

TABLE 20

| | | Name of the ingredients | Amount in g |
|---|---|---|---|
| Fatty phase (organic) | Surfactant | CETYL PEG/PPG-10/1 DIMETHICONE | 3.6 |
| | | POLYGLYCERYL-4 ISOSTEARATE | 1.2 |
| | Solvents | ISODODECANE | 31.7 |
| | PHA | Example 24 | 4.8 |

4.13 g of the fatty phase are diluted with 5.87 g of aqueous phase and the emulsion is prepared using an Ultra-Turrax blender (10 mm spindle) at 24 000 rpm for 10 minutes on a bath of ice-water.

The bright white and relatively fluid dispersion does not change in appearance after two weeks at room temperature (25° C.).

Example 30: Inverse Emulsion Starting with the Copolymer of Example 24 (28% in the Fatty Phase)

Composition:

TABLE 21

| Ingredients | Amount in g/100 g |
|---|---|
| Copolymer of Example 24 | 10 |
| CETYL PEG/PPG-10/1 DIMETHICONE (surfactant) | 3.6 |
| Polyglyceryl-4 isostearate (surfactant) | 1.2 |
| Isododecane | 26.5 |
| Butylene glycol | 7.2 |
| Magnesium sulfate | 0.8 |
| Denatured alcohol | 9.5 |
| Water | Qsp 100 |

Protocol: Is Identical to that of the Preceding Example with the Same Aqueous Phase but a Different Amount of Fatty Phase:

TABLE 21

| | | Name of the ingredients | Amount in g |
|---|---|---|---|
| Fatty phase | Surfactant | CETYL PEG/PPG-10/1 DIMETHICONE | 3.6 |
| | | POLYGLYCERYL-4 ISOSTEARATE | 1.2 |
| | Solvents | ISODODECANE | 26.5 |
| | PHA | Example 24 | 10 |

4.13 g of the fatty phase are diluted with 5.87 g of aqueous phase and the emulsion is prepared using an Ultra-Turrax blender (10 mm spindle) at 24 000 rpm for 10 minutes on a bath of ice-water.

The bright white and relatively fluid dispersion does not change in appearance after two weeks at room temperature (25° C.).

EVALUATIONS

In a first stage, a film is prepared on a contrast card with a film spreader (speed: 50 mm/s-Cylinder: 100 μm). The film is left to dry for 24 hours at room temperature. Once dry, the film has a thickness of about 40 μm, FIG. 1.

For the PHA copolymers of Examples 1 to 4 that are soluble in isododecane or an isododecane/ethanol mixture, evaluation of the cosmetic properties on a dry film was performed.

In a first stage, a film is prepared on a contrast card with a film spreader (speed: 50 mm/s-Cylinder: 100 μm). The film is left to dry for 24 hours at room temperature. Once dry, the film has a thickness of about 40 μm.

Three evaluations are performed on the dry film: Resistance to fats, gloss and tackiness Measurement of the Resistance to Fats Three drops of olive oil or sebum or water were deposited on the dry film present on the black part of the contrast card. Each drop corresponds to about 10 μL of olive oil (use of a micropipette).

The drop is left in contact with the dry film for two times: 5 minutes and 30 minutes. Once the time has elapsed, the drop of olive oil or sebum or water is wiped off and observation of the deterioration of the polymer film is performed. If the film was damaged by the drop of olive oil or sebum or water, the polymer film is regarded as being non-resistant to olive oil or to sebum.

Measure of the Resistance Vs Water/Oil and Adhesive Tape can Also be Evaluated

Mixing of the polymer dissolved in isododecane or isododecane/ethanol with the pigment for 2 minutes at 3500 rpm. The evaluations are performed on BioSkin. In a first stage, a film of each formulation is deposited on a BioSkin sample by means of a film spreader. The thickness of the wet film is 100 μm. The films are dried for 24 hours at room temperature. Once the films are dry, the tests may be performed.

Resistance to Olive Oil/Sebum 0.5 mL of olive oil or sebum is applied to the film of formulation. After 5 minutes, the olive oil or sebum is removed by wiping 15 times with cotton wool. The deterioration of the film following contact with the olive oil or the sebum is thus examined (see FIG. 3).

Resistance to Adhesive Tapes

A strip of adhesive tape (of Scotch® type) is applied to the film of formulation. A weight is applied to the strip of said tape for 30 seconds. The adhesive tape is then removed and mounted on a slide holder so as to observe the result. The adherence of the film to the support is thus evaluated (see FIG. 3).

Example 31: Direct Emulsion Starting with the PHA of Example 24 with a Cationic SA Having an HLB>10

SA=cationic: cetrimonium chloride

PHA=(copo PHN at 86% PHHx at 14%)

5 g of PHA are dissolved at room temperature with 45 g of ethyl acetate before being dispersed with a solution of 50 g of SA at 1% AM (0.5 g qs=50 g of demineralized water) using an Ultra-Turrax blender (25 mm spindle) at 24 000 rpm in an ice-water bath at 5° C. for 10 minutes.

The ethyl acetate is distilled off in successive stages on a bath at 45° C. Evaporation of the water is performed in successive stages on a bath at 45° C. The white dispersion with blueish tints is made up to 35 g with demineralized water.

Example 32: Direct Emulsion Starting with the PHA Described in Example 24 with a Nonionic SA Having an HLB<10

SA=nonionic: Span 80 (sorbitan monooleate)

PHA=(copo PHN at 86% PHHx at 14%)

5 g of PHA are dissolved at room temperature with 45 g of ethyl acetate before being dispersed with a solution of 50 g of SA at 1% AM (0.5 g qs=50 g of demineralized water) using an Ultra-Turrax blender (25 mm spindle) at 24 000 rpm in an ice-water bath at 5° C. for 10 minutes.

The ethyl acetate is distilled off in successive stages on a bath at 45° C. Evaporation of the water is performed in successive stages on a bath at 45° C. The two-phase white suspension is made up to 35 g with demineralized water.

SA=nonionic: polyglyceryl-4 isostearate

PHA=(copo PHN at 86% PHHx at 14%)

5 g of PHA are dissolved at room temperature with 45 g of ethyl acetate before being dispersed with a solution of 50 g of SA at 1% AM (0.5 g qs=50 g of demineralized water) using an Ultra-Turrax blender (25 mm spindle) at 24 000 rpm in an ice-water bath at 5° C. for 10 minutes.

The ethyl acetate is distilled off in successive stages on a bath at 45° C. Evaporation of the water is performed in successive stages on a bath at 45° C. The two-phase white suspension is made up to 35 g with demineralized water.

Example 33: Direct Emulsion Starting with the PHA Described in Example 24 with a Nonionic SA Having an HLB>10

SA=nonionic: polysorbate 40=Tween 40

PHA=(copo PHN at 86% PHHx at 14%)

5 g of PHA are dissolved at room temperature with 45 g of ethyl acetate before being dispersed with a solution of 50 g of SA at 1% AM (0.5 g qs=50 g of demineralized water) using an Ultra-Turrax blender (25 mm spindle) at 24 000 rpm in an ice-water bath at 5° C. for 10 minutes.

The ethyl acetate is distilled off in successive stages on a bath at 45° C. Evaporation of the water is performed in successive stages on a bath at 45° C. The two-phase white suspension is made up to 35 g with demineralized water.

SA=nonionic: laureth 23

PHA=(copo PHN at 86% PHHx at 14%)

5 g of PHA are dissolved at room temperature with 45 g of ethyl acetate before being dispersed with a solution of 50 g of SA at 1% AM (0.5 g qs=50 g of demineralized water) using an Ultra-Turrax blender (25 mm spindle) at 24 000 rpm in an ice-water bath at 5° C. for 10 minutes.

The ethyl acetate is distilled off in successive stages on a bath at 45° C. Evaporation of the water is performed in successive stages on a bath at 45° C. The two-phase white suspension is made up to 35 g with demineralized water.

The stability of the direct emulsions as a function of the nature of the surfactant is summarized in the following table.

TABLE 22

| Name of the SA | HLB | Family | Stability of the direct emulsion |
|---|---|---|---|
| Laureth sulfate (SLES) | 40 | Anionic HLB+ | +++ |
| Cetrimonium chloride (CTAC) | 15.8 | Cationic HLB+ | +++ |

Table 22 summarizes the evaluations for the various emulsions.

TABLE 22

| | Examples | | | | | |
|---|---|---|---|---|---|---|
| | Ex. 26 | Ex. 27 | Ex. 28 | Ex. 31 | Ex. 29 | Ex. 30 |
| Emulsion direction | Direct | Direct | Direct | Direct | Inverse | Inverse |
| Water resistance | +++ | ++ | +++ | +++ | +++ | +++ |
| Olive oil resistance | +++ | +++ | +++ | +++ | ++ | ++ |
| Sebum resistance | +++ | +++ | +++ | +++ | + | + |
| Gloss at 20° | Matt deposit (gloss = 5) | Matt deposit (gloss = 6) | Matt deposit (gloss = 5) | Matt deposit (gloss = 7) | Matt deposit (gloss = 5) | Matt deposit (gloss = 7) |

It is seen that the compositions of the invention make it possible to obtain significant resistance to water, oil and sebum.

The invention claimed is:

1. A cosmetic composition comprising:

a) 0.1% by weight to 30% by weight of one or more polyhydroxyalkanoate (PHA) film-forming copolymers relative to the total weight of the composition, which contain, at least two different repeating polymer units chosen from the units (A) and (B) below, and the optical or geometrical isomers thereof, the organic or mineral acid or base salts thereof, and the solvates thereof being selected from the group of hydrates and linear or branched $C_1$-$C_4$ alcohols:

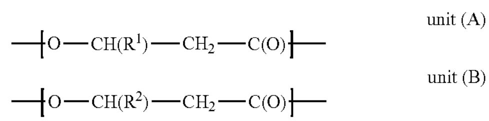

in which polymer units (A) and (B):

$R^1$ represents a hydrocarbon-based chain chosen from i) linear or branched ($C_5$-$C_{28}$)alkyl, ii) linear or branched ($C_5$-$C_{28}$)alkenyl, iii) linear or branched ($C_5$-$C_{28}$)alkynyl;

said hydrocarbon-based chain being:

optionally substituted with one or more atoms or groups chosen from: a) halogen, b) hydroxyl, c) thiol, d) (di)($C_1$-$C_4$)(alkyl)amino, e) (thio)carboxy, f) (thio)carboxamide-C(O)—N($R_a$)$_2$ or C(S)—N($R_a$)$_2$, g) cyano, h) iso(thio)cyanate, i) (hetero)aryl and j) (hetero)cycloalkyl k) cosmetic active agent; 1) R—X with R representing a group chosen from α) cycloalkyl, β) heterocycloalkyl, γ) (hetero)aryl, δ) cosmetic active agent as defined previously and X representing a') O, S, N($R_a$) or Si($R_b$)($R_c$), b') S(O)$_r$, or (thio)carbonyl, c') or combinations of a') with b'); $R_a$ representing a hydrogen atom, or a ($C_1$-$C_4$)alkyl group or an aryl($C_1$-$C_4$)alkyl group $R_b$ and $R_c$, which may be identical or different, represent a ($C_1$-$C_4$) alkyl or ($C_1$-$C_4$)alkoxy group; and/or optionally interrupted with one or more heteroatoms a') O, S, N($R_a$) or Si($R_b$)($R_c$), b') S(O)$_r$, (thio)carbonyl, c') or combinations of a') with b') with r being equal to 1 or 2, $R_a$ being as defined previously, $R_b$ and $R_c$ being as defined previously;

$R^2$ represents a cyclic or non-cyclic, linear or branched, saturated or unsaturated hydrocarbon-based group comprising from 3 to 30 carbon atoms; and b) 0.1% by weight to 30% by weight of one or more surfactant(s) relative to the total weight of the composition; and c) optionally one or more fatty substances;

it being understood that (A) is different from (B), and wherein the unit (A) is present in a molar percentage ranging from 0.1% to 99%; and the unit (B) is present in a molar percentage ranging from 1% to 40% based on the weight of (A) and (B) in the one or more polyhydroxyalkanoate (PHA) copolymers.

2. The composition according to claim 1, in which the one or more polyhydroxyalkanoate (PHA) film-forming copolymers a) contain the repeating unit of formula (I), and the optical or geometrical isomers thereof, the organic or mineral acid or base salts thereof, and the solvates thereof being selected from the group of hydrates and linear or branched $C_1$-$C_4$ alcohols:

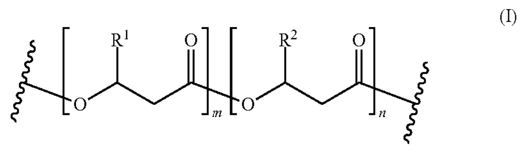

(I)

in which formula (I):

m and n are integers greater than or equal to 1.

3. The composition according to claim 1, in which the one or more polyhydroxyalkanoate (PHA) film-forming copolymers a) contain three different repeating polymer units (A), (B) and (C), below, and the optical or geometrical isomers thereof and the solvates thereof being selected from the group of hydrates and linear or branched $C_1$-$C_4$ alcohols:

unit (A)

unit (B)

unit (C)

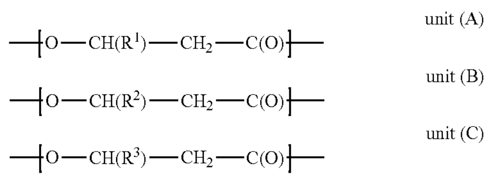

in which polymer units (A), (B) and (C):

$R^3$ represents a cyclic or non-cyclic, linear or branched, saturated or unsaturated hydrocarbon-based group comprising from 1 to 30 carbon atoms; and it being understood that:

(A) is different from (B) and (C), (B) is different from (A) and (C), and (C) is different from (A) and (B).

4. The composition according to claim 1, in which the one or more polyhydroxyalkanoate (PHA) film-forming copolymers a) contain four different repeating polymer units (A), (B), (C) and (D), below, and the optical or geometrical isomers thereof, the organic or mineral acid or base salts thereof, and also the solvates thereof being selected from the group of hydrates and linear or branched $C_1$-$C_4$ alcohols:

unit (A)

unit (B)

unit (C)

unit (D)

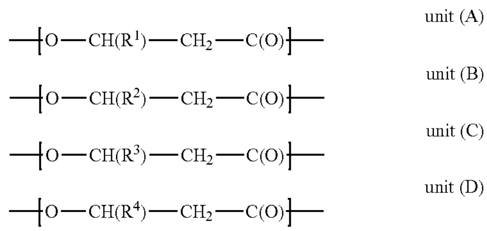

in which polymer units (A), (B), (C) and (D):

$R^4$ represents a cyclic or non-cyclic, linear or branched, saturated hydrocarbon-based group comprising from 3 to 30 carbon atoms optionally substituted with one or more atoms or groups a) to 1) and/or optionally interrupted with one or more heteroatoms or groups a') to c') as defined for $R^1$; and it being understood that:

(A) is different from (B), (C) and (D), (B) is different from (A), (C) and (D), (C) is different from (A), (B) and (D), and (D) is different from (A), (B) and (C).

5. The composition according to claim 1, in which the one or more polyhydroxyalkanoate (PHA) film-forming copolymers a) contain five different repeating polymer units (A), (B), (C), (D) and (E), and the optical or geometrical isomers thereof, the organic or mineral acid or base salts thereof, and also the solvates thereof being selected from the group of hydrates and linear or branched $C_1$-$C_4$ alcohols:

unit (A)

unit (B)

unit (C)

unit (D)

unit (E)

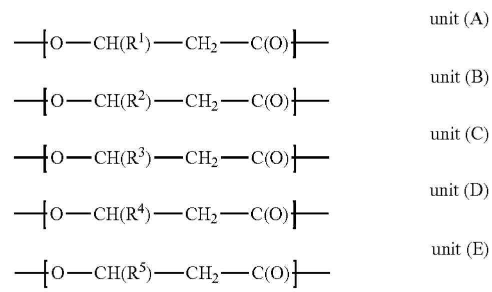

in which polymer units (A), (B), (C), (D) and (E):

$R^5$ represents a cyclic or non-cyclic, linear or branched, saturated hydrocarbon-based group comprising from 3 to 30 carbon atoms optionally substituted with one or more atoms or groups a) to 1) and/or optionally interrupted with one or more heteroatoms or groups a') to c') as defined for $R^1$;

it being understood that:

(A) is different from (B), (C), (D) and (E); (B) is different from (A), (C), (D) and (E); (C) is different from (A), (B), (D) and (E); (D) is different from (A), (B), (C) and (E); and (E) is different from (A), (B), (C) and (D).

6. The composition according to claim 1, in which $R^1$ represents a linear or branched $(C_5$-$C_{28})$alkyl hydrocarbon-based chain.

7. The composition according to claim 1, in which $R^1$ represents a hydrocarbon-based chain.

8. The composition according to claim 1, in which $R^1$ has the following formula $-(CH_2)_r-X-(ALK)_u-G$ with X being as defined previously, ALK represents a linear or branched $(C_1$-$C_{10})$alkylene, r represents an integer inclusively between 6 and 11, u is equal to 0 or 1; and G represents a hydrogen atom or a group chosen from hydroxyl, carboxyl, (di)$(C_1$-$C_4)$(alkyl)amino, (hetero)aryl, cycloalkyl, or a sugar.

9. The composition according to claim 1, in which the one or more polyhydroxyalkanoate (PHA) film-forming copolymers a) are such that $R^2$ is chosen from linear or branched $(C_1$-$C_{28})$alkyl, and linear or branched $(C_2$-$C_{28})$alkenyl.

10. The composition according to claim 1, in which the one or more polyhydroxyalkanoate (PHA) film-forming copolymers a) are such that the radical $R^2$ is a linear $(C_1$-$C_8)$alkyl group; or $R^2$ is a branched $(C_3$-$C_8)$alkyl.

11. The composition according to claim 3, in which the one or more polyhydroxyalkanoate (PHA film-forming copolymers a) are such that:

the unit (A) is present in a molar percentage ranging from 0.5% to 50%; and the unit (B) is present in a molar percentage ranging from 2% to 10% and/or the unit (C) is present in a molar percentage ranging from 0.5% to 20%.

12. The composition according to claim 1, in which b) the surfactant(s) are ionic; and/or the surfactant(s) b) have a HLB value greater than 10.

13. The composition according to claim 1, which is a direct emulsion.

14. The composition according to claim 1, which is an inverse emulsion.

15. The composition according to claim 1, in which the fatty medium comprises one or more substances chosen from:

branched $C_8$-$C_{16}$ alkanes, linear $C_8$-$C_{16}$ alkanes;

ester oils;

monoester oils of formula $R^9$—C(O)—$OR^{10}$ in which $R^9$ represents a linear or branched hydrocarbon-based chain including from 5 to 19 carbon atoms and $R^{10}$ represents a linear or branched, notably branched, hydrocarbon-based chain containing from 4 to 20 carbon atoms, on condition that $R^9+R^{10}\geq 9$ carbon atoms;

esters of lactic acid and of $C_{10}$-$C_{20}$ alcohol;

diesters of malic acid and of $C_{10}$-$C_{20}$ alcohol;

esters of pentaerythritol and of $C_8$-$C_{22}$ carboxylic acid;

diesters of formula $R^{11}$—O—C(═O)—$R^{12}$—C(═O)—O—$R^{13}$, with $R^{11}$ and $R^{13}$, which may be identical or different, representing a linear or branched, saturated or unsaturated $C_4$ to $C_{12}$ alkyl chain, optionally containing at least one saturated or unsaturated ring, and $R^{12}$ representing a saturated or unsaturated $C_1$ to $C_4$, alkylene chain;

diesters of formula $R^{14}$—C(═O)—O—$R^{15}$—O—C(═O)—$R^{16}$, with $R^{14}$ and $R^{16}$, which may be identical or different, representing a linear or branched, saturated or unsaturated $C_4$ to $C_{12}$ alkyl chain and $R^{15}$ representing a saturated or unsaturated $C_1$ to $C_4$ alkylene chain;

the carbonate oils being chosen from the carbonates of the following formula $R^{17}$—O—C(O)—O—$R^{18}$, with $R^{17}$ and $R^{18}$, which may be identical or different, representing a linear or branched $C_4$ to $C_{12}$ alkyl chain;

and mixtures thereof.

16. The composition according to claim 1, in which the fatty medium comprises one or more fatty substances in a content ranging from 2% to 99.9% by weight, relative to the total weight of the composition.

17. The composition according to claim 1, in which the fatty medium comprises one or more solvents.

18. The composition according to claim 1, which further comprises one or more colouring agents chosen from pigments, direct dyes and mixtures thereof.

19. A process for treating keratin materials by applying the composition as defined in claim 1.

20. The composition according to claim 1, in which the one or more polyhydroxyalkanoate (PHA) film-forming copolymers a) are such that they comprise the following repeating units, and the optical or geometrical isomers thereof, the organic or mineral acid or base salts thereof, and the solvates thereof being selected from the group of hydrates and linear or branched $C_1$-$C_4$ alcohols:

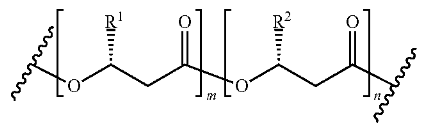

| Compounds | $R^1$ | $R^2$ |
|---|---|---|
| (1) | $-(CH_2)_8-S-CH(CH_3)-C(O)-OH$ | $-(CH_2)_4-CH_3$ |
| (2) | $-(CH_2)_8-S-(CH_2)_7-CH_3$ | $-(CH_2)_4-CH_3$ |
| (3) | $-(CH_2)_8-S-(CH_2)_8-OH$ | $-(CH_2)_4-CH_3$ |
| (4) | $-(CH_2)_8-S-(CH_2)_2-NH_2$ | $-(CH_2)_4-CH_3$ |
| (5) | $-(CH_2)_8-S-$Cycl | $-(CH_2)_4-CH_3$ |
| (6) | $-(CH_2)_8-S-CH_2-$Fur | $-(CH_2)_4-CH_3$ |
| (7) | $-(CH_2)_8-S-$Sug | $-(CH_2)_4-CH_3$ |
| (8) | $-(CH_2)_8-S-(CH_2)_2-$Ar | $-(CH_2)_4-CH_3$ |
| (9) | $-(CH_2)_8-S-CH_2-$Ar' | $-(CH_2)_4-CH_3$ |
| (10) | $-(CH_2)_8-S-CH(CH_3)-C(O)-OH$ | $-(CH_2)_5-CH_3$ |
| (11) | $-(CH_2)_5-$Hal | $-(CH_2)_5-CH_3$ |
| (12) | $-(CH_2)_3-CN$ | $-(CH_2)_5-CH_3$ |
| (13) | 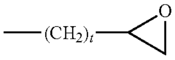 | $-(CH_2)_5-CH_3$ |
| (14) | $-(CH_2)_2-$Ar | $-(CH_2)_5-CH_3$ |
| (15) | $-(CH_2)_4-CH_3$ | $-(CH_2)_2-CH_3$ |
| (16) | $-(CH_2)_5-CH_3$ | $-(CH_2)_3-CH_3$ |
| (17) | $-(CH_2)_6-CH_3$ | $-(CH_2)_4-CH_3$ |
| (18) | $-(CH_2)_8-CH_3$ | $-(CH_2)_6-CH_3$ |
| (19) | $-(CH_2)_3-CH(CH_3)CH_3$ | $-CH_2-CH(CH_3)CH_3$ |
| (20) | $-(CH_2)_6-CH=CH_2$ | $-(CH_2)_5-CH_3$ |
| (21) | $-(CH_2)_2-CH=C(CH_3)CH_3$ | $-CH_2-CH(CH_3)CH_3$ |

m and n are aintegers greater that or equal to 1,
Hal represents a halogen atom and
t represents an integer between 1 and 10,
Ar: represents a (hetero)aryl group;
Ar': represents a ($C_1$-$C_4$)alkyl(hetero aryl group;
Cycl: represents a cyclohexyl group;
Fur: represents a furyl group; and
Sug: represents a sugar group.

21. The composition according to claim 1, in which the one or more polyhydroxyalkanoate (PHA) film-forming copolymers a) wherein $R^1$ of the unit (A) a saturated hydrocarbon-based chain and the unit (A) is present in a molar percentage between 60% and 90% of the one or more polyhydroxyalkanoate (PHA) copolymers a).

22. The composition according to claim 20, wherein the one or more polyhydroxyalkanoate (PHA) film-forming copolymers a) bear a chain $R^1$ representing a n-pentyl group and $R^2$ representing a n-propyl group; or bear a chain $R^1$ representing a n-hexyl group and $R^2$ representing a n-butyl group; or bear a chain $R^1$ representing a n-nonyl group and $R^2$ representing a n-heptyl group.

* * * * *